(12) United States Patent
Pellecchia et al.

(10) Patent No.: US 9,115,061 B2
(45) Date of Patent: Aug. 25, 2015

(54) NAPHTHALENE-BASED INHIBITORS OF ANTI-APOPTOTIC PROTEINS

(75) Inventors: Maurizio Pellecchia, La Jolla, CA (US); John C. Reed, La Jolla, CA (US)

(73) Assignee: BURNHAM INSTITUTE FOR MEDICAL RESEARCH, La Jolla, CA (US)

( * ) Notice: Subject to any disclaimer, the term of this patent is extended or adjusted under 35 U.S.C. 154(b) by 1717 days.

(21) Appl. No.: 12/253,918

(22) Filed: Oct. 17, 2008

(65) Prior Publication Data

US 2009/0105319 A1 Apr. 23, 2009

Related U.S. Application Data

(60) Provisional application No. 60/981,400, filed on Oct. 19, 2007, provisional application No. 61/035,969, filed on Mar. 12, 2008, provisional application No. 61/097,171, filed on Sep. 15, 2008.

(51) Int. Cl.

| C07C 239/00 | (2006.01) |
|---|---|
| C07C 39/14 | (2006.01) |
| C07C 47/575 | (2006.01) |
| C07C 49/83 | (2006.01) |
| C07C 49/84 | (2006.01) |
| C07C 235/66 | (2006.01) |
| C07C 311/29 | (2006.01) |
| C07D 277/64 | (2006.01) |

(52) U.S. Cl.
CPC ............... *C07C 39/14* (2013.01); *C07C 47/575* (2013.01); *C07C 49/83* (2013.01); *C07C 49/84* (2013.01); *C07C 235/66* (2013.01); *C07C 311/29* (2013.01); *C07D 277/64* (2013.01); *C07C 2101/08* (2013.01); *C07C 2101/14* (2013.01)

(58) Field of Classification Search
None
See application file for complete search history.

(56) References Cited

U.S. PATENT DOCUMENTS

| 4,559,157 | A | 12/1985 | Smith et al. | |
|---|---|---|---|---|
| 4,608,392 | A | 8/1986 | Jacquet et al. | |
| 4,820,508 | A | 4/1989 | Wortzman | |
| 4,938,949 | A | 7/1990 | Borch et al. | |
| 4,992,478 | A | 2/1991 | Geria | |
| 7,223,395 | B2 | 5/2007 | Muller et al. | |
| RE40,862 | E | 7/2009 | Flack et al. | |
| 8,039,668 | B2 * | 10/2011 | Pellecchia | 564/156 |
| 2003/0008924 | A1 | 1/2003 | Wang et al. | |
| 2004/0214902 | A1 * | 10/2004 | Wang et al. | 514/700 |
| 2005/0027000 | A1 | 2/2005 | Reed et al. | |
| 2006/0247305 | A1 | 11/2006 | Wang et al. | |
| 2007/0037865 | A1 | 2/2007 | Nunes et al. | |
| 2007/0149466 | A1 | 6/2007 | Milburn et al. | |
| 2009/0105319 | A1 | 4/2009 | Pellecchia et al. | |

FOREIGN PATENT DOCUMENTS

| WO | WO 02/40996 A2 | 5/2002 |
|---|---|---|
| WO | WO 2005/009434 | 6/2005 |
| WO | WO 2006/050447 A2 | 5/2006 |
| WO | WO 2006/125324 | 11/2006 |
| WO | WO 2009/052443 A1 | 4/2009 |

OTHER PUBLICATIONS

EP 10765133 Search Report dated Feb. 14, 2012.
PCT/US10/031113 International Search Report dated Jun. 17, 2010.
PCT/US10/031113 International Preliminary Report on Patentability and Written Opinion dated Oct. 18, 2011.
PCT/US08/080386 International Search Report dated Dec. 16, 2008.
PCT/US08/080386 International Preliminary Report on Patentability and Written Opinion dated Apr. 20, 2010.
Adams et al. Apogossypol and its degradation products. J. Am. Chem. Soc. 1938; 60: 2174-2180.
Arnold et al. Preclinical studies of Apogossypolone: a new nonpeptidic pan small molecule inhibitor of Bcl-2, Bcl-XL and Mcl-1 proteins in Follicular Small Cleaved Cell Lymphoma model. Molecular cancer. 2008; 7:20.
AU2008311827 Exam Report dated Nov. 19, 2013.
Becattini et al. Rational design and real time, in-cell detection of the proapoptotic activity of a novel compound targeting Bcl-X(L). Chemistry & biology. 2004; 11:389-395.
Benhaim et al. Induction of neutrophil Mac-1 integrin expression and superoxide production by the medicinal plant extract gossypol. Inflammation. 1994. 18(5):443-458.
Brunko et al. Studies leading to potent, dual inhibitors of Bcl-2 and Bcl xL. J. Med. Chem. 2007; 50:641-662.
Coward et al. Quantitative determination of Apogossypol, a proapoptotic analog of Gossypol, in mouse plasma using LC/MS/MS. Journal of pharmaceutical and biomedical analysis. 2006; 42:581-586.
CN200880120615.0 Office Action dated Nov. 2, 2012 (w/English Translation).
Dao et al. Synthesis and cytotoxicity of Gossypol related compounds. Eur J Med Chem. 2000; 35:805-813.

(Continued)

*Primary Examiner* — Sudhakar Katakam
(74) *Attorney, Agent, or Firm* — Wilson Sonsini Goodrich & Rosati

(57) ABSTRACT

Methods of using apogossypol and its derivatives for treating inflammation is disclosed. Also, there is described a group of compounds having structure A, or a pharmaceutically acceptable salt, hydrate, N-oxide, or solvate thereof are provided:

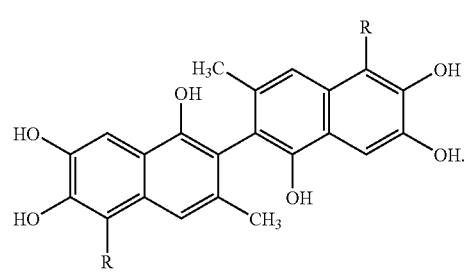

wherein each R is independently selected from the group consisting of H, C(O)X, C(O)NHX, NH(CO)X, $SO_2NHX$, and $NHSO_2X$, wherein X is selected from the group consisting of an alkyl, a substituted alkyl, an aryl, a substituted aryl, an alkylaryl, and a heterocycle. Compounds of group A may be used for treating various diseases or disorders, such as cancer.

5 Claims, 15 Drawing Sheets

(56) References Cited

OTHER PUBLICATIONS

Dodou. Investigations on gossypol: past and present developments. Expert Opinion on Investigational Drugs. 2005. 14(11):1419-1434.
Du et al. Synthesis of N-substituted indole derivatives via PIFA-mediated intramolecular cyclization. Org. Lett. 2006; 8:5919-5922.
Fitzpatrick et al. Anti-inflammatory effects of various drugs on acetic acid induced colitis in the rat. Agents and Actions. 1990. 30(3-4):393-402.
Hu et al. ApoG2, a novel inhibitor of antiapoptotic Bcl-2 family proteins, induces apoptosis and suppresses tumor growth in nasopharyngeal carcinoma xenografts. Int J Cancer. 2008; 123:2418-2429.
Islam et al. Structure-activity studies of antitumor agents based on pyrrolo[1,2-a]benzimidazoles: new reductive alkylating DNA cleaving agents. J Med Chem 1991; 34:2954-2961.
JP2010-530164 Office Action dated Sep. 26, 2013.
Kitada et al. Bcl-2 antagonist Apogossypol (NSC736630) displays single-agent activity in Bcl-2-transgenic mice and has superior efficacy with less toxicity compared with Gossypol (NSC19048). Blood. 2008; 3:3211-3249.
Kitada et al. Discovery, characterization, and structure-activity relationships studies of proapoptotic polyphenols targeting B-celllymphocyte/leukemia-2 proteins. Journal of medicinal chemistry. 2003; 46:4259-4264.
Li et al. A small molecule pan-Bcl-2 family inhibitor, GX15-070, induces apoptosis and enhances cisplatin-induced apoptosis in non-small cell lung cancer cells. Cancer Chemother Pharmacol. 2008; 61:525-534.
Lin et al. Effect of Apogossypolone on induction apoptosis in multiple myeloma cells and its mechanisms. Zhongguo shi yan xue ye xue za zhi I Zhongguo bing li sheng li xue hui = Journal of experimental hematology I Chinese Association of Pathophysiology 2009; 17: 92-98. (English Abstract).
Meltzer et al. Regioselective Route to Gossypol Analogues: The Synthesis of Gossypol and 5,5'-Didesisopropyl-5,5'-diethylgossypol. J. Org. Chem. 1985; 50:3121-3124.
Meng et al. Natural BH3 mimetic (−)-gossypol chemosensitizes human prostate cancer via Bcl-xL inhibition accompanied by increase of Puma and Noxa. Mol Cancer Ther. 2008; 7:2192-2202.
Mi et al. Synergistic antitumoral activity and induction of apoptosis by novel pan Bcl-2 proteins inhibitor Apogossypolone with adriamycin in human hepatocellular carcinoma. Acta Pharmacal. Sin. 2008; 29:1467-1477.
Mohammad et al. Preclinical studies of a nonpeptidic small-molecule inhibitor of Bcl-2 and Bcl-X(L) [(−) gossypol] against diffuse large cell lymphoma. Mol Cancer Ther. 2005; 4:13-21.
Oliver et al. (−)-Gossypol acts directly on the mitochondria to overcome Bcl-2- and Bcl-X(L)-mediated apoptosis resistance. Mol. Cancer Ther. 2005; 4:23-31.
Oltersdorf et al. An inhibitor of Bcl-2 family proteins induces regression of solid tumours. Nature. 2005; 435:677-681.
Rega et al. Structure-based discovery of a new class of Bcl-xL antagonists. Bioorg. Chem. 2007; 35:344-353.
Royer et al. Synthesis and anti-HIV activity of 1,1'-dideoxygossypol and related compounds. J. Med. Chem. 1995; 38:2427-2432.
Sakamoto et al. Probing substrate binding site of the *Escherichia coli*quinol oxidases using synthetic ubiquinol analogues. J. Biol. Chem. 1996; 271:29897-29902.
Shelley et al. Stereo-specific cytotoxic effects of Gossypol enantiomers and Gossypolone in tumour cell lines. Cancer letters. 1999; 135:171-180.
Shelley et al. Structure-activity studies on gossypol in tumor cell lines. Anti-Cancer Drugs. 2000. 11(3):209-216.
Shirley et al. Journal of Organic Chemistry. 1960. 25:1391-1394.
Sun et al. Apogossypolone inhibits cell growth by inducing cell cycle arrest in U937 cells. Oncology reports. 2009; 22:193-198.
Tang et al. Structure-based design of flavonoid compounds as a new class of small-molecule inhibitors of the anti-apoptotic Bcl-2 proteins. J. Med. Chem. 2007; 50:3163-3166.
Vermani et al. Herbal medicines for sexually transmitted diseases and AIDS. Journal of Ethnopharmacology. 2002. 80:49-66.
Wang et al. Structure-based design of potent small molecule inhibitors of anti-apoptotic Bcl-2 proteins. Journal of medicinal chemistry. 2006; 49:6139-6142.
Wei et al. Apogossypol derivatives as pan-active inhibitors of antiapoptotic B-cell lymphoma/leukemia-2 (Bcl-2) family proteins. J Med Chem. Jul. 23, 2009; 52(14):4511-4523.
Wei et al. Apogossypol derivatives as antagonists of antiapoptotic Bcl-2 family proteins. Mol Cancer Ther 2009; 8:904-913.
Wei et al. BI-97C1, an optically pure Apogossypol derivative as pan-active inhibitor of antiapoptotic B-cell lymphoma/leukemia-2 (Bcl-2) family proteins. J Med Chem. 2010; 53:4166-4176.
Wei et al. Synthesis and evaluation of Apogossypol atropisomers as potential Bcl-xL antagonists. Cancer Lett. 2009; 273:107-113.
Yamanoi et al. Direct and selective arylation of tertiary silanes with rhodium catalyst. J. Org. Chem. 2008; 73:6671-6678.
Zhang et al. Molecular mechanism of Gossypol-induced cell growth inhibition and cell death of HT-29 human colon carcinoma cells. Biochemical Pharmacology. 2003; 66:93-103.
White et al., "Antibody-targeted Immunotherapy for Treatment of Malignancy," *Annu. Rev. Med.* 52:125 (2001).
Pettinelli et al., "Adoptive transfer of experimental allergic encephalomyelitis in SJL/J mice after in vitro activation of lymph node cells by myelin basic protein: requirement for Lyt 1+2-T lymphocytes," *Journal of Immunology* 127:1420 (1981).
Rega et al., "Structure-based discovery of a new class of Bcl-xL antagonists", *Bioorg. Chem.*, 35(4);344-53 (2007), Epub May 21, 2007.
Yao et al., "Intra-articular injection of recombinant TRAIL induces synovial apoptosis and reduces inflammation in a rabbit knee model of arthritis", *Arthritis Res. Ther.*, 8(1), pp. 1-2 (2005).
Carter et al., Chemotherapy of Cancer, second edition, John Wiley & Sons, N.Y., N.Y., pp. 362-365 (1981).
West, A.R., Solid State Chemistry and its Applications, Wiley, New York, pp. 358 & 365 (1988).

\* cited by examiner

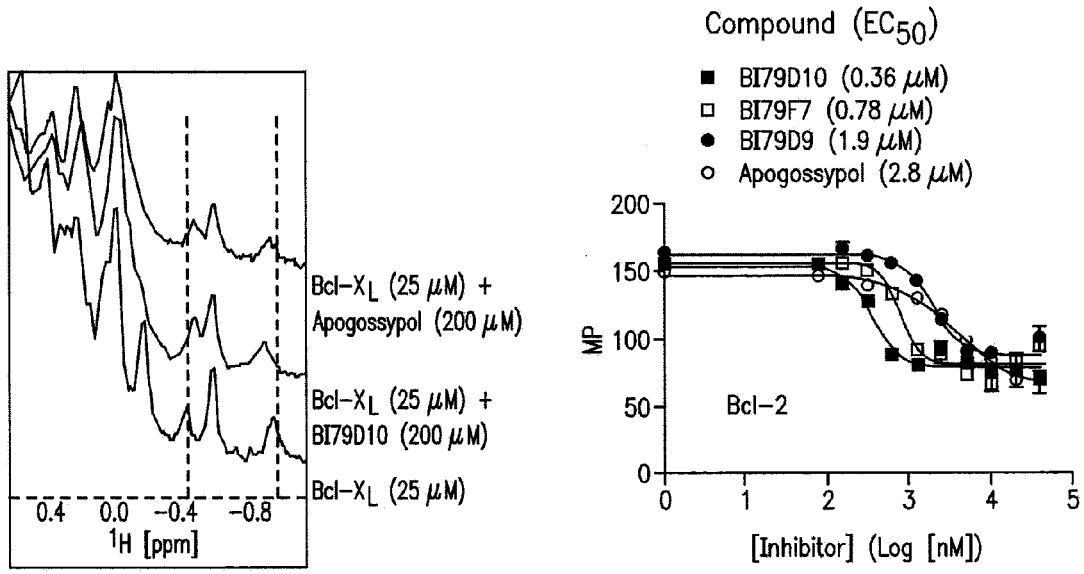
FIG. 2A
FIG. 2B
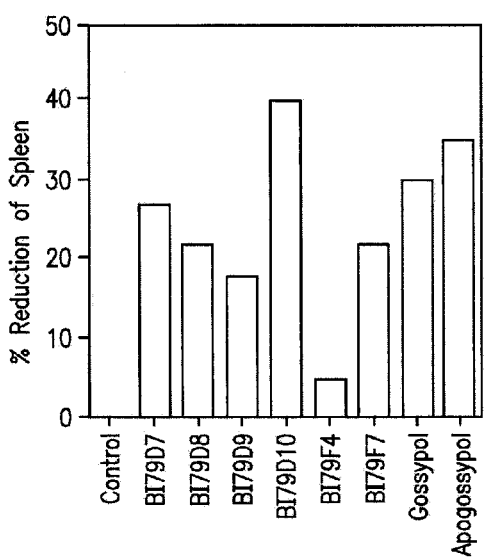
FIG. 3A
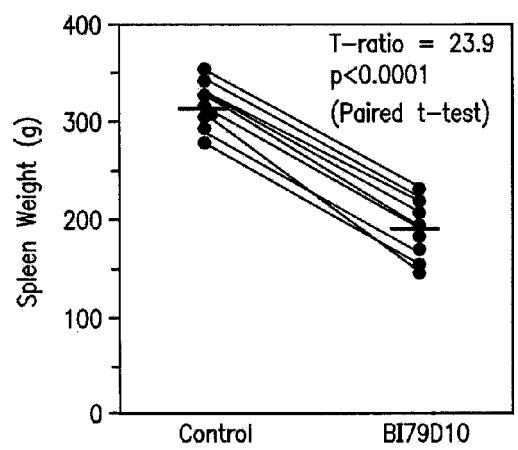
FIG. 3B

NAPHTHALENE-BASED INHIBITORS OF ANTI-APOPTOTIC PROTEINS

CROSS-REFERENCE TO RELATED APPLICATIONS

This application claims priority under 35 U.S.C. §119(e) to each of U.S. Patent Application Ser. No. 60/981,400 filed Oct. 19, 2007, U.S. Patent Application Ser. No. 61/035,969 filed Mar. 12, 2008, and U.S. Patent Application Ser. No. 61/097,171 filed Sep. 15, 2008, each of which is herein incorporated by reference in its entirety.

GRANT INFORMATION

This invention was made in part with government support under NIH (Grant U01 AI061139), and CSRA (Grant No. 08-02). The United States Government has certain rights in this invention.

BACKGROUND

1. Field of the Invention

The present invention relates generally to a class of compounds derived from naphthalene, such as apogossypol and derivatives thereof, for treating a variety of disorders, diseases and pathologic conditions, and more specifically, for treating cancer, autoimmune diseases, and/or inflammation.

2. Background Information

The apoptotic cascade in cells is known to lead to cell death. When anti-apoptotic proteins, such as BCL-2 family proteins, are overproduced by the cells, uncontrollable cell growth may ensue, potentially leading to the development of various serious diseases, disorders, and pathologies, particularly cancer.

Apoptosis plays a role in tissue homeostatis, for the physiological removal of unwanted cells during development and in host defense mechanism. The BCL-2 family of proteins are believed to be involved in regulating of apoptosis. Specifically, members of the BCL-2 gene family can act to inhibit programmed cell death (e.g., BCL-2, BCL-$X_L$, ced-9) or promote cell death (e.g., Bax, Bak, BCL-$X_S$). Pro-survival members of this family, such as BCL-$X_L$, contain, on the surface, a hydrophobic groove in which is believed to allow binding of the BH3 domain of the pro-apoptotic counterpart. This binding is believed to play role in apoptosis regulation, in fact pro- and anti-survival proteins can reverse each other function through dimerization.

Therefore, a need exists to inhibit anti-apoptotic proteins, such as the BCL-2 family proteins. Various potential BCL-2 antagonists have been previously identified. However, none of these compounds inhibits all six proteins in the BCL-2 family, i.e., all of the following proteins: BCL-$X_L$, BCL-2, BCL-W, BCL-B, BFL-1, and MCL-1. For example, none of the previously identified synthetic BCL-2 antagonists was effective at inhibiting the protein BFL-1. Therefore, the efficiency of such antagonists is not as high as desired. In addition, the existing antagonists are characterized by other drawbacks, such as insufficiency or safety issues.

As stated above, apoptosis is known to play a role in normal tissue homeostasis, thus ensuring a proper balance of cell production and cell loss. Defects in the regulation of programmed cell death may promote tumorgenesis, and also contribute to chemoresistance. Over-expression of anti-apoptotic BCL-2 family proteins occurs in many human cancers and leukemias, and therefore these proteins may be used as targets for the development of novel anticancer agents. Structural studies have elucidated a hydrophobic crevice on the surface of anti-apoptotic BCL-2 family proteins that binds the BH3 dimerization domain of pro-apoptotic family members. Thus, molecules that mimic the BH3 domain of pro-apoptotic proteins induce apoptosis and/or abrogate the ability of anti-apoptotic BCL-2 proteins to inhibit cancer cell death.

It has been previously shown that the natural product gossypol shown on FIG. 1A is an inhibitor of BCL-2, BCL-$X_L$ and MCL-1, functioning as a BH3 mimic. (–) Gossypol is currently in clinical trails, displaying single-agent antitumor activity in patients with advanced malignancies. Given that gossypol has toxicity problems likely due to two reactive aldehyde groups, we apogossypol (FIG. 1A), a compound that lacks these aldehydes, but retains activity against anti-apoptotic BCL-2 family proteins in vitro and in cells has been also evaluated previously. Recently, the efficacy and toxicity in mice of gossypol and apogossypol were compared. Pre-clinical in vivo data show that apogossypol has better efficacy and reduced toxicity compared to gossypol, as well as better single-dose pharmacokinetic characteristics, including, superior blood concentrations over time compared to gossypol, due to slower clearance. These observations indicate that apogossypol is a promising lead compound for cancer therapy.

BCL-2 family members are also believed to be involved in inflammatory disorders. For example, BCL-2 family members have been shown to play roles in neutrophil apoptosis and inflammatory accumulation. In several inflammatory diseases, the delay of neutrophil apoptosis is associated with reduced levels of the pro-apoptotic BCL-2 family member BAX. It has been also shown that eosinophils isolated from children with acute asthma had an increased expression of the anti-apoptotic protein BCL-2, which was inversely correlated with expiratory flow rate. BCL-2 family proteins are also associated with Crohn's disease. BAX expression is attenuated and BCL-$X_L$ expression is increased in T cells isolated from the lamina propria from patients with Crohn's disease. This shows that inflammatory cell survival, by means of pro-survival and anti-apoptotic signaling mechanisms, are involved in the pathogenesis of inflammatory diseases. Lupus is a complex systemic autoimmune disease, characterized by high levels of anti-DNA and anti-glomerular autoantibodies, activated B and T-cells, and glomerulonephritis. Neutrophils from lupus-susceptible mice display reduced rates of apoptosis. The decreased apoptosis is associated with the altered expression of BCL-2 family proteins contributing to the greater accumulation of neutrophils in the lupus-susceptible mice. Signaling studies using several different lupus strains indicate that multiple signaling pathways are upregulated in lymphocytes and non lymphocytes as disease evolves, including the activation of BCL-2 and BCL-$X_L$. These anti-apoptotic molecules are known to prolong the lifespan of all cells, including autoreactive B and T cells.

In view of the above drawbacks and deficiencies of existing BCL-2 inhibitors, new antagonists of anti-apoptotic proteins, such as BCL-2 family proteins, are desired. It is desirable that such new antagonists be safer and more effective than the existing compounds. Some of such compounds have been now identified (see FIG. 1 B)

SUMMARY

According to one embodiment of the invention, there are provided compounds having the structure A, or pharmaceutically acceptable salts, hydrates, N-oxides, or solvates thereof:

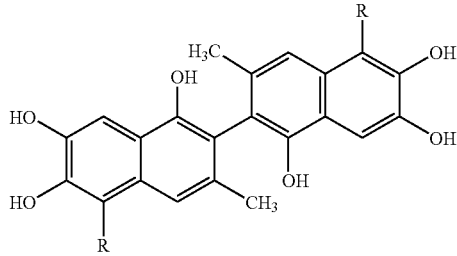

A wherein each R is independently selected from the group consisting of H, C(O)X, C(O)NHX, NH(CO)X, SO$_2$NHX, and NHSO$_2$X, wherein X is selected from the group consisting of an alkyl, a substituted alkyl, an aryl, a substituted aryl, an alkylaryl, and a heterocycle.

According to another embodiment of the present invention, there is provided a compound that is a species of the compounds having the structure A, the specific compound having the formula I:

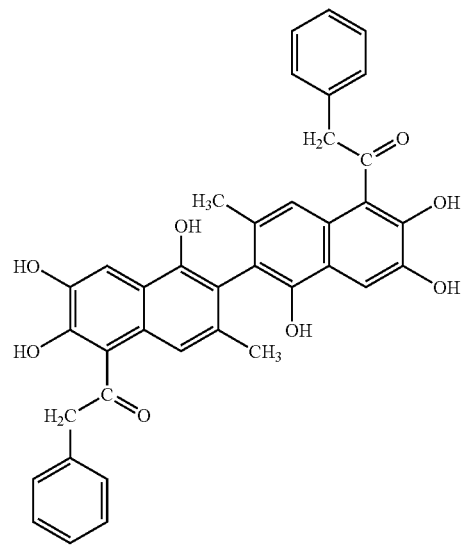

I

According to another embodiment of the present invention, a method for treating cancer or autoimmune diseases is provided, comprising administering to a subject in need thereof a therapeutically effective amount of the compounds having the structure A, including the species I, or pharmaceutically acceptable salts, hydrates, N-oxides, or solvates thereof.

The present invention is also directed to a method for treating inflammation. In particular, the invention relates to the use of apogossypol for the treatment of inflammation. Accordingly, a method for treating inflammation is disclosed. The method includes administering to a mammal a compound, in an amount effective to reduce inflammation, the compound having the structure B:

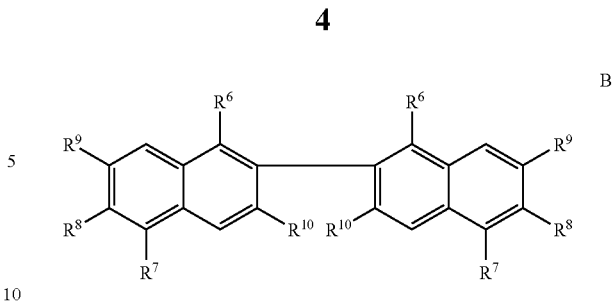

B wherein each of R$^6$, R$^8$, R$^9$ and R$^{10}$ is independently selected from the group consisting of hydrogen, hydroxyl, —(C$_1$-C$_6$) alkyl, —O(C$_1$-C$_6$)alkyl, —(C$_1$-C$_6$)alkylhalo, —OC(O)(C$_1$-C$_6$)alkyl, and halo, and each R$^7$ is independently selected from the group consisting of hydrogen, —(C$_1$-C$_6$)alkyl, —(C$_3$-C$_8$)cycloalkyl, —(C$_6$-C$_{10}$)aryl, and —(C$_1$-C$_6$)alkyl (C$_6$-C$_{10}$)aryl, C(O)X, C(O)NHX, NH(CO)X, SO$_2$NHX, and NHSO$_2$X, wherein X is selected from the group consisting of an alkyl, a substituted alkyl, an aryl, a substituted aryl, an alkylaryl, and a heterocycle or a pharmaceutically acceptable salt, hydrate, N-oxide, or solvate thereof. In some embodiments, the compound is used to treat inflammation is apogossypol, for example, (−) apogossypol that is substantially free of (+) apogossypol.

Also disclosed is a method of treating inflammation in a subject, comprising administering to the subject an anti-inflammatory agent selected from the group consisting of gossypol, apogossypol, L-apogossypol, derivatives of apogossypol, theaflavin, theaflavin-3'-gallate, theaflavanin, (−) gallocatechin-3-gallate (GCG), (−) epigallocatechin-3-gallate (EGCG), (−) catechin-3-gallate (CG), (−) epicatechin-3-gallate (ECG), derivatives of purpurogallin, and mixtures thereof.

In addition, a method for inducing apoptosis, modulating caspase activity, or inducing cell death in a mammal suffering from an inflammatory disease inflammation is disclosed. The method comprises contacting said mammal with a compound in the amount effective to induce apoptosis, modulate caspase activity, or induce cell death the target cells, the compound to be used having the structure B:

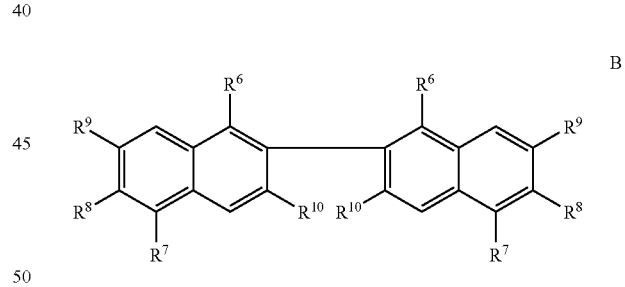

B wherein each of R$^6$, R$^8$, R$^9$ and R$^{10}$ is independently selected from the group consisting of hydrogen, hydroxyl, —(C$_1$-C$_6$) alkyl, —O(C$_1$-C$_6$)alkyl, —(C$_1$-C$_6$)alkylhalo, —OC(O)(C$_1$-C$_6$)alkyl, and halo, and each R$^7$ is independently selected from the group consisting of hydrogen, —(C$_1$-C$_6$)alkyl, —(C$_3$-C$_8$)cycloalkyl, —(C$_6$-C$_{10}$)aryl, and —(C$_1$-C$_6$)alkyl (C$_6$-C$_{10}$)aryl, C(O)X, C(O)NHX, NH(CO)X, SO$_2$NHX, and NHSO$_2$X, wherein X is selected from the group consisting of an alkyl, a substituted alkyl, an aryl, a substituted aryl, an alkylaryl, and a heterocycle, or a pharmaceutically acceptable salt, hydrate, N-oxide, or solvate thereof.

BRIEF DESCRIPTION OF FIGURES

FIG. 2 demonstrates, NMR binding studies (A) and inhibiting activity of some compounds of the present invention (B).

FIG. 3 demonstrates effectiveness of compounds of the present invention on shrinkage of BCL-2 mouse spleen.

DETAILED DESCRIPTION

Figure 1A:
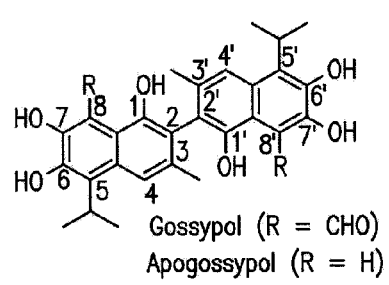
FIG. 1 demonstrates structures of gossypol and apogossypol (A), structure of a compound of the present invention (B); and molecular docking studies (C, D).

Unless otherwise defined, scientific and technical terms used in connection with the present invention shall have the meanings that are commonly understood by those of ordinary skill in the art. Further, unless otherwise required by context singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

The following terms, definitions and abbreviations further apply:

The term "patient" refers to organisms to be treated by the methods of the present invention. Such organisms include, but are not limited to, humans and other mammals. In the context of the invention, the term "subject" generally refers to an individual who will receive or who has received treatment described below (e.g., administration of the compounds of the invention, and optionally one or more additional therapeutic agents).

The term "BCL-2 family of proteins" refers to the family of proteins that currently includes at least the following six proteins: BCL-$X_L$, BCL-2, BCL-W, BCL-B, BFL-1, and MCL-1.

The term "halo" refers to fluoro, chloro, bromo, or iodo.

The terms "alkyl, alkoxy, alkenyl, alkynyl," etc. denote both straight and branched groups; but reference to an individual group such as "propyl" embraces only the straight chain group, a branched chain isomer such as "isopropyl" being specifically referred to.

"Aryl" denotes a phenyl group or an ortho-fused bicyclic carbocyclic group having about nine to ten ring atoms in which at least one ring is aromatic.

"Heteroaryl" encompasses a group attached via a ring carbon of a monocyclic aromatic ring containing five or six ring atoms consisting of carbon and one to four heteroatoms each selected from the group consisting of non-peroxide oxygen, sulfur, and N(X), where X is absent or is H, O, ($C_1$-$C_4$)alkyl, phenyl or benzyl, as well as a group of an ortho-fused bicyclic-heterocycle of about eight to ten ring atoms derived therefrom, particularly a benz-derivative or one derived by fusing a propylene, trimethylene, or tetramethylene digroup thereto.

More specifically, the term "alkyl" refers to a branched or unbranched saturated hydrocarbon group of 1 to 6 carbon atoms, such as methyl, ethyl, n-propyl, isopropyl, n-butyl, isobutyl, t-butyl, pentyl, and the like. Preferred alkyl groups herein contain one to 6 carbon atoms, such as, for example, methyl, ethyl, and the like.

As used herein the term "cycloalkyl" refers to a cyclic alkyl group of three to eight, preferably three, five or six, carbon atoms. The term "cycloalkylene" as used herein refers to a divalent cyclic alkylene group, typically a 3-, 5-, 6-, or 8-membered ring.

The term "alkoxy" as used herein refers to an alkyl group bound through a single, terminal ether linkage, i.e., an "alkoxy" group may be defined as —OR, where R is alkyl as defined above. A "lower alkoxy" group refers to an alkoxy group containing 1 to 6, carbon atoms.

The term "aryl" as used herein refers to an aromatic carbocyclic ring, typically 6- or 10-membered, wherein at least one ring is aromatic.

Specific values listed below for groups, substituents, and ranges, are for illustration only; they do not exclude other defined values or other values within defined ranges for the groups and substituents.

For example, "alkyl" can be methyl, ethyl, propyl, isopropyl, butyl isobutyl, sec-butyl, pentyl, 3-pentyl, or hexyl; cycloalkyl can be cyclopropyl, cyclobutyl, cyclopentyl, or cyclohexyl; "—O($C_1$-$C_6$)alkyl (alkoxy)" can be methoxy, ethoxy, propoxy, isopropoxy, butoxy, iso-butoxy, sec-butoxy, pentoxy, 3-pentoxy, or hexyloxy.

The term "prodrug" or "pro-drug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug, or may demonstrate increased palatability or be easier to formulate.

As used herein, the term "apogossypol" is a broad term which includes, without limitation, L-apogossypol, D-apogossypol, racemic apogossypol, S-apogossypol, R-apogossypol, (−) apogossypol and (+) apogossypol, and includes (−)apogossypol that is substantially free of (+)apogossypol.

Throughout the present disclosure, when a particular compound is mentioned by name, for example, apogossypol, it is understood that the scope of the present disclosure encompasses pharmaceutically acceptable salts, esters, amides, metabolites, or prodrugs of the named compound.

It will be appreciated by those skilled in the art that compounds of the invention having a chiral center may exist in and be isolated in optically active and racemic forms. Some compounds may exhibit polymorphism. It is to be understood that the present invention encompasses any racemic, optically active, polymorphic, or stereoisomeric form, or mixtures thereof, of a compound of the invention, which possesses the useful properties described herein. Also, if the named compound comprises a chiral center, the scope of the present disclosure also includes compositions comprising the racemic mixture of the two enantiomers, as well as compositions comprising each enantiomer individually, substantially free of the other enantiomer. Thus, for example, contemplated herein is a composition comprising the S enantiomer substantially free of the R enantiomer, or a composition comprising the R enantiomer substantially free of the S enantiomer.

By "substantially free" it is meant that the composition comprises less than 10%, or less than 8%, or less than 5%, or less than 3%, or less than 1% of the minor enantiomer. If the named compound comprises more than one chiral center, the scope of the present disclosure also includes compositions comprising a mixture of the various diastereomers, as well as compositions comprising each diastereomer substantially free of the other diastereomers. Thus, for example, commercially available apogossypol is a racemic mixture comprising two separate enantiomers. The recitation of "apogossypol" throughout this disclosure includes compositions that comprise the racemic mixture of apogossypol, compositions that comprise the (+) enantiomer substantially free of the (−) enantiomer, and compositions that comprise the (−) enantiomer substantially free of the (+) enantiomer.

It is well known in the art how to prepare optically active forms (for example, by resolution of the racemic form by recrystallization techniques, by synthesis from optically active starting materials, by chiral synthesis, or by chromatographic separation using a chiral stationary phase) and how to determine the anti cancer activity using the standard tests described herein, or using other similar tests which are well known in the art.

The term "pharmaceutical composition" refers to a mixture of a compound with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "pharmaceutically acceptable salt" refers to a formulation of a compound that does not cause significant irritation to an organism to which it is administered and does not abrogate the biological activity and properties of the compound. Pharmaceutical salts can be obtained by reacting a compound of the invention with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutical salts can also be obtained by reacting a compound of the invention with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts thereof with amino acids such as arginine, lysine, and the like.

"Inflammation" as used herein is a general term for the local accumulation of fluid, plasma proteins, and white blood cells that is initiated by physical injury, infection, or a local immune response. Many different forms of inflammation are associated with different diseases. "Inflammation-associated" diseases include, for example, lupus, psoriasis, rheumatoid arthritis, and inflammatory bowel disease. Other inflammation-associated diseases are discussed herein.

As used herein, the terms "anti-inflammatory agent" refers to any anti-inflammatory compounds that are used in the treatment of inflammation.

"Treatment," as used herein, pertains to the therapeutic administration of the compounds of the invention for the prevention, amelioration, or cure of disease.

The term "pharmaceutical agent or drug" as used herein refers to a chemical compound or composition capable of inducing a desired therapeutic effect when properly administered to a patient.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, for example, more than about 85%, 90%, 95%, and 99%. The object species may be also purified to essential homogeneity (contaminant species cannot be detected in the composition by conventional detection methods), wherein the composition consists essentially of a single species.

According to one embodiment of the invention, there are provided compound having the structure A, or a pharmaceutically acceptable salt, hydrate, N-oxide, or solvate thereof:

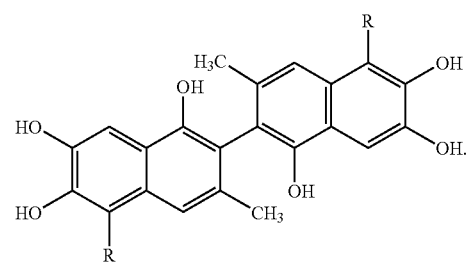

A wherein each R is independently selected from the group consisting of H, C(O)X, C(O)NHX, NH(CO)X, SO$_2$NHX, and NHSO$_2$X, wherein X is selected from the group consisting of an alkyl, a substituted alkyl, an aryl, a substituted aryl, an alkylaryl, and a heterocycle.

According to other embodiment of the invention, there are provided specific compounds encompassed by the structure A, or pharmaceutically acceptable salts, hydrates, N-oxides, or solvates thereof, where the specific compounds are compounds I-XXII:

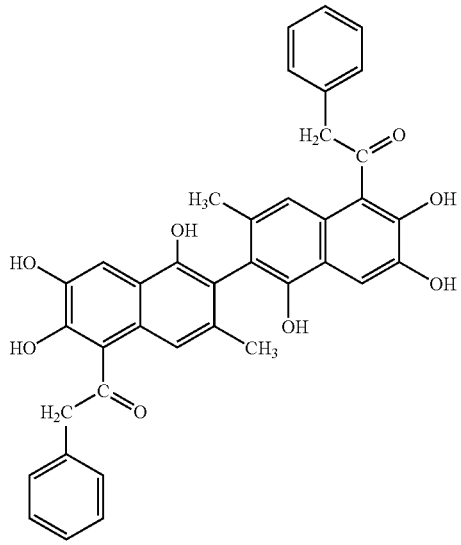

I

-continued
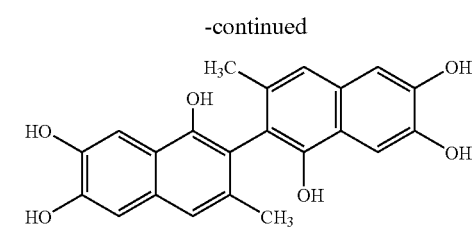
II
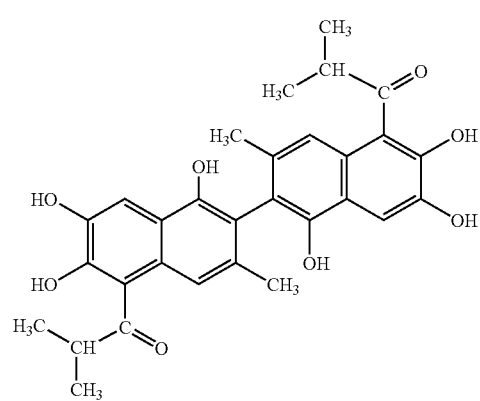
III
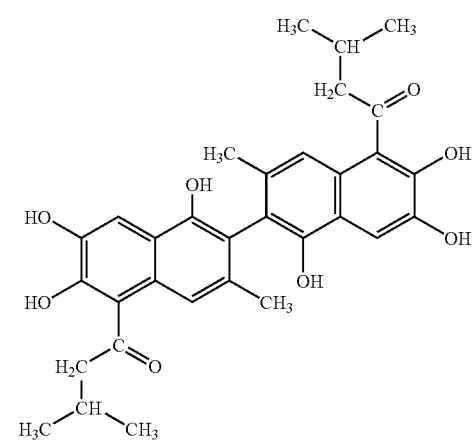
IV
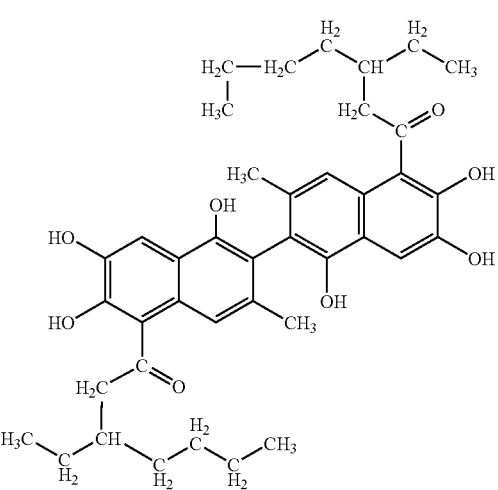
V
-continued
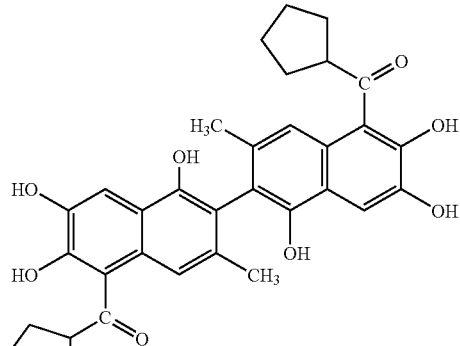
VI
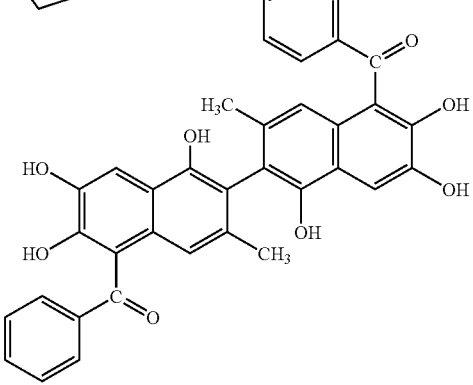
VII
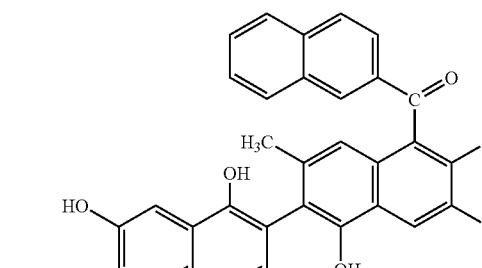
VIII
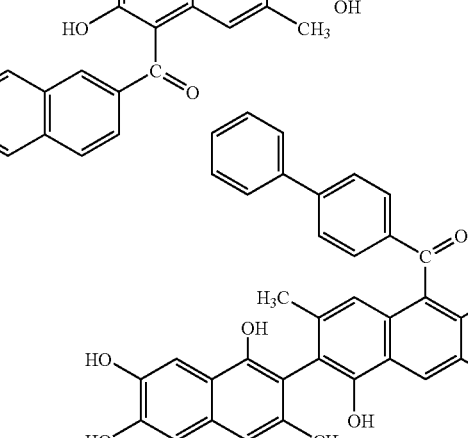
IX
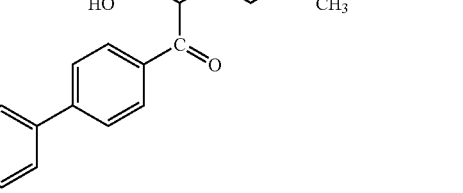

X
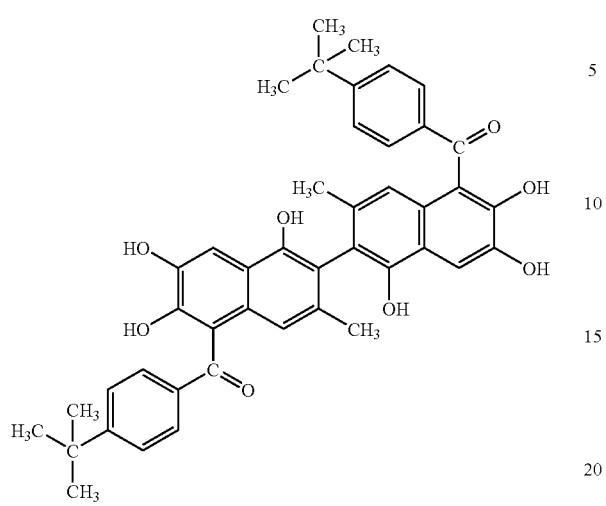
XI
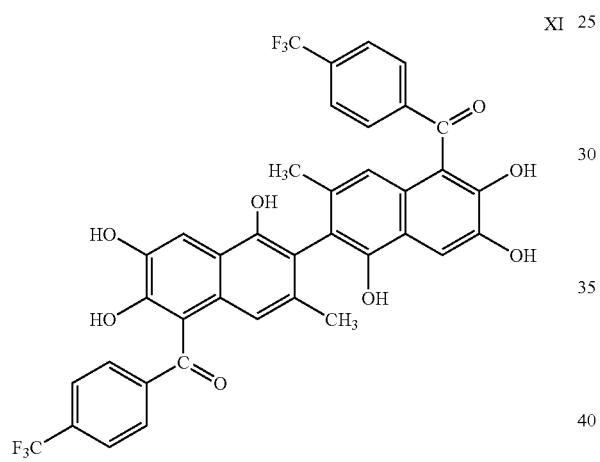
XII
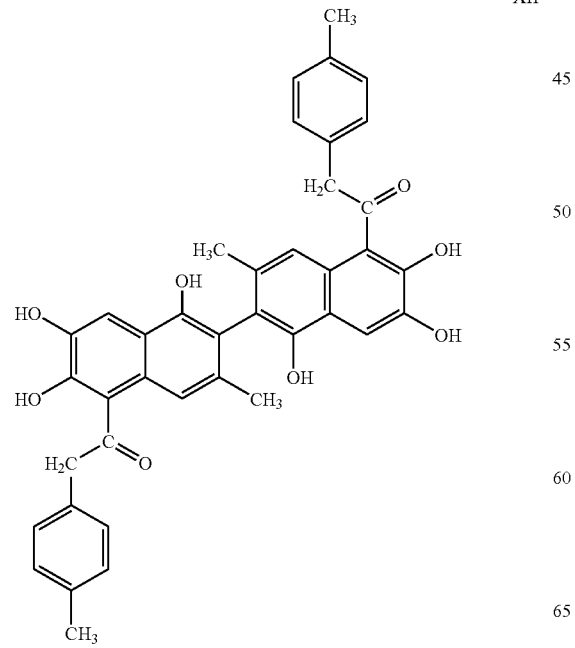
XIII
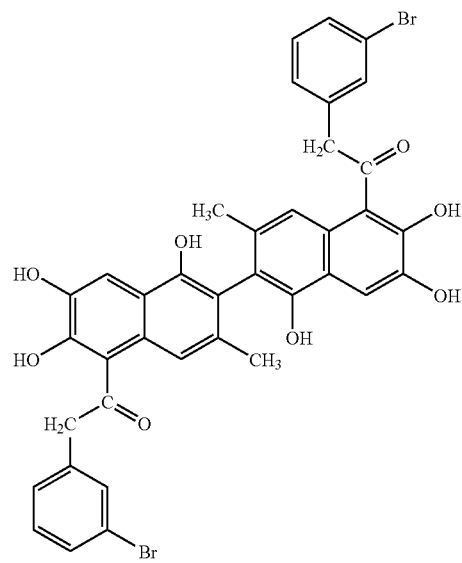
XIV
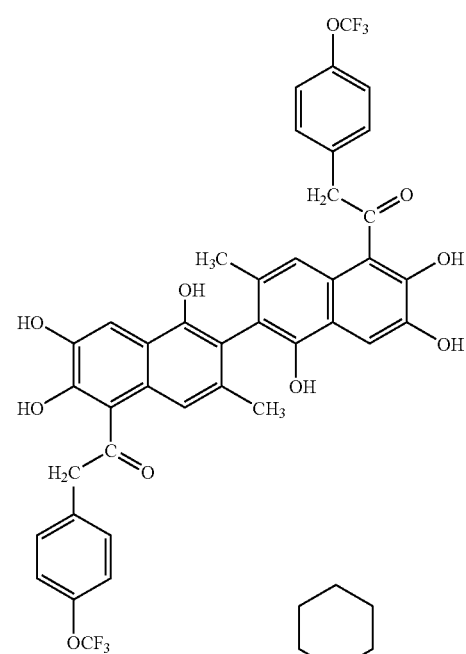
XV
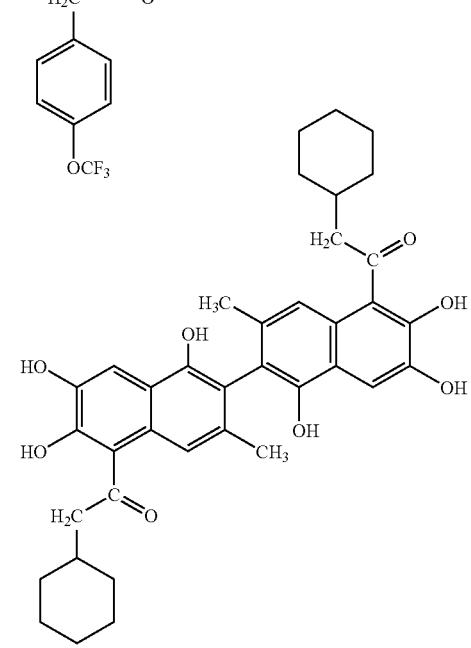

-continued
XVI
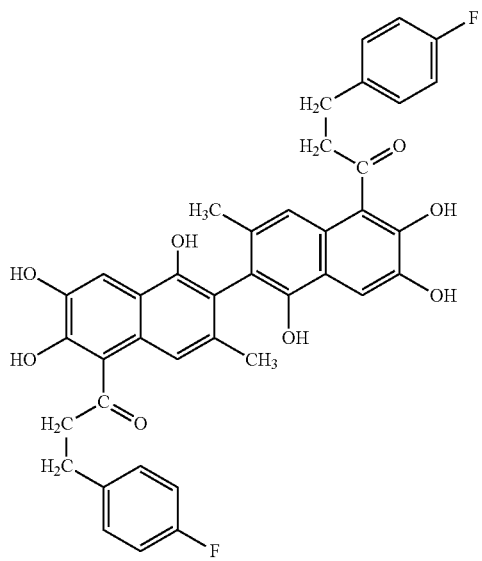
XVII
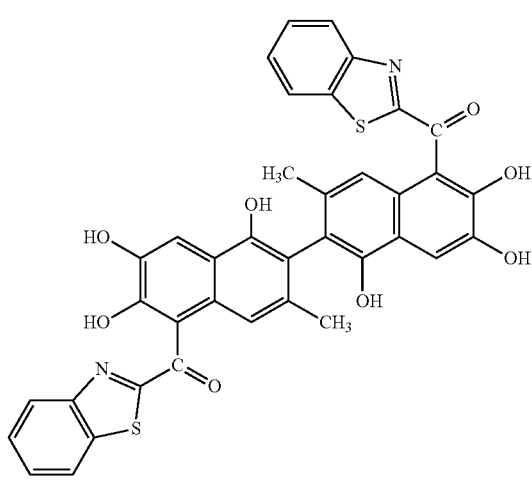
XVIII
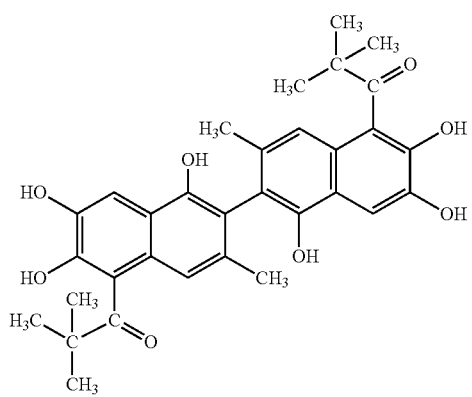
-continued
XIX
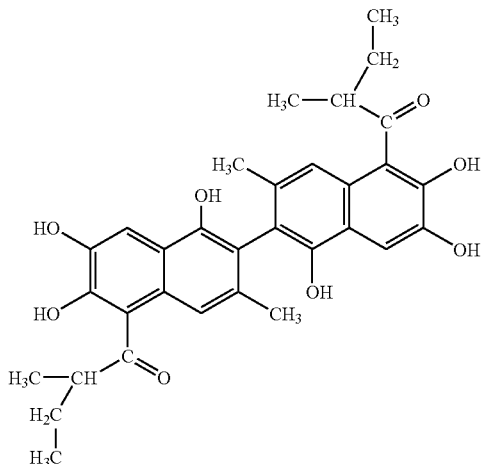
XX
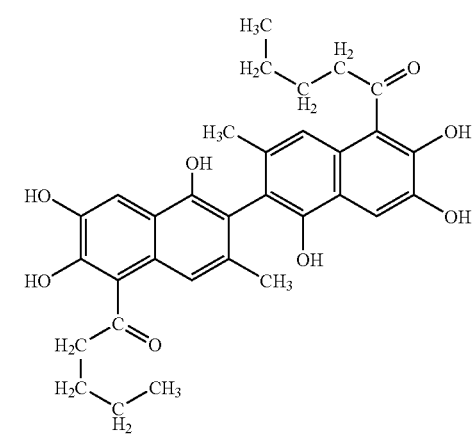
XXI
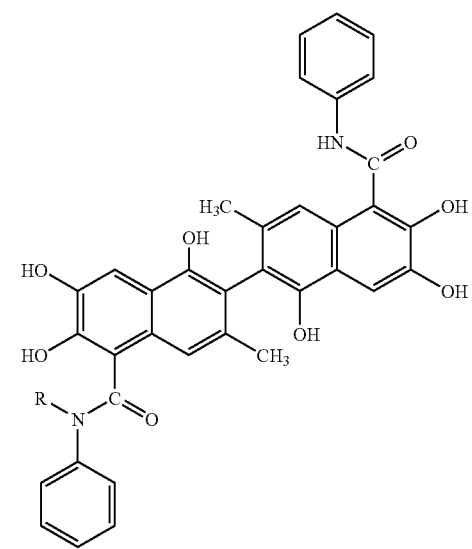

XXII

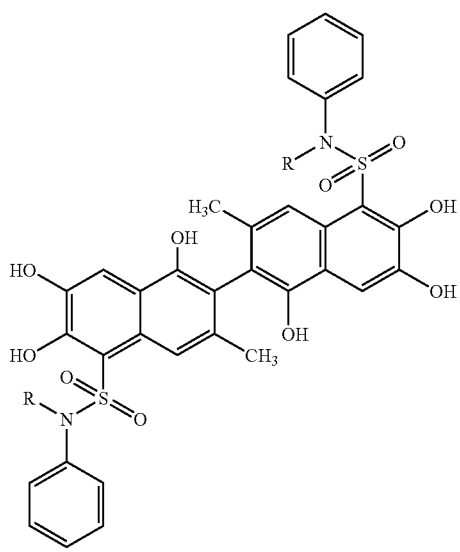

According to other embodiments, a method is provided for treating a disease or disorder. The method can include administering to a subject in need of such treatment, an effective amount of any above-described compound, or pharmaceutically acceptable salts, hydrates, or solvates thereof. Non-limiting examples of the diseases or disorders that can be treated are cancer and autoimmune diseases.

According to another embodiment, a method is provided for treating cancer. The method comprises administering to a subject in need thereof a therapeutically effective amount of any above-described compound, or pharmaceutically acceptable salts, hydrates, or solvates thereof. Any above-described compound may be used for treating any type of cancer. In some aspects, the kinds of cancer that may be treated include lung cancer, breast cancer, prostate cancer, as well as a variety of lymphomas.

According to another embodiment, any above-described compound can be used for the manufacture of a medicament for the treatment of a pathological condition or symptom in a mammal, such as a human. The medicament can be directed to the treatment of cancer, within the limitations described above.

According to another embodiment, pharmaceutical compositions are provided, the pharmaceutical compositions comprising any above-described compound, or pharmaceutically acceptable salts, hydrates, or solvates thereof, and a pharmaceutically acceptable diluent or carrier. The pharmaceutical compositions can be used to treat cancer. The pharmaceutical compositions can further optionally include one or more additional therapeutic anti-cancer agents, including, but not limited to, such agents as (1) alkaloids, including, microtubule inhibitors (e.g., Vincristine, Vinblastine, and Vindesine, etc.), microtubule stabilizers (e.g., Paclitaxel [Taxol], and Docetaxel, Taxotere, etc.), and chromatin function inhibitors, including, topoisomerase inhibitors, such as, epipodophyllotoxins (e.g., Etoposide [VP-16], and Teniposide [VM-26], etc.), and agents that target topoisomerase I (e.g., Camptothecin and Isirinotecan [CPT-11], etc.); (2) covalent DNA-binding agents [alkylating agents], including, nitrogen mustards (e.g., Mechlorethamine, Chlorambucil, Cyclophosphamide, Ifosphamide, and Busulfan [Myleran], etc.), nitrosoureas (e.g., Carmustine, Lomustine, and Semustine, etc.), and other alkylating agents (e.g., Dacarbazine, Hydroxymethylmelamine, Thiotepa, and Mitocycin, etc.), (3) noncovalent DNA-binding agents [antitumor antibiotics], including, nucleic acid inhibitors (e.g., Dactinomycin [Actinomycin D], etc.), anthracyclines (e.g., Daunorubicin [Daunomycin, and Cerubidine], Doxorubicin [Adriamycin], and Idarubicin [Idamycin], etc.), anthracenediones (e.g., anthracycline analogues, such as, [Nitoxantrone], etc.), bleomycins (Blenoxane), etc., and plicamycin (Mithramycin), etc.; (4) antimetabolites, including, antifolates (e.g., Methotrexate, Folex, and Mexate, etc.), purine antimetabolites (e.g., 6-Mercaptopurine [6-MP, Purinethol], 6-Thioguanine [6-TG], Azathioprine, Acyclovir, Ganciclovir, Chlorodeoxyadenosine, 2-Chlorodeoxyadenosine [CdA], and 2'-Deoxycoformycin [Pentostatin], etc.), pyrimidine antagonists (e.g., fluoropyrimidines [e.g., 5-fluorouracil (Adrucil), 5-fluorodeoxyuridine (FdUrd) (Floxuridine)] etc.), and cytosine arabinosides (e.g., Cytosar [ara-C] and Fludarabine, etc.); (5) enzymes, including, L-asparaginase, and hydroxyurea, etc.; (6) hormones, including, glucocorticoids, such as, antiestrogens (e.g., Tamoxifen, etc.), nonsteroidal antiandrogens (e.g., Flutamide, etc.), and aromatase inhibitors (e.g., anastrozole [Arimidex], etc.); (7) platinum compounds (e.g., Cisplatin and Carboplatin, etc.); (8) monoclonal antibodies conjugated with anticancer drugs, toxins, and/or radionuclides, etc.; (9) biological response modifiers (e.g., interferons [e.g., IFN-.alpha., etc.] and interleukins [e.g., IL-2, etc.], etc.); (10) adoptive immunotherapy; (11) hematopoietic growth factors; (12) agents that induce tumor cell differentiation (e.g., all-trans-retinoic acid, etc.); (13) gene therapy agents; 14) antisense therapy agents; (15) tumor vaccines; (16) agents directed against tumor metastases (e.g., Batimistat, etc.); (17) inhibitors of angiogenesis, and (18) selective serotonin reuptake inhibitors (SSRI's).

Representative, but non-limiting examples of suitable SSRIs that may be used include sertraline (e.g., sertraline hydrochloride, marketed under the trademark "Zoloft®" by Pfizer, Inc.) or sertraline metabolite, fluvoxamine (e.g., fluvoxamine melate, marketed under the trademark "Luvox®" by Solvay Pharmaceuticals, Inc.), paroxetine (e.g., paroxetine hydrochloride, marketed under the trademark "Paxil®" by SmithKline Beecham Pharmaceuticals, Inc.), fluoxetine (e.g., fluoxetine hydrochloride, marketed under the trademarks "Prozac®" or "Sarafem®" by Eli Lilly and Company) and citalopram (e.g., citalopram hydrobromide, marketed under the trademark "Celexa®" by Forest Laboratories, Parke-Davis, Inc.), and metabolites thereof. Additional examples include venlafaxine (e.g., venlafaxine hydrochloride marketed under the trademark "Effexor®" by Wyeth-Ayerst Laboratories), mirtazapine (e.g., marketed under the trademark "Remeron®" by Organon, Inc.), buspirone (e.g., buspirone hydrochloride marketed under the trademark "Buspar®" by Bristol-Myers Squibb), trazodone (e.g., trazodone hydrochloride marketed under the trademark "Desyrel®" by Bristol-Myers Squibb and Apothecon), nefazadone (e.g., nefazodone hydrochloride marketed under the trademark "Serzon®" by Bristol-Myers Squibb), clomipramine (e.g., clomipramine hydrochloride marketed under the trademark "Anafranil®" by Novopharm, LTD, Ciba, and Taro Pharmaceuticals), imipramine (e.g., imipramine hydrochloride marketed under the trademark "Tofranil®" by Glaxo-Welcome, Inc.), nortriptyline (e.g., Nortiptyline hydrochloride marketed under the trademark "Nortrinel®" by Lundbeck), mianserine (e.g., marketed under the trademark "Tolvon®" by Organon, Inc.), duloxetine (e.g., duloxetine hydrochloride marketed by Eli Lilly and Company), dapoxetine (e.g., dapoxetine hydrochloride marketed by ALZA Corporation), litoxetine (e.g., litoxetine hydrochloride marketed by Synthelabo Recherche (L.E.R.S.), Bagneux, France), femoxetine, lofepramine (e.g., marketed under the trademark "Gamonil®" by MERCK & Co., Inc.), tomoxetine (e.g., marketed by Eli Lilly and Company). The present invention encompasses SSRIs that are currently used, or those later discovered or formulated. SSRIs, including those listed above, may be administered orally in an amount between about 2 mg and about 2,500 mg daily.

In the broad sense, any cancer or tumor (e.g. hematologic and solid tumors) may be treated according to embodiments of the invention. Exemplary cancers that may be treated according to embodiments of the invention include, but are not limited to, head and neck cancer, brain cancer (e.g. glioblastoma multifoma) breast cancer, colorectal cancer, esophageal cancer, gastric cancer, hepatic cancer, bladder cancer, cervical cancer, endometrial cancer, lung cancer (non-small cell), ovarian cancer and other gynological cancers (e.g. tumors of the uterus and cervix), pancreatic cancer, prostate cancer, renal cancer, choriocarcinoma (lung cancer), skin cancer (e.g. melanoma, basal cell carcinoma), hairy cell leukemia, chronic lymphotic leukemia, acute lymphocytic leukemia (breast & bladder), acute myelogenous leukemia, meningeal leukemia, chronic myelogenous leukemia, and erythroleukemia. More commonly, the cancers treated include leukemia and B-cell cancers (e.g. lymphoma, multiple myeloma, and MDS.

Non-limiting examples of autoimmune diseases that can be treated using any above-described compound and methods of the present invention include rheumatoid arthritis, psoriatic arthritis, juvenile idiopathic arthritis, multiple sclerosis, systemic lupus erythematosus, myasthenia gravis, juvenile onset diabetes, glomerulonephritis, autoimmune thyroiditis, Behcet's disease, Crohn's disease, ulcerative colitis, bullous pemphigoid, sarcoidosis, psoriasis, ichthyosis, Graves ophthalmopathy, psoriasis, psoriasis inflammatory bowel disease, and asthma.

As discussed in more detail below, some embodiments also provide methods for treating and/or prevention various inflammatory disorders, diseases and conditions. Such inflammatory disorders, diseases and conditions include, without limitation, systemic autoimmune diseases such as, for example, lupus erythematosus, rheumatoid arthritis, multiple sclerosis, and psoriasis; and organ specific autoimmune diseases such as, for example, ulcerative colitis, myasthenia gravis, Grave's disease, Hashimoto's thyroiditis, Crohn's disease, lupus nephritis, autoimmune hemolytic anemias, immune thrombocytopenic purpura (ITP), thrombotic thrombocytopenic purpura (TTP), insulin dependent diabetes mellitus, glomerulonephritis, and rheumatic fever. Other inflammatory diseases that may be treated in accordance with this invention include, without limitation, other inflammatory arthritic conditions such as psoriatic arthritis, osteoarthitis and gouty arthritis, as well as other inflammatory conditions such as conjunctivitis, dermatitis, bronchitis, rhinitis etc., brought about by injury, allergies, infections, microorganisms, trauma, or physical or chemical agents. The treatment of inflammatory aspects of asthma, Sjogrens' syndrome, meningitis, adrenoleukodystrophy, CNS vasculitis, mitochondrial myopathies, Amyotrophic Lateral Sclerosis, Alzheimer's disease, or tumors is also contemplated as part of this invention. Examples of mitochondrial myopathies include MELAS syndrome, MERF syndrome, Leber's disease, Wernicke's encephalopathy, Rett syndrome, homocystinuria, hyperprolinemia, nonketotic hyperglycinemia, hydroxybutyric aminoaciduria, sulfite oxidase deficiency, and combined systems disease (B12 deficiency). In association with such prevention and/or treatment, articles of manufacture, compositions, methods of use, and medical treatments comprising the compounds described herein are also provided.

In some cases, it may be appropriate to administer any above-described compound as a salt. Examples of pharmaceutically acceptable salts include organic acid addition salts formed with acids which form a physiological acceptable anion, for example, tosylate, methanesulfonate, acetate, citrate, malonate, tartarate, succinate, benzoate, ascorbate, ketoglutarate, and glycerophosphate. Suitable inorganic salts may also be formed, including hydrochloride, sulfate, nitrate, bicarbonate, and carbonate salts. Pharmaceutically acceptable salts may be obtained using standard procedures well known in the art, for example by reacting any above-described compound with a suitable base affording a physiologically acceptable anion. Alkali metal (for example, sodium, potassium or lithium) or alkaline earth metal (for example calcium) salts of carboxylic acids can also be made.

Any tablets, troches, pills, capsules, and the like, which incorporate any above-described compound, may also contain binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When there is a unit dosage form of any above-described compound, it may contain, in addition to materials of the above type, a liquid carrier, such as a vegetable oil or a polyethylene glycol. Various other materials may be present as coatings or to otherwise modify the physical form of a solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Any material used in preparing any unit dosage form should be pharmaceutically acceptable and substantially non-toxic in the amounts employed. In addition, any above-described compound may be incorporated into sustained-release preparations and devices.

Any above-described compound may also be administered intravenously or intraperitoneally by infusion or injection. Solutions of any above-described compound may be prepared in water, optionally mixed with a nontoxic surfactant. Dispersions may also be prepared in glycerol, liquid polyethylene glycols, triacetin, and mixtures thereof and in oils. Under ordinary conditions of storage and use, these preparations may contain a preservative to prevent the growth of microorganisms.

Sterile injectable solutions can be prepared by incorporating any above-described compound of in the sufficient therapeutic amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, any above-described compound may be applied in pure form, i.e., when it is a liquid. However, it will generally be desirable to administer it to the skin as compositions or formulations, in combination with a dermatologically acceptable carrier, which may be a solid or a liquid. Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants and additional antimicrobial agents can be added to optimize the properties for a given use.

The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user, as known to those having ordinary skill in the art.

As mentioned above, inflammation disorders may involve the activity of apoptotic regulators. Thus, it is desirable to identify compounds that modulate the activity of apoptotic regulators, such as BCL-2 proteins. Such compounds are described below. In some embodiments, the binding of these compounds prevents the interaction of anti-apoptotic BCL-2 family members with pro-apoptotic BCL-2 family members, and thereby reduces the biological activity of anti-apoptotic BCL-2 family members. As a result, the compounds can be used to treat or prevent inflammatory disorders involving anti-apoptotic BCL-2 protein activity. In various embodiments, the compounds of interest comprise apogossypol, including (−) apogossypol substantially free of (+) apogossypol, as well as various derivatives of apogossypol and other related compounds described below. Such compounds can be administered to a patient with a high susceptibility to developing a condition associated with inflammation, for example, lupus erythematosus, to reduce the likelihood that the patient will develop such conditions.

As shown below apogossypol is more efficacious than gossypol, yet less toxic. The aldehydes in gossypol make it compound reactive, thus effectively reducing the available concentrations of active drug and causing toxicity. Apogossypol, a gossypol analog without the problematic aldehydes, retains full activity against anti-apoptotic BCL-2-family proteins. Daily dosing studies, described in more detail below in the Examples portion of the application, show that mice tolerate doses of apogossypol about 24-times higher than gossypol. Furthermore, the studies show that apogossypol is superior to parent compound gossypol with respect to toxicology and efficacy.

More specifically, according to embodiments of the present invention, compounds useful for treating and/or preventing inflammatory disorders, diseases, and conditions include compounds having the structure B:

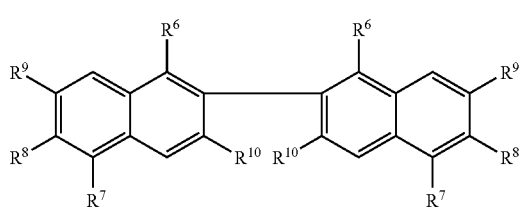

wherein each of $R^6$, $R^8$, $R^9$ and $R^{10}$ is independently selected from the group consisting of hydrogen, hydroxyl, —($C_1$-$C_6$) alkyl, —O($C_1$-$C_6$)alkyl, —($C_1$-$C_6$)alkylhalo, —OC(O)($C_1$- $C_6$)alkyl, and halo, and each $R^7$ is independently selected from the group consisting of hydrogen, —($C_1$-$C_6$)alkyl, —($C_3$-$C_8$)cycloalkyl, —($C_6$-$C_{10}$)-aryl, and —($C_1$-$C_6$)alkyl ($C_6$-$C_{10}$)aryl, C(O)X, C(O)NHX, NH(CO)X, $SO_2$NHX, and $NHSO_2$X, wherein X is selected from the group consisting of an alkyl, a substituted alkyl, an aryl, a substituted aryl, an alkylaryl, and a heterocycle, or a pharmaceutically acceptable salt, hydrate, N-oxide, or solvate thereof.

In the general structure B shown above, some specific $R^6$, $R^8$, $R^9$ and $R^{10}$ groups that may be used include, independently, hydrogen, —OH, —$OCH_3$, —$CF_3$, —$CH_3$, —$OC_2H_5$, —$OC(O)CH_3$, F, Cl, or Br. Some specific $R^7$ groups that may be used include, independently, hydrogen, —$C_2H_5$; i-Pr, n-Pr, n-Bu, t-Bu, i-Bu, s-Bu, or cyclohexyl.

In some embodiments the compound of the general structure B shown above is apogossypol. The use of apogossypol for treating cancer is described in PCT Publication No. WO 2005/009434, filed Jun. 25, 2005, which is hereby incorporated by reference in its entirety.

One specific compound of the invention described the general structure B shown above has each of $R^6$, $R^8$, $R^9$ as the acetate moiety —$OC(O)CH_3$), has $R^7$ as i-Pr, and $R^{10}$ as —$CH_3$ (apogossypol hexacetate). This compound can also be used as pro-drug for oral administration of apogossypol. In another embodiment the compounds of the invention include compounds of formula B, where one of the $R^6$ groups is a group other than hydrogen. In one embodiment, the compound can be (−) apogossypol. In other embodiments, the compound can be (−) apogossypol, (+) apogossypol, racemic apogossypol, S-apogossypol, R-apogossypol, or mixtures thereof. In another embodiment, the compound is substantially pure (−)apogossypol. In some embodiments, (−) apogossypol is at least 80 percent of all macromolecular species present in the composition, such as more than about 85%, 90%, 95%, and 99%. For example, (−) apogossypol may be purified to essential homogeneity, where the composition consists essentially of solely (−) apogossypol. In various embodiments, the compound is (−) apogossypol is substantially free of (+) apogossypol. In some embodiments the compound of the general structure B shown above is compound XXI or XXII shown above.

In one embodiment, the compound the general structure B shown above contains about 50% or more by weight of the (−) enantiomer of apogossypol and about 50% or less by weight of (+) enantiomer of apogossypol. In certain embodiments, the compound contains about 60% or more by weight of the (−) enantiomer of apogossypol and about 40% or less by weight of (+) enantiomer of apogossypol. In some embodiments, the compound contains about 70% or more by weight of the (−) enantiomer of apogossypol and about 30% or less by weight of (+) enantiomer of apogossypol. In some embodiments, the compound contains about 80% or more by weight of the (−) enantiomer of apogossypol and about 20% or less by weight of (+) enantiomer of apogossypol. In some embodiments, the compound contains about 90% or more by weight of the (−) enantiomer of apogossypol and about 10% or less by weight of the (+) enantiomer of apogossypol. In some embodiments, the compound contains about 95% or more by weight of the (−) enantiomer of apogossypol and about 5% or less by weight of (+) enantiomer of apogossypol. In some embodiments, apogossypol contains about 99% or more by weight of the (−) enantiomer of apogossypol and about 1% or less by weight of (+) enantiomer of apogossypol.

Binding of the compounds disclosed herein to anti-apoptotic BCL-2 proteins can induce apoptosis and thereby treat inflammation and/or inflammatory disorders. In some embodiments, the compounds disclosed herein can bind to anti-apoptotic BCL-2 family proteins such as, for example, BCL-2 or BCL-X$_L$. This binding can inhibit binding of the anti-apoptotic BCL-2 family members to pro-apoptotic BCL-2 family members. In various embodiments, binding of the compounds disclosed herein can reduce the formation of complexes between anti-apoptotic BCL-2 proteins and the BH3 domain of pro-apoptotic BCL-2 family members.

The invention also provides a pharmaceutical composition comprising the compounds described herein, or a pharmaceutically acceptable salt thereof in combination with a pharmaceutically acceptable diluent or carrier. Further, the invention provides the use of compounds disclosed herein in combination with other known anti-inflammatory compounds.

In various embodiments, the invention provides a method for treating inflammatory disease and/or a condition associated with inflammation comprising administering to a mammal in need of such therapy, an effective amount of the compounds described herein, the compounds described herein in combination with an additional anti-inflammatory compound or a pharmaceutically acceptable salt thereof. In other embodiments, methods for the prevention of inflammatory disease and/or a condition associated with inflammation or a method for reducing the likelihood that a patient will develop such inflammation is provided. The methods can include administering to a mammal in need of such therapy, an effective amount of the compounds described herein or a pharmaceutically acceptable salt thereof.

There are also provided methods for treating a mammalian subject, particularly a human, suspected of having, or being prone to a disease or condition involving inflammation, comprising administering to a mammalian subject in need thereof a therapeutically effective amount of a compound comprising at least one of the compounds of the general structure B shown above, a single enantiomer of a compound of the general structure B, a mixture of the (+) enantiomer and the (−) enantiomer, a mixture of about 90% or more by weight of the (−) enantiomer and about 10% or less by weight of the (+) enantiomer, an individual diastereomer of a compound of the general structure B, a mixture of diastereomers, or a pharmaceutically acceptable salt, solvate, or prodrug thereof, so as to affect treat or prevent inflammation. In some embodiments, the compound is apogossypol.

In some embodiments, the present methods for treating inflammation or preventing inflammation include administration of an effective amount of another therapeutic agent useful for treating or preventing the diseases or disorders disclosed herein. In some embodiments, the time in which the therapeutic effect of the other therapeutic agent is exerted overlaps with the time in which the therapeutic effect of the apogossypol or derivative is exerted.

In some embodiments, the other therapeutic agent is an anti-inflammatory agent. Examples of anti-inflammatory agents suitable for use according to some embodiments disclosed herein include, but are not limited to, steroids (e.g., cortisol, cortisone, fludrocortisone, prednisone, methylprednisolone, 6-methylprednisone, triamcinolone, betamethasone or dexamethasone), nonsteroidal anti-inflammatory drugs (NSAIDS (e.g., aspirin, acetaminophen, tolmetin, salicylates, ibuprofen, mefenamic acid, piroxicam, nabumetone, rofecoxib, celecoxib, etodolac or nimesulide). For the treatment of lupus erythmatosus, for example, the compounds disclosed herein may also be administered in conjunction with anti-malarial drugs including, for example, hydroxychloroquinone or in conjunction with cytotoxic chemotherapies including, for example, azathioprine and cyclophosphamide.

In some embodiments, the other therapeutic agent is an antibiotic (e.g., vancomycin, penicillin, amoxicillin, ampicillin, cefotaxime, ceftriaxone, cefixime, rifampinmetronidazole, doxycycline or streptomycin). In another embodiment, the other therapeutic agent is a PDE4 inhibitor (e.g., roflumilast or rolipram). In another embodiment, the other therapeutic agent is an antihistamine (e.g., cyclizine, hydroxyzine, promethazine or diphenhydramine). In another embodiment, the other therapeutic agent is an anti-malarial (e.g., artemisinin, artemether, artsunate, chloroquine phosphate, mefloquine hydrochloride, doxycycline hyclate, proguanil hydrochloride, atovaquone or halofantrine).

Another type of therapeutic agent useful in the combination treatment of the invention is an antibody such as a humanized monoclonal antibody. Non-limiting examples include, the anti-CD 99 antibody. See, for example, U.S. Pat. No. 7,223,395; White et al., Annu. Rev. Med., 52:125 (2001). Rituximab (Rituxan®; Genentech, South San Francisco, Calif.) is another therapeutic agent that is useful in a conjugate of the invention for treating rheumatoid arthritis. Another therapeutic agent useful in the invention also can be cytotoxic agents, which, as used herein, is any molecule that directly or indirectly promotes cell death. Specific anticancer agents include Flavopiridol, Adriamycin (doxorubicin), VP16 (Etoposide), Taxol (paclitaxel), cisplatin and the like.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, a-ketoglutarate, and a.-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds useful in practicing the invention can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

The compounds may be systemically administered, e.g., orally, in combination with a pharmaceutically acceptable vehicle such as an inert diluent or an assimilable edible carrier. Preferably, the route of administration is oral or intravenous. Other routes of administration include, for example, parental, intramuscular, topical and subcutaneous. The compounds may be enclosed in hard or soft shell gelatin capsules, may be compressed into tablets, or may be incorporated directly with the food of the patients diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

Just as in case of the compounds of the general structure A, the compounds of the general structure B may be administered in a variety of ways. For example, the tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The compounds may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be advisable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of structures A or B to the skin are known in the art; for example, see U.S. Pat. Nos. 4,608,392, 4,992,478, 4,559,157, and 4,820,508.

Useful dosages of the compounds can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compounds of the general structure B in a liquid composition, such as a lotion, may be between about 0.1 and about 25.0 mass %, such as between about 0.5 about 10.0 mass %. The concentration in a semi-solid or solid composition such as a gel or a powder may be between about 0.1 and about 5.0 mass %, such as between about 0.5 and 2.5 mass %.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician. In general, however, a suitable dose may be in the range of between about 0.2 and about 100.0 µmol/kg per day. In one embodiment, the dose can be, e.g., between about 0.2 to about 1.0 µmol/kg per day. In some embodiments, a suitable does may be in the rage of between about 0.5 and about 100 mg/kg, e.g., between about 10 and about 75 mg/kg of body weight per day, such as between about 3 and about 50 mg per kilogram body weight of the recipient per day, for example, in the range of between about 6 and about 90 mg/kg/day, such as in the range of between about 15 and about 60 mg/kg/day.

Pharmaceutical compositions suitable for use in the methods disclosed herein include compositions where the active ingredients are contained in an amount effective to achieve its intended purpose. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

The exact formulation, route of administration and dosage for the pharmaceutical compositions disclosed herein can be chosen by the individual physician in view of the patient's condition. Typically, the dose range of the composition administered to the patient can be between about 0.5 and about 1000 mg/kg, of the patient's body weight, or between about 1 and about 500 mg/kg, or between about 10 and about 500 mg/kg, or between about 50 and about 100 mg/kg of the patient's body weight. The dosage may be a single one or a series of two or more given in the course of one or more days, as is needed by the patient. Where no human dosage is established, a suitable human dosage can be inferred from $ED_{50}$ or $ID_{50}$ values, or other appropriate values derived from in vitro or in vivo studies, as qualified by toxicity studies and efficacy studies in animals.

Although the exact dosage will be determined on a drug-by-drug basis, in most cases, some generalizations regarding the dosage can be made. The daily dosage regimen for an adult human patient may be, for example, an oral dose of between about 0.1 mg and about 500 mg of each ingredient, such as between about 1 mg and about 250 mg, e.g. between about 5 and about 200 mg or an intravenous, subcutaneous, or intramuscular dose of each ingredient between about 0.01 mg and about 100 mg, such as between about 0.1 mg and about 60 mg, e.g. between about 1 and about 40 mg of each ingredient of the pharmaceutical compositions disclosed herein or a pharmaceutically acceptable salt thereof calculated as the free base, the composition being administered 1 to 4 times per day. Alternatively the compositions disclosed herein may be administered by continuous intravenous infusion, preferably at a dose of each ingredient up to 400 mg per day. Thus, the total daily dosage by oral administration of each ingredient will typically be in the range between about 1 and about 2000 mg and the total daily dosage by parenteral administration will typically be in the range between about 0.1 and about 400 mg. In some embodiments, the compounds will be administered for a period of continuous therapy, for example for a week or more, or for months or years.

Dosage amount and interval may be adjusted individually to provide plasma levels of the active moiety, which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen, which maintains plasma levels above the MEC for 10-90% of the time, such as between 30-90%, e.g., between 50-90%. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

In various embodiments, the compositions may, if desired, be presented in a pack or dispenser device, which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound disclosed herein formulated in a compatible pharmaceutical carrier may also be prepared, placed in an appropriate container, and labeled for treatment of an indicated condition.

In various embodiments, compounds of the invention can be labeled using methods known in the art. One detectable group is a fluorescent group. Fluorescent groups typically produce a high signal to noise ratio, thereby providing increased resolution and sensitivity in a detection procedure. For example, the fluorescent group absorbs light with a wavelength above about 300 nm, such as above about 350 nm, e.g., above about 400 nm. The wavelength of the light emitted by the fluorescent group is above about 310 nm, such as above about 360 nm, e.g., above about 410 nm.

The fluorescent detectable moiety can be selected from a variety of structural classes, including the following non-limiting examples: 1- and 2-amino-naphthalene, p,p'diaminostilbenes, pyrenes, quaternary phenanthridine salts, 9-aminoacridines, p,p'-diaminobenzophenone imines, anthracenes, oxacarbocyanine, marocyanine, 3-aminoequilenin, perylene, bisbenzoxazole, bis-p-oxazolyl benzene, 1,2-benzophenazin, retinol, bis-3-aminopridinium salts, hellebrigenin, tetracycline, sterophenol, benzimidazolyl phenylamine, 2-oxo-3-chromen, indole, xanthen, 7-hydroxycoumarin, phenoxazine, salicylate, strophanthidin, porphyrins, triarylmethanes, flavin, xanthene dyes (e.g., fluorescein and rhodamine dyes); cyanine dyes; 4,4-difluoro-4-bora-3a,4a-diaza-s-indacene dyes and fluorescent proteins (e.g., green fluorescent protein, phycobiliprotein).

In various embodiments, the compounds can be labeled, where the labeling group spontaneously emits a signal, or generates a signal upon the introduction of a suitable stimulus. Labels, include atoms such as, for example, $^{13}C$, $^{15}N$, $^{19}F$, $^{1}H$ and the like. In various embodiments, the compound can be conveniently administered in unit dosage form; for example, containing between about 5 and about 1,000 mg, such as between about 10 and about 750 mg, e.g., between about 50 and about 500 mg of active ingredient per unit dosage form.

In some embodiments, the active ingredient can be administered to achieve peak plasma concentrations of the active compound of between about 0.5 and about 75 μM, such as between about 1 and about 50 μM, e.g., between about 2 and about 30 μM. This may be achieved, for example, by the intravenous injection of a 0.05 to 5% solution of the active ingredient, optionally in saline, or orally administered as a bolus containing about 1-100 mg of the active ingredient. Desirable blood levels can be maintained by, for example, continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator.

EXAMPLES

Some aspects of the present invention can be further illustrated by the following non-limiting examples.

Example 1

Molecular Modeling

Molecular modeling studies were conducted on a Linux workstation and a 64 3.2-GHz CPUs Linux cluster. Docking studies were performed using the crystal structure of BCL-$X_L$ in complex with Bak-derived peptide (Protein Data Bank code 1BXL). The docked structures of 5,5' substituted Apogossypol derivatives in the peptide-binding pocket were obtained by ChemScore as the scoring function in the GOLD docking program. The protein surface was prepared with the program MOLCAD as implemented in Sybyl (Tripos, St. Louis).

Example 2

General Chemical Procedures

Unless otherwise noted, all reagents and anhydrous solvents ($CH_2Cl_2$, THF, diethyl ether, etc) were obtained from commercial sources and used without purification. All reactions were performed in oven-dried glassware. All reactions involving air or moisture sensitive reagents were performed under a nitrogen atmosphere. Silica gel chromatography was performed using prepacked silica gel or C-18 cartridges (RediSep). All final compounds were purified to >95% purity, as determined by a HPLC Breeze from Waters Co. using an Atlantis T3 3 µM 4.6 mm×150 mm reverse phase column. NMR spectra were recorded on Varian 300 or Bruker 600 MHz instruments. Chemical shifts are reported in ppm (δ) relative to $^1$H ($Me_4Si$ at 0.00 ppm). Coupling constant (J) are reported in Hz throughout. Mass spectral data were acquired on an Esquire LC00066 for low resolution, an Agilent ESI-TOF for high resolution.

Example 3

Synthesis of Compounds of the Invention

The synthesis for 5,5' substituted apogossypol derivatives is outlined in Scheme 1.

Scheme 1

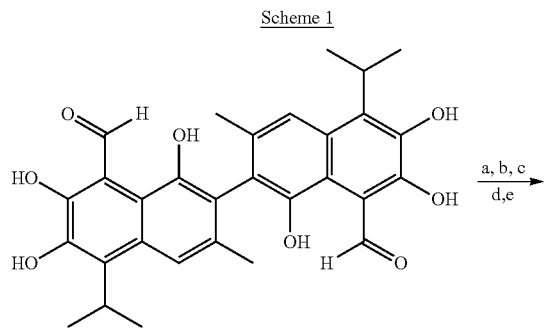

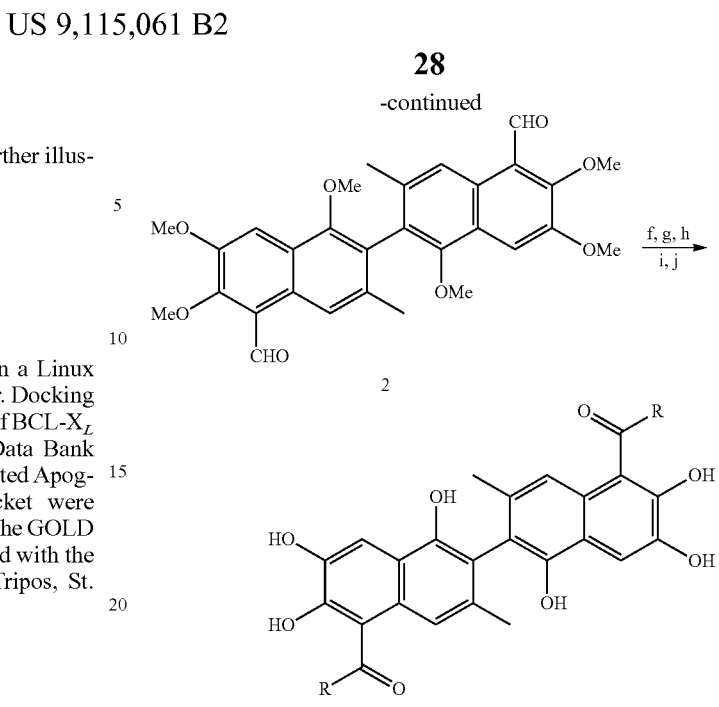

a NaOH, $H_2O$;
b $H_2SO_4$;
c DMS, $K_2CO_3$;
d $TiCl_4$, $Cl_2CHOCH_3$;
e HCl;
f RMgBr or RLi;
g $NH_4Cl$, $H_2O$;
h PCC, $CH_2Cl_2$;
i $BBr_3$;
j HCl.

Briefly and generally, gossypol 1 was treated with NaOH solution followed by dimethyl sulfate to afford methyl apogossypol. Reaction of methyl apogossypol with $TiCl_4$ and dichloromethyl methyl ether resulted in loss of isopropyl groups and simultaneous bisformylation to give aldehyde 2. The compound 2 was treated with different Grignard or lithium reagents to afford a secondary alcohol, which was oxidized to the phenone using pyridinium chlorochromate. Subsequent demethylation of the phenone afforded compound 3.

More specifically, the gossypol acetic acid 1 (5 g, 8.65 mmol) in 50 ml of 40% NaOH was heated under nitrogen at 90° C. for 3.5 hours in the dark. The reaction mixture was cooled and poured slowly onto ice (300 ml) and concentrated $H_2SO_4$ (35 ml) mixture to form white precipitation. The precipitation was filtered, washed with water and dried to afford apogossypol (3.8 g, 95%) as a white solid. $^1$H NMR ($CDCl_3$ δ 7.61 (s, 2H), 7.50 (s, 2H), 5.93 (s, 2H), 5.27 (s, 2H), 5.13 (s, 2H), 3.88 (m, 2H), 2.12 (s, 6H), 1.55 (d, J=5.5 Hz, 12H).

Apogossypol (3.8 g, 8.21 mmol) was then dissolved into 200 ml acetone. $K_2CO_3$ (23.9 g, 206.7 mmol) and dimethyl sulfate (16.3 ml, 206.7 mmol) were added and the reaction mixture was refluxed under nitrogen for 24 hours. The solid that separated from the solution was collected by filtration. It was washed (acetone and water) and dried to yield 4.2 g of methylated apogossypol (93%). To a solution of methylated apogossypol (1.6 g, 2.93 mmol) in dry methyl chloride (40 ml) at 0° C. was added titanium tetrachloride (14.3 g, 75.5 mmol). After addition was completed, the dark red solution was stirred an additional 15 min at 0° C. Dichloromethyl methyl ether (2.93 g, 25.5 mmol) was added dropwise over 15 min, and the reaction mixture was stirred at ambient temperature under nitrogen for 14 hr.

The reaction mixture was poured onto ice and the resulting aqueous layer was extracted twice with methyl chloride. The combined organic fractions were washed with water and brine, dried over $MgSO_4$, and concentrated to give dark red oil. The oil was chromatographed (acetonitrile/methyl chloride) followed by trituration of crude product with diethyl ether to afford intermediate 2 (0.60 g, 40%) as a yellow solid.

For intermediate 2: $^1$H NMR: 8.47 (s, 1H), 7.29 (s, 1H), 7.05 (br s, 1H), 2.79 (t, J=7.35 Hz, 2H), 2.47 (s, 3H), 2.44 (s, 3H), 1.70 (m, 2H), 1.03 (t, J=7.35 Hz, 3H).

Example 4

Synthesis of Compound I of the Invention

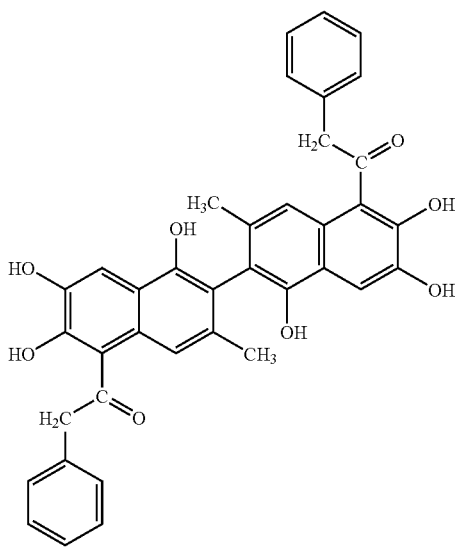

I

Compound I of the invention having the formula shown above, also known as 1,1'-(1,1',6,6',7,7'-hexahydroxy-3,3'-dimethyl-2,2'-binaphthyl-5,5'-diyl)bis(2-phenylethanone), was synthesized as follows. To a freshly benzylmagnesium chloride (5.4 mmol) solution at room temperature was added a solution of aldehyde 2 (1.0 g, 1.93 mmol) in anhydrous tetrahydrofuran (15 ml) and the reaction mixture was stirred at this temperature for 12 hr. The reaction mixture was poured onto saturated ammonium chloride solution and the aqueous layer was extracted twice with diethyl ether, washed with brine and dried over $MgSO_4$. Filtration followed by evaporation of the ether gave yellow oil. The solution of yellow oil in dry methyl chloride (10 ml) was added into pyridinium chlorochromate (2.6 g, 12.1 mmol) in dry methyl chloride (12 ml). The reaction mixture was stirred at ambient temperature for 4 hr and was filtrated trough celite The filtrate was chromatographed to afford 0.3 g of methylated compound I (22%). 0.27 mL of $BBr_3$ solution (0.72 g, 2.88 mmol) was added dropwise into a solution of methylated compound I (120 mg, 0.17 mmol) in 8 mL of anhydrous $CH_2Cl_2$ at −78° C. Stirring was continued at −78° C. for 1 hr, 0° C. for 1 hr, and ambient temperature for 1 hr. 50 grams of ice containing 10 mL of 6M hydrochloric acid was added to the mixture and stirred for one hour at room temperature. The aqueous layer was extracted with dichloromethane (3×30 mL). The combined organic layer was washed with water, brine and dried over $MgSO_4$. The solvent was concentrated in vacuo and the residue was purified by C-18 column chromatography ($H_2O$/Acetonitrile) to give 80 mg of compound c I (77%) as orange solid.

$^1$H NMR ($CD_3OD$) δ 7.61 (s, 2H), 7.30 (m, 8H), 7.22 (m, 2H), 6.97 (s, 2H), 4.40 (dd, $J_1$=15.6 Hz, $J_2$=22.8 Hz, 4H), 1.87 (s, 6H); $^{13}$C NMR $(CD_3)_2$SO) δ 204.6, 149.4, 144.8, 144.5, 135.4, 134.2, 130.5, 128.6, 126.9, 126.3, 122.6, 119.4, 116.8, 115.0, 107.1, 51.0, 21.1; HRMS calcd for $[C_{38}H_{30}O_8+H]$ 615.2019, found 615.2013. HPLC is 99% pure.

Example 5

Spectral Characteristics of Compounds of the Invention

Other derivatives encompassed by general structure A were synthesized and characterized. The synthesis followed the pattern described in Examples 3 and 4, with necessary adjustments, such as using different Grignard or lithium reagents when treating aldehyde intermediate compound 2. The spectral characteristics of the compounds were as follows (Roman numerals correspond to the above-described compounds of the invention).

Compound III. 1,1'-(1,1'6,6',7,7'-hexahydroxy-3,3'-dimethyl-2,2'-binaphthyl-5,5'-diyl)bis(2-methylpropan-1-one). $^1$H NMR ($CDCl_3$) δ 12.38 (s, 2H), 7.99 (s, 2H), 7.82 (s, 2H), 7.44 (s, 2H), 6.18 (s, 2H), 5.41 (s, 2H), 3.86 (m, 2H), 2.13 (s, 6H), 1.33 (d, J=9 Hz, 12H).

Compound XVIII. 1,1'-(1,1',6,6',7,7'-hexahydroxy-3,3'-dimethyl-2,2'-binaphthyl-5,5'-diyl)bis(2,2-dimethylpropan-1-one); $^1$H NMR ($CD_3OD$) δ 7.56 (s, 2H), 6.78 (s, 2H), 1.95 (s, 6H), 1.34 (m, 18H).

Compound IV. 1,1'-(1,1',6,6',7,7'-hexahydroxy-3,3'-diethyl-2,2'-binaphthyl-5,5'-diyl)bis(3-methylbutan-1-one). $^1$H NMR ($CD_3OD$) δ7.62 (s, 2H), 7.12 (s, 2H), 2.97 (d, J=6.6 Hz, 4H), 2.32 (m, 2H), 1.96 (s, 6H), 1.03 (d, J=3.6 Hz, 12H).

Compound XX. 1,1'-(1,1',6,6',7,7'-hexahydroxy-3,3'-dimethyl-2,2'-binaphthyl-5,5'-diyl)dipentan-1-one. $^1$H NMR ($CD_3OD$) δ 7.62 (s, 2H), 7.07 (s, 2H), 3.07 (t, $J_1$=$J_2$=6.6 Hz, 4H), 1.97 (s, 6H), 1.76 (m, 4H), 1.45 (m, 4H), 0.97 (t $J_1$=$J_2$=6.6 Hz, 6H).

Compound XIX. 1,1'-(1,1',6,6',7,7'-hexahydroxy-3,3'-dimethyl-2,2'-binaphthyl-5,5'-diyl)bis(2-methylbutan-1-one) $^1$H NMR ($CD_3OD$) δ 7.62 (s, 2H), 7.05 (s, 2H), 3.43 (m, 2H), 1.96 (s, 6H), 1.50 (m, 4H), 1.21 (d, J=6.6 Hz, 6H), 0.99 (d, J=7.2 Hz, 6H).

Compound VII. (1,1',6,6',7,7'-hexahydroxy-3,3'-dimethyl-2,2'-binaphthyl-5,5'-diyl)bis(phenylmethanone). $^1$H NMR ($CD_3OD$) δ 7.89 (d, J=6.6 Hz, 4H), 7.67 (s, 2H), 7.62 (s, 2H), 7.49 (s, 4H), 6.82 (s, 2H), 1.93 (s, 6H).

Compound XVII. (1,1',6,6',7,7'-hexahydroxy-3,3'-dimethyl-2,2'-binaphthyl-5,5'-diyl)bis(benzo[d]thiazol-2-ylmethanone). $^1$H NMR ($CD_3OD$) δ 8.14 (d, J=4.8 Hz, 2H), 8.07 (s, 2H), 7.75 (s, 2H), 7.59 (t, $J_1$=$J_2$=2.4 Hz, 4H), 7.03 (s, 2H), 1.93 (s, 6H).

Compound VI. (1,1',6,6',7,7'-hexahydroxy-3,3'-dimethyl-2,2'-binaphthyl-5,5'-diyl)bis(cyclopentylmethanone). $^1$H NMR ($CD_3OD$) δ 7.62 (s, 2H), 7.05 (s, 2H), 3.84 (m, $J_1$=$J_2$=7.2 Hz, 2H), 2.03 (m, 4H), 1.99 (s, 6H), 1.93 (m, 4H), 1.77 (m, 4H), 1.67 (m, 4H).

Compound VIII. (1,1',6,6',7,7'-hexahydroxy-3,3'-dimethyl-2,2'-binaphthyl-5,5'-diyl)bis(naphthalen-1-ylmethanone). $^1$H NMR ($CD_3OD$) δ 8.97 (d, J=7.8 Hz, 2H), 8.07 (m, 2H), 7.98 (d, J=7.8 Hz, 2H), 7.68 (m, 8H), 7.43 (m, 2H), 6.95 (s, 2H), 1.79 (s, 6H).

Compound V. 1,1'-(1,1',6,6',7,7'-hexahydroxy-3,3'-dimethyl-2,2'-binaphthyl-5,5'-diyl)bis(3-ethylheptan-1-one). $^1$H NMR ((CD$_3$)$_2$SO) δ 10.08 (s, 2H), 9.26 (s, 2H), 8.08 (s, 2H), 7.53 (s, 2H), 6.91 (s, 2H), 2.87 (d, J=5.7 Hz, 4H), 1.98 (m, 2H), 1.85 (s, 6H), 1.30 (m, 16H), 0.87 (t, J$_1$=J$_2$=7.5 Hz, 12H).

Compound IX. (1,1',6,6',7,7'-hexahydroxy-3,3'-dimethyl-2,2'-binaphthyl-5,51-diyl)bis(biphenyl-4-ylmethanone). $^1$H NMR (CD$_3$OD) δ 7.97 (d, J=8.1 Hz, 4H), 7.70 (m, 10H), 7.46 (m, 6H), 6.86 (s, 2H), 1.88 (s, 6H).

Compound X. (1,1',6,6',7,7'-hexahydroxy-3,3'-dimethyl-2,2'-binaphthyl-5,5'-diyl)bis((4-tert-butylphenyl)methanone). $^1$H NMR (CD$_3$OD) δ 7.82 (d, J=8.4 Hz, 4H), 7.65 (s, 2H), 7.51 (d, J=8.4 Hz, 4H), 6.80 (s, 2H), 1.86 (s, 6H), 1.34 (s, 18H).

Compound XI. (1,1',6,6',7,7'-hexahydroxy-3,3'-dimethyl-2,2'-binaphthyl-5,5'-diyl)bis((4-(trifluoromethyl)phenyl)methanone). $^1$H NMR (CD$_3$OD) δ 8.04 (d, J=7.8 Hz, 4), 7.78 (d, J=7.8 Hz, 4H), 7.69 (s, 2H), 6.87 (s, 2H), 1.88 (s, 6H).

Compound II. (3,3'-dimethyl-2,2'-binaphthyl-1,1',6,6',7,7'-hexaol). $^1$H NMR (CD$_3$OD) δ 7.46 (s, 2H), 7.11 (s, 2H), 7.03 (s, 2H), 1.97 (s, 6H).

Compound XVI. 1,1'-(1,1',6,6',7,7'-hexahydroxy-3,3'-dimethyl-2,2'-binaphthyl-5,5'-diyl)bis(3-(4-fluorophenyl)propan-1-one). $^1$H NMR (CD$_3$OD) δ 7.62 (s, 2H), 7.27 (d, J=5.4 Hz, 4H), 6.97 (m, 4H), 6.88 (s, 2H), 3.40 (t, J$_1$=J$_2$=6.6 Hz, 4H), 3.10 (t, J$_1$=J$_2$=6.6 Hz, 4H), 1.90 (s, 6H).

Compound XII. 1,1'-(1,1',6,6',7,7'-hexahydroxy-3,3'-dimethyl-2,2'-binaphthyl-5,5'-diyl)bis(2-p-tolylethanone). $^1$H NMR (CD$_3$OD) δ 7.59 (s, 2H), 7.15 (d, J=8.1 Hz, 4H), 7.05 (d, J=8.1 Hz, 4H), 6.93 (s, 2H), 4.30 (dd, J$_1$=15.6 Hz, J$_2$=9.9 Hz, 4H), 2.27 (s, 6H), 1.85 (s, 6H).

Compound XV. 1,1'-(1,1',6,6',7,7'-hexahydroxy-3,3'-dimethyl-2,2'-binaphthyl-5,5'-diyl)bis(2-cyclohexylethanone). $^1$H NMR (CD$_3$OD) δ 7.61 (s, 2H), 7.10 (s, 2H), 2.95 (dd, J$_1$=3.3 Hz, J$_2$=3.0 Hz, 4H), 2.02 (m, 2H), 1.95 (s, 6H), 1.76 (m, 10H), 1.11 (m, 10H).

Compound XIII. 1,1'-(1,1',6,6',7,7'-hexahydroxy-3,3'-dimethyl-2,2'-binaphthyl-5,5'-diyl)bis(2-(3-bromophenyl)ethanone). $^1$H NMR (CD$_3$OD) δ 7.63 (s, 2H), 7.51 (s, 2H), 7.29 (m, 6H), 7.00 (s, 2H), 4.36 (dd, J$_1$=8.1 Hz, J$_2$=9.0 Hz, 4H), 1.91 (s, 6H).

Compound XIV. 1,1'-(1,1',6,6',7,7'-hexahydroxy-3,3'-dimethyl-2,2'-binaphthyl-5,5'-diyl)bis(2-(4-(trifluoromethoxy)phenyl)ethanone) $^1$H NMR (CD$_3$OD) δ 7.63 (s, 2H), 7.41 (d, J=4.2 Hz, 4H), 7.20 (d, J=4.2 Hz, 4H), 6.99 (s, 2H), 4.40 (dd, J$_1$=8.1 Hz, J$_2$=7.2 Hz, 4H), 1.88 (s, 6H).

Figure 12:
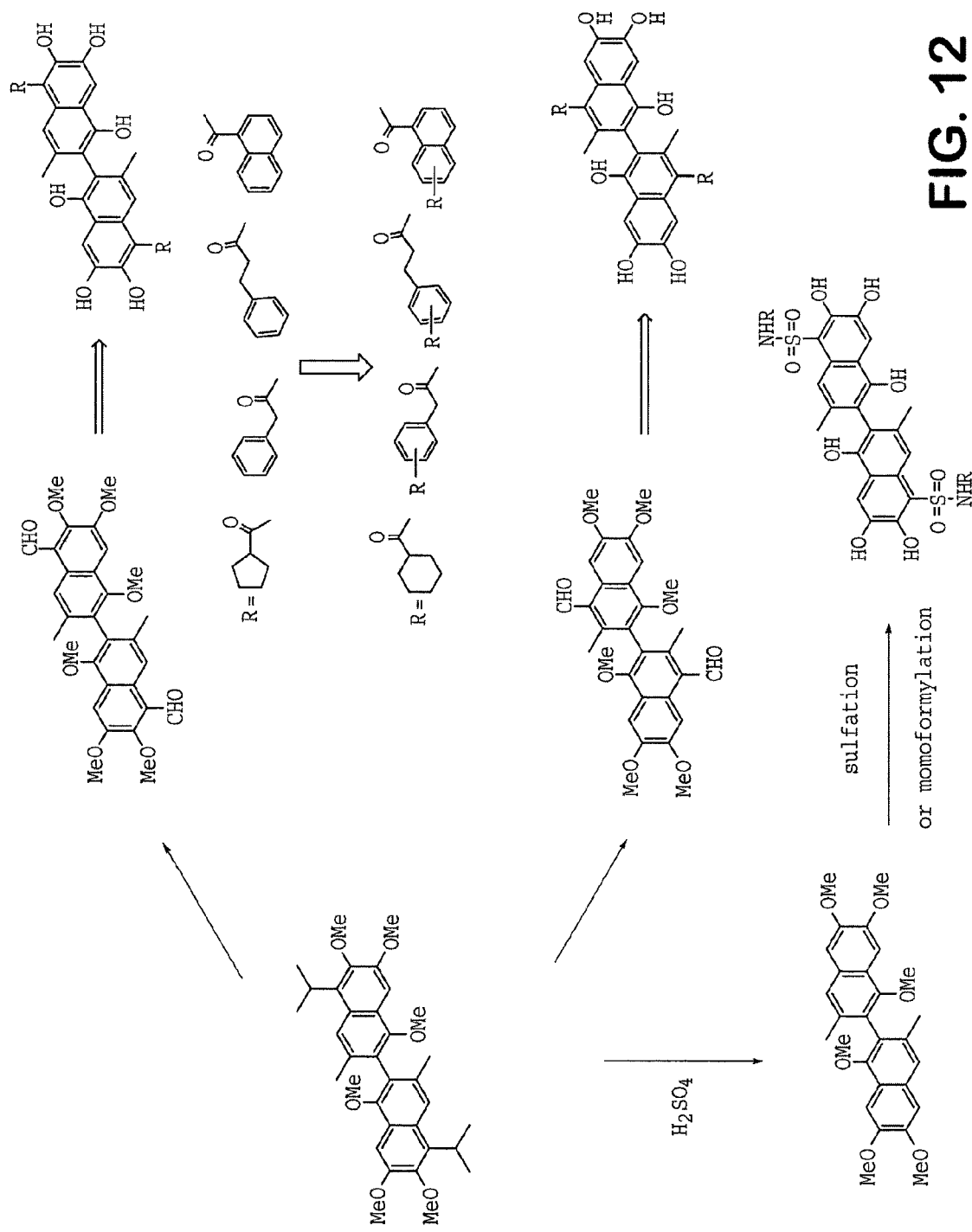
FIG. 12 shows a general synthetic scheme that can be used to synthesize some compounds of the invention.

Some compounds of the invention may be synthesized as shown on FIG. 12 (where R is CONX or CONR$_1$X, where R or R$_1$ is an alkyl, aromatic, or heterocyclic group, and X is an alkyl, a substituted alkyl, an aryl, a substituted aryl, an alkylaryl, and a heterocycle).

Further spectral data and the data on purity with respect to compounds of the invention are summarized in Table 1.

TABLE 1

High Resolution Mass (HRMS) and HPLC Purity of 5, 5' substituted Apogossypol Derivatives

| Compound | Chemical Formula [M + H]$^+$ | HRMS Calculated | Found | HPLC Purity (%) |
|---|---|---|---|---|
| Gossypol | C$_{30}$H$_{31}$O$_8$ | NR | NR | 99.6 |
| Apogossypol | C$_{28}$H$_{31}$O$_6$ | 463.2115 | 463.2108 | 99.5 |
| III | C$_{30}$H$_{31}$O$_8$ | 519.2013 | 519.2013 | 99.5 |
| XVIII | C$_{32}$H$_{35}$O$_8$ | 547.2326 | 547.2327 | 99.3 |
| IV | C$_{32}$H$_{35}$O$_8$ | 547.2326 | 547.2326 | 99.3 |
| XX | C$_{32}$H$_{35}$O$_8$ | 547.2326 | 547.2324 | 97.1 |
| VII | C$_{36}$H$_{27}$O$_8$ | 587.1700 | 587.1702 | 99.4 |
| XVII | C$_{38}$H$_{25}$N$_2$O$_8$S$_2$ | 701.1047 | 701.1042 | 97.8 |
| VI | C$_{34}$H$_{35}$O$_8$ | 571.2326 | 571.2325 | 98.8 |
| VIII | C$_{44}$H$_{31}$O$_8$ | 687.2013 | 687.2027 | 97.2 |
| I | C$_{38}$H$_{31}$O$_8$ | 615.2013 | 615.2014 | 99.0 |
| V | C$_{40}$H$_{51}$O$_8$ | 659.3578 | 659.3583 | 98.8 |
| IX | C$_{48}$H$_{35}$O$_8$ | 739.2326 | 739.2323 | 99.5 |
| X | C$_{44}$H$_{43}$O$_8$ | 699.2952 | 699.2946 | 99.6 |
| XI | C$_{38}$H$_{25}$F$_6$O$_8$ | 723.1448 | 723.1447 | 99.6 |
| II | C$_{22}$H$_{19}$O$_6$ | 379.1176 | 379.1168 | 98.5 |
| XVI | C$_{40}$H$_{33}$F$_2$O$_8$ | 679.2138 | 679.2139 | 96.8 |
| XVII | C$_{40}$H$_{35}$O$_8$ | 643.2326 | 643.2328 | 98.6 |
| XV | C$_{38}$H$_{43}$O$_8$ | 627.2952 | 627.2949 | 98.6 |
| XIII | C$_{38}$H$_{29}$Br$_2$O$_8$ | 771.0224 | 771.0225 | 98.1 |
| XII | C$_{40}$H$_{29}$F$_6$O$_{10}$ | 783.1659 | 783.1651 | 95.6 |

Example 6

NMR Experiments

NMR-based binding assays have been conducted by acquiring one-dimensional $^1$H experiments with 500 µL solution of BCL-X$_L$ at 25 µM concentration, in absence and presence of added compounds, each at 200 µM concentration. By observing the aliphatic region of the spectra, binding could be readily detected due to chemical shift changes in active site methyl groups of Ile, Leu, Thr, Val or Ala (region between −0.8 and 0.3 ppm). All experiments were performed with a 600 MHz spectrometer Bruker Avance 600 equipped with four rf channels and z-axis pulse-field gradients.

Example 7

Fluorescence Polarization Assays (FPA)

A Bak BH3 peptide (F-BakBH3) (GQVGRQLAIIGD-DINR) was labeled at the N-terminus with fluorescein isothiocyanate (FITC) (Molecular Probes) and purified by HPLC. For competitive binding assays, 100 nM GST-BCL-X$_L$ ΔTM protein was preincubated with the tested compound at varying concentrations in 47.5 µL PBS (pH=7.4) in 96-well black plates at room temperature for 10 min, then 2.5 µL of 100 nM FITC-labeled Bak BH3 peptide was added to produce a final volume of 50 µL. The wild-type and mutant Bak BH3 peptides were included in each assay plate as positive and negative controls, respectively.

After 30 min incubation at room temperature, the polarization values in millipolarization units were measured at excitation/emission wavelengths of 480/535 nm with a multilabel plate reader (PerkinElmer). IC$_{50}$ was determined by fitting the experimental data to a sigmoidal dose-response nonlinear regression model (SigmaPlot 10.0.1, Systat Software, Inc., San Jose, Calif., USA). Data reported are mean of three independent experiments ±standard error (SE). Performance of BCL-2 and Mcl-1 FPA are similar. Briefly, 50 nM of GST-BCL-2 or -Mcl-1 were incubated with various concentrations of Apogossypol, or its 5,5' substituted derivatives for 2 min, then 15 nM FITC-conjugated-Bim BH3 peptide was added in PBS buffer. Fluorescence polarization was measured after 10 min.

Example 8

Isothermal Titration Calorimetry Assays (ITC)

Titrations were performed using a VP-ITC or ITC200 calorimeter from Microcal (Northampton, Mass.). BCL-$X_L$ was used at concentrations between 25 and 100 μM in 20 mM sodium phosphate buffer (pH 7.4) and 5-10% DMSO. Titrants were used at concentrations 10-15× of the protein in the same buffer. Titrations were carried out at 25° C. Data were analyzed using Microcal Origin software provided by the ITC manufacturer (Microcal, Northampton, Mass.).

Example 9

Cell Viability Assays

The activity of the compounds against human cancer cell lines (PC3ML, H460, H1299, RS11846) were assessed by using the ATP-LITE assay (PerkinElmer). All cells were seeded in either F12 or RPMI1640 medium with 5 mM L-glutamine supplemented with 5% fetal bovine serum (Mediatech Inc.), penicillin and streptomycin (Omega). For maintenance, cells were cultured in 5% FBS. Cells plated into 96 well plates at varying initial densities depending on doubling time. H460 and H1299 plated at 2000 cells/well, A549 and PC3 at 3000 cells/well, and RS118456S at 10,000 cells/well. Compounds were diluted to final concentrations with 0.1% DMSO. Prior to dispensing compounds onto cells, fresh 5% media was placed into wells. Administration of compounds occurred 24 hours after seeding into the fresh media. Cell viability was evaluated using ATP-LITE reagent (PerkinElmer) after 72 hours of treatment. Data were normalized to the DMSO control-treated cells using Prism version 5.01 (Graphpad Software).

The apoptotic activity of the compounds against RS11846 cells was assessed by staining with Annexin V- and propidium iodide (PI). Lymphoma cell line, RS11846, was cultured in RPMI 1640 medium (Mediatech Inc., Herndon, Va. 20171) containing 10% fetal bovine serum (Mediatech Inc., Herndon, Va. 20171) and Penicillin/Streptomycin (Mediatech Inc., Herndon, Va. 20171). Cells were cultured with various concentrations of 5,5' substituted Apogossypol for 1-2 days. The percentage of viable cells was determined by FITC-Annexin V- and propidium iodide (PI)-labeling, using an Apoptosis Detection kit (BioVision Inc.), and analyzing stained cells by flow cytometry (FACSort; Bectin-Dickinson, Inc.; Mountain View, Calif.). Cells that were annexin-V-negative and PI-negative were considered viable.

Example 10

In Vitro ADMET Studies

Liver Microsomal Stability.

Pooled rat liver microsomes (BD Biosciences, #452701) were preincubated with test compounds at 37.5° C. for 5 min in the absence of NADPH. The reaction was initiated by addition of NADPH and then incubated under the same conditions. The final incubation concentrations were 4 μM test compound, 2 mM NADPH, and 1 mg/mL (total protein) liver microsomes in phosphate-buffered saline (PBS) at pH 7.4. One aliquot (100 μL) of the incubation mixture was withdrawn at 0, 15, 30, and 60 min and combined immediately with 200 μL of ACN/MeOH containing an internal standard. After mixing, the sample was centrifuged at approximately 13,000 rpm for 12 min. The supernatant was transferred into an autosampler vial and the amount of test compound was quantified using the Shimadzu LCMS 2010EV mass spectrometer. The change of the AUC (area under the curve) of the parent compound as function of time was used as a measure of microsomal stability.

Plasma Stability.

A 20 μL aliquot of a 10 mM solution in DMSO of the test compound was added to 2.0 μL of heparinized rat plasma (Lampire, P1-150N) to obtain a 100 μM final solution. The mixture was incubated for 1 h at 37.5° C. Aliquots of 100 μL were taken (0, 30 min, 1 h) and diluted with 200 μL of MeOH containing internal standard. After mixing, the sample was centrifuged at approximately 13,000 rpm for 12 min. The supernatant was transferred into an autosampler vial and the amount of test compound was quantified using the Shimadzu LCMS-2010EV system. The change of the AUC (area under the curve) of the parent compound as function of time was used as a measure of microsomal stability.

Example 11

PAMPA Assays

PAMPA is parallel artificial membrane permeation assay. A 96-well microtiter plate (Millipore, # MSSACCEPTOR) was completely filled with aqueous buffer solution (pH 7.2) and covered with a microtiter filterplate (Millipore, # MAPBMN310). The hydrophobic filter material was impregnated with a 10% solution of hexadecane in hexane and the organic solvent was allowed to completely evaporate. Permeation studies were started by the transfer of 200 μL of a 100 μM test compound solution on top of the filterplate. In general phosphate buffer at pH 7.2 buffer was used. The maximum DMSO content of the stock solutions was <5%. In parallel, an equilibrium solution lacking a membrane was prepared using the exact concentrations and specifications but lacking the membrane. The concentrations of the acceptor and equilibrium solutions were determined using the Shimadzu LCMS-2010EV and AUC methods. The permeation of a compound through the membrane layer is described by the percentage permeation (% flux). The flux values were calculated considering the concentration of the acceptor compartment after 8 h and that of a reference well with the same concentration containing no membrane barrier.

Example 12

Transgenic Mice Studies

Transgenic mice expressing BCL-2 have been described as the B6 line. The BCL-2 transgene represents a minigene version of a t(14;18) translocation in which the human BCL-2 gene is fused with the immunoglobulin heavy-chain (IgH) locus and associated IgH enhancer. The transgene was propagated on the Balb/c background. These mice develop polyclonal B-cell hyperplasia with asynchronous transformation to monoclonal aggressive lymphomas beginning at approximately 6 months of age, with approximately 90% of mice undergoing transformation by the age of 12 to 24 months. All animals used here had not yet developed aggressive lymphoma.

Example 13

Further Mouse Experiments

Compounds dissolved in 500 μL of solution Ethanol:Cremophor EL:Saline=10:10:80) were injected intraperitoneally to age- and sex-matched B6BCL2 mouse, while control-mice were injected intraperitoneally with 500 μL of the same formulation without compound. After 24 hours, B6BCL2 mice were sacrificed by intraperitoneal injection of lethal dose of Avertin. Spleen was removed and weighed. The spleen weight of mice is used as an end-point for assessing activity as we determined that spleen weight is highly consistent in age- and sex-matched BCL-2-transgenic mice in preliminary studies. Variability of spleen weight was within ±2% among control-treated age-matched, sex-matched B6BCL2 mice. Spleen tissue was fixed in z-FIX for 3 days and rinsed in PBS, and saved for histological analysis of spleen (H&E staining and TUNEL assay).

Example 14

Comparisons with Apogossypol

Figure 1B:
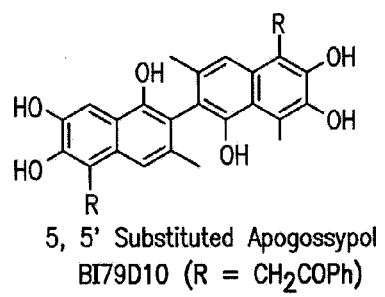
Figure 1C:
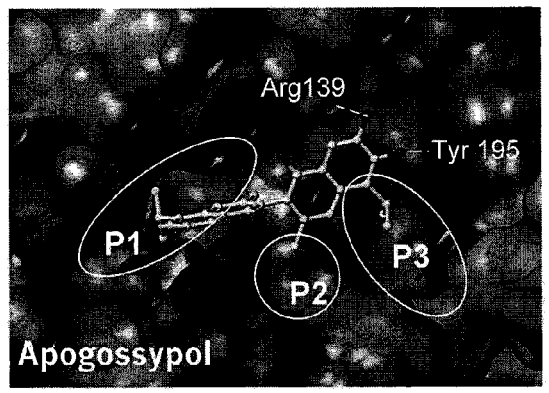

Molecular docking studies of apogossypol into the BH3 binding groove in BCL-$X_L$ FIG. 1C) suggest that apogossypol forms two hydrogen bonds with residues Arg 139 and Tyr 195 in BCL-$X_L$ through adjacent sixth and seventh hydroxyl groups on the right naphthalene ring. The isopropyl group on the left naphthalene ring inserts into the first hydrophobic pocket (P1) in BCL-$X_L$, while the methyl group and the isopropyl group on the right naphthalene ring insert into the adjacent two hydrophobic pockets, P2 and P3, respectively. Analysis of the predicted binding models indicates that while the overall core structure of apogossypol fits rather well into BH3 binding groove of BCL-$X_L$, the two isopropyl groups do not apparently fully occupy the hydrophobic pockets P1 and P3.

Therefore, a library of 5,5' substituted apogossypol derivatives (FIG. 1B) that replace the isopropyl groups with larger hydrophobic substituents was designed with the aim of deriving novel molecules that could occupy the hydrophobic pockets on BCL-$X_L$ more efficiently.

The designed 5,5' substituted apogossypol derivatives were synthesized as described above and evaluated by nuclear magnetic resonance spectroscopy (NMR) binding assays, competitive fluorescence polarization assays (FPA), and cell viability assays as shown in Table 2.

TABLE 2

Evaluation of 5, 5' Substituted Apogossypol Derivatives Using a Combination of 1D
$^1$H-NMR Binding Assays, Competitive Fluorescence Polarization Assays and Cell Viability Assays

| Compound | R | 1D $^1$H-NMR Binding Assay[a] (BCL-$X_L$) | FPA $IC_{50}$ (μM) (BCL-$X_L$) | PC3ML $EC_{50}$ (μM) | H460 $EC_{50}$ (μM) | H1299 $EC_{50}$ (μM) | RS11846[b] $EC_{50}$ (μM) | RS11846[c] $EC_{50}$ (μM) |
|---|---|---|---|---|---|---|---|---|
| Gossypol | isopropyl | ++ | 2.72 | 3.1 | 3.0 | 6.0 | 2.2 | 4.23 |
| Apogossypol | isopropyl | ++ | 3.69 | 10.3 | 2.8 | 3.4 | 5.0 | 8.6 |
| I | benzyl ketone | +++ | 0.19 | 4.6 | 0.68 | 3.5 | 2.6 | 4.9 |
| II | —H | + | NR | 12.6 | 10.1 | 13.4 | 10.0 | 24.7 |
| III | isopropyl ketone | ++ | NR | 3.9 | 1.5 | 4.8 | 15 | 14.7 |
| IV | isobutyl ketone | + | 1.30 | 7.5 | 1.1 | 3.6 | 10 | 13.7 |

TABLE 2-continued

Evaluation of 5, 5' Substituted Apogossypol Derivatives Using a Combination of 1D $^1$H-NMR Binding Assays, Competitive Fluorescence Polarization Assays and Cell Viability Assays

| Compound | R | 1D $^1$H-NMR Binding Assay[a] (BCL-$X_L$) | FPA IC$_{50}$ (µM) (BCL-$X_L$) | PC3ML EC$_{50}$ (µM) | H460 EC$_{50}$ (µM) | H1299 EC$_{50}$ (µM) | RS11846[b] EC$_{50}$ (µM) | RS11846[c] EC$_{50}$ (µM) |
|---|---|---|---|---|---|---|---|---|
| V | (3-ethylheptan-2-one) | + | 1.29 | 3.0 | 1.5 | 3.0 | 2.8 | 6.6 |
| VI | (cyclopentyl methyl ketone) | + | 0.45 | 3.4 | 1.1 | 3.1 | 4.0 | 4.5 |
| VII | (acetophenone) | + | 2.9 | 3.6 | 0.31 | 4.2 | NR | 18.3 |
| VIII | (1-naphthyl methyl ketone) | + | 0.16 | 3.0 | 0.59 | 2.4 | 1.8 | 4.2 |
| IX | (4-phenylacetophenone) | − | NR | 7.7 | 8.2 | 9.6 | 2.8 | 25.9 |
| X | (4-tert-butylacetophenone) | − | NR | 2.8 | 3.6 | 4.8 | 2.3 | 13.4 |

TABLE 2-continued

Evaluation of 5, 5' Substituted Apogossypol Derivatives Using a Combination of 1D $^1$H-NMR Binding Assays, Competitive Fluorescence Polarization Assays and Cell Viability Assays

| Compound | R | 1D $^1$H-NMR Binding Assay[a] (BCL-$X_L$) | FPA IC$_{50}$ (μM) (BCL-$X_L$) | PC3ML EC$_{50}$ (μM) | H460 EC$_{50}$ (μM) | H1299 EC$_{50}$ (μM) | RS11846[b] EC$_{50}$ (μM) | RS11846[c] EC$_{50}$ (μM) |
|---|---|---|---|---|---|---|---|---|
| XI | 4-(F$_3$C)-C$_6$H$_4$-C(O)-CH$_2$- | + | 0.25 | 2.9 | 2.2 | 2.0 | 2.5 | 3.8 |
| XII | 4-(H$_3$C)-C$_6$H$_4$-CH$_2$-C(O)- | ++ | 0.32 | 2.5 | 0.82 | 1.7 | 2.2 | 3.0 |
| XIII | 3-Br-C$_6$H$_4$-CH$_2$-C(O)- | ++ | 1.31 | 3.1 | 2.7 | 2.6 | 8.4 | 5.3 |
| XIV | 4-(F$_3$CO)-C$_6$H$_4$-CH$_2$-C(O)- | ++ | 1.30 | 1.9 | 3.3 | 3.9 | 1.8 | 6.2 |
| XV | cyclohexyl-CH$_2$-C(O)- | ++ | NR | 1.9 | 1.8 | 2.1 | 2 | 5.2 |
| XVI | 4-F-C$_6$H$_4$-CH$_2$CH$_2$-C(O)- | + | 0.14 | 2.8 | 1.5 | 2.2 | 2.3 | 3.1 |
| XVII | benzothiazol-2-yl-C(O)- | ++ | 0.39 | 5.2 | 1.4 | 5.8 | 2.9 | 7 |
| XVIII | (H$_3$C)$_3$C-C(O)- | ++ | NR | NR | NR | NR | NR | 14.7 |

TABLE 2-continued

Evaluation of 5, 5' Substituted Apogossypol Derivatives Using a Combination of 1D
¹H-NMR Binding Assays, Competitive Fluorescence Polarization Assays and Cell Viability
Assays

| Compound | R | 1D ¹H-NMR Binding Assay[a] (BCL-$X_L$) | FPA IC$_{50}$ (μM) (BCL-$X_L$) | PC3ML EC$_{50}$ (μM) | H460 EC$_{50}$ (μM) | H1299 EC$_{50}$ (μM) | RS11846[b] EC$_{50}$ (μM) | RS11846[c] EC$_{50}$ (μM) |
|---|---|---|---|---|---|---|---|---|
| XIX | (2-methylbutanoyl) H₃C-CH₂-CH(CH₃)-C(=O)- | + | NR | NR | NR | NR | NR | 17.1 |
| XX | (pentanoyl) H₃C-(CH₂)₃-C(=O)- | + | NR | NR | NR | NR | NR | 11.7 |

[a]4-point-rating scale: +++: Very Active; ++: Active; +: Mild; −: Weak
[b]Compounds against RS11846 cell line using ATP-LITE assay
[c]Compounds against RS11846 cell line using Annexin V-and propidium iodide assay Compound I (FIG. 1B) displayed high affinity for BCL-$X_L$ in these assays. It induced significant chemical shift changes in active site methyl groups (region between −0.3 and 0.8 ppm) in the one-dimensional ¹H-NMR spectra of BCL-$X_L$ (FIG. 2A) and also has an IC$_{50}$ value of 0.19 μM in the FP displacement assays, which is almost 20 times more effective than apogossypol (Table 2).

A group of compounds, such as compounds XVII, VI, VIII, XI, XVI, and XII also displayed high binding affinity to BCL-$X_L$ in the FP assays with IC$_{50}$ values ranging from 0.14 to 0.45 μM and induced chemical shift changes in the one-dimensional ¹H-NMR spectra of BCL-$X_L$ (Table 2). To confirm results of the NMR binding data and the FP assays, the binding affinity of compound I and other compounds was further evaluated for BCL-$X_L$ using ITC (Isothermal Titration Calorimetry) (Table 3).

TABLE 3

Cross-Activity of Selected 5, 5' Substituted
Apogossypol Derivatives Against BCL-$X_L$, BCL-2, and Mcl-1.

| Compound | R | EC$_{50}$ (μM) FPA | | | K$_d$ (μM) ITC |
|---|---|---|---|---|---|
| | | BCL-$X_L$ | BCL-2 | Mcl-1 | BCL-$X_L$ |
| Apogossypol | CH(CH₃)₂ | 3.69 | 2.80 | 2.60 | 1.70 |

TABLE 3-continued

Cross-Activity of Selected 5, 5' Substituted Apogossypol Derivatives Against BCL-$X_L$, BCL-2, and Mcl-1.

[Structure: 5,5'-substituted apogossypol core with R groups shown]

| Compound | R | EC$_{50}$ (μM) FPA | | | K$_d$ (μM) ITC |
|---|---|---|---|---|---|
| | | BCL-$X_L$ | BCL-2 | Mcl-1 | BCL-$X_L$ |
| I | [benzyl ketone] | 0.19 | 0.36 | 0.52 | 0.17 |
| XII | [4-methylbenzyl ketone] | 0.32 | 0.78 | 1.10 | 0.04 |
| VIII | [1-naphthyl ketone] | 0.16 | 1.90 | 2.20 | 2.75 |

Figure 1D:
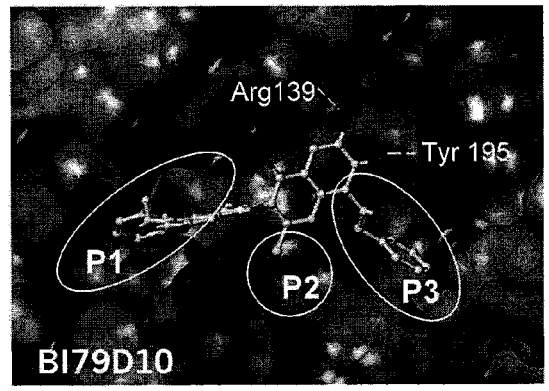
Figure 4:
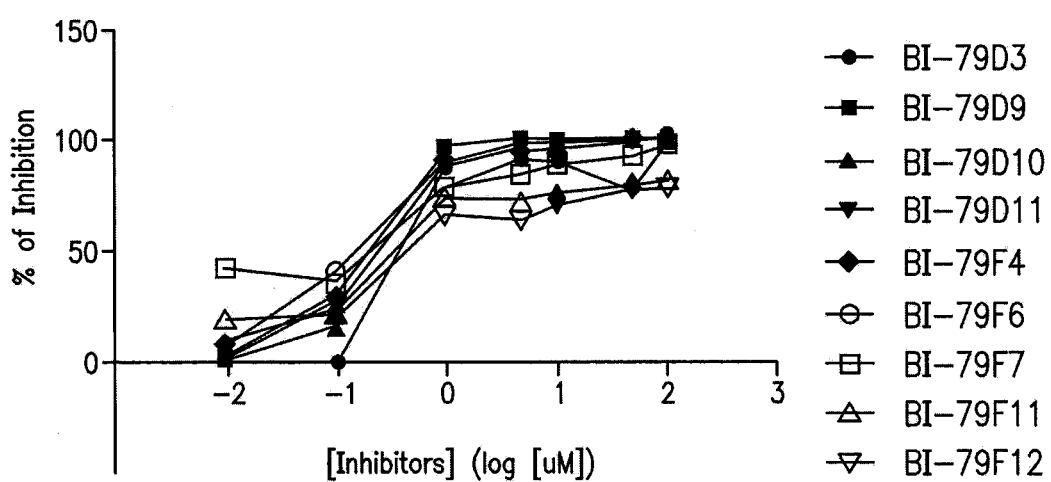
FIG. 4 demonstrates FP competitive binding curves of compounds of the invention using BCL-$X_L$.

As can be seen, in agreement with NMR binding and FPA data, compound I and its para-methyl substituted derivative compound XII, displayed potent binding affinity to BCL-$X_L$ with $K_d$ values of 0.17 and 0.04 μM, respectively, which is 10 and 40 times more potent than apogossypol ($K_d$=1.7 μM) in the same assay. Molecular docking studies of compound I in the BH3 binding groove of BCL-$X_L$ (FIG. 1D) demonstrated that 5,5' benzyl groups insert deeper into hydrophobic pockets (P1 and P3) in BCL-$X_L$ hence occupying these regions more efficiently compared to isopropyl groups of apogossypol.

Consistent with NMR binding, FPA, and ITC data compounds such as compounds I and XII display significant efficacy in inhibiting cell growth in PC3ML cells, which express high levels of BCL-$X_L$. Their EC$_{50}$ values ranged from 1.9 to 4.6 μM, hence 2-5 fold more potent than apogossypol (EC$_{50}$=10.3 μM).

To evaluate the binding properties and specificity of 5,5' substituted apogossypol derivatives to other anti-apoptotic BCL-2 family proteins, selected BCL-$X_L$ active compounds were evaluated against BCL-2 and Mcl-1 using FP assays (Table 3 and FIG. 2B). These BCL-$X_L$ inhibitors also displayed strong binding affinity to BCL-2 and Mcl-1. Compound I binds to BCL-2 and Mcl-1 with EC$_{50}$ values of 0.36 and 0.52 μM, respectively, which are approximately 8 and 5 fold more potent than apogossypol (EC$_{50}$=2.8 μM). Compound XII is slightly less active than compound I, while compound VIII has activity that is similar to that of apogossypol.

Since compounds I and XII displayed strong binding affinities to BCL-2 and Mcl-1 in FP assay, all 5,5' substituted apogossypol derivatives were further evaluated against H460 and H1299 cell lines, which express high levels of BCL-2 and Mcl-1, respectively (Table 2). In agreement with FPA data, compounds I and XII inhibited growth of the H460 cell line with EC$_{50}$ values of 0.68 and 0.82 μM, respectively, which are approximately 4-5 times more potent than apogossypol (EC$_{50}$=3.4 μM). Compounds VII and VIII having structures that are similar to that of compound I also inhibited cell growth in the H460 cell line with EC$_{50}$ values of 0.30 and 0.59 μM, respectively. Most of the tested 5,5' substituted apogossypol derivatives also showed potent cell activity in the H460 and H1299 cell lines with EC$_{50}$ values ranging from 1 to 4 μM.

In contrast, compound II (Table 2), the negative control compound with only hydrogen atoms on 5,5' positions, displayed weak cell growth inhibition activity in both H460 (EC$_{50}$=10.1 μM) and H1299 (EC$_{50}$=13.4 μM) cell lines indicating 5,5' substituted groups are necessary for strong inhibition. This observation is in agreement with reports for the potent BCL-$X_L$ antagonist ABT-737, which is not effective against Mcl-1 and consequentially is not effective in killing Mcl-1 overexpressing cell lines such as the H1299.

5,5' substituted apogossypol derivatives were further tested for their ability to induce apoptosis of the human lymphoma RS11846 cell line, which expresses high levels of BCL-2 and BCL-$X_L$. For these assays, we used Annexin V-FITC and propidium iodide (PI) double staining, followed by flow-cytometry analysis (Table 2). Most of synthesized apogossypol derivatives effectively induced apoptosis of the RS11846 cell line in a dose-dependent manner (Table 2). In particular, compounds I, VIII, XI, and XII have EC$_{50}$ values ranging from 3.0 to 5.5 µM, which is consistent with previous results in human cancer PC3ML and H460 cell lines. Again, the negative control compound II induced weak apoptosis $EC_{50}$=24.7) of the RS11846 cell line, consistent with its poor anti-BCL-2 activity.

To test the pharmacological properties of 5,5' substituted apogossypol derivatives, their in vitro plasma stability, microsomal stability, and cell membrane permeability were determined. The results are shown in Table 4.

similar or improved microsomal stability compared to Apogossypol, while compounds VI and XVIII, degraded faster than apogossypol in rat hepatocytes microsomal preparations. Compounds I and XII also displayed improved cell membrane permeability compared to apogossypol.

Accordingly, using a combination of 1D $^1$H-NMR binding assays, FP assays, ITC assays, cytotoxicity assays and preliminary in vitro ADME data, compounds such as compounds I and XII were selected for further in vivo studies using

TABLE 4

Plasma Stability, Microsomal Stability, and Cell Permeability of Selected 5, 5' Substituted Apogossypol Derivatives

| Compound | R | Plasma Stability (T = 1 hr) | Microsomial Stability (T = 1 hr) | Cell Permeability |
|---|---|---|---|---|
| Apogossypol | isopropyl | 53% | 60% | Low |
| XVII | benzothiazol-2-yl ketone | 90% | 68% | Medium |
| VI | cyclopentyl ketone | 79% | 27% | Low |
| VIII | naphthalen-1-yl ketone | 62% | 52% | Low |
| I | benzyl ketone (phenylacetyl) | 85% | 64% | Medium |
| XII | 4-(trifluoromethyl)phenyl ketone | NR | 41% | Low |
| XII | 4-methylphenyl acetyl | 72% | 92% | Medium |
| XVIII | tert-butyl methyl ketone (pivaloyl-like) | 90% | 30% | Medium |

As can be seen from the data provided in Table 4, the synthesized compounds of the invention displayed superior plasma stability and overall are more stable than apogossypol. Compounds I only degraded 15% after 1 hour incubation in rat plasma. In addition, compounds I and XII showed B6BCL-2 transgenic mice. B-cells of the B6BCL-2 transgenic mice overexpress BCL-2 and accumulate in the spleen of mice. The spleen weight is used as an end-point for assessing in vivo activity as we have determined that the spleen weight is highly consistent in age- and sex-matched BCL-2- transgenic mice and variability was within ±2% among control-treated age-matched, sex-matched B6BCL2 mice. The in vivo activities of compounds such as compounds I and XII were first screened side by side with apogossypol and gossypol in a single BCL-2 transgenic mouse at 60 μmol/kg.

All tested compounds induced significant spleen weight reduction of mice (FIG. 3A) and compound I displayed best efficiency causing 40% reduction in spleen weight. Since the maximum spleen shrinkage would be no more than 50% in this experimental model, the in vivo effect of compound I induced near maximal biological activity at 60 μmol/kg. To confirm the result from a single mouse experiment, the in vivo activity of compound I was next evaluated in groups of six mice each. In agreement with the single mouse experiment, compound I treatment of these mice resulted in a significant (~40%) reduction of spleen weight (P<0.0001), compared to the control group of six mice (FIG. 3B). All mice tolerated the treatment well with no macroscopic toxicity; the maximal weight loss was 4% during the course of study of compound I.

Example 15

Mouse Model for Prevention and Treatment of Systemic Lupus Erythematosus (SLE)

This example illustrates a proposed study to examine the effect of apogossypol treatment on development of SLE in the New Zealand black×New Zealand white F1 (NZBW) and MRL/lpr mouse models.

Prevention Studies

Two genetically diverse strains, NZB/NZW F1 (which is genetically similar to B6.Sle1.Sle3 congenics) and MRL/lpr would be subjected to preventative studies from the age of 3 mo, to the age of 5 mo, i.e., for a 2 month period. Mice will be checked to ensure they are negative for anti-nuclear autoantibodies at the beginning of the study. In one example, 10 mice of each strain will receive apogossypol, whereas another 10 age/gender matched females will receive the vehicle ("placebo group"). Although 10 mice will be tested initially, these numbers could easily be ramped up following the power analysis conducted using the initial set of data obtained. Mice will be given from between about 0.2 μmol/kg to about 1.0 μmol/kg per day. Preferably, the route of administration will be oral. However, intravenous administration can also be used.

The mice will be monitored at fortnightly intervals for serum autoantibody levels and 24-hour urine protein levels, and at monthly intervals for full blood counts, numbers and activation status of blood leukocytes (using flow cytometry). At the end of the study, all mice will also be examined for creatinine/BUN levels, spleen leukocyte counts and activation status, as well as histological severity of glomerular and interstitial lesions in their kidneys. Statistical analyses will be carried out to determine if the apogossypol treated mice have significantly reduced autoantibodies and leukocyte numbers/activation (primary outcome measures), or renal disease (secondary outcome measure). Finally, flow-sorted leukocyte populations from both study groups will be examined for the phosphorylation status of BCL-2, BCL-$x_L$, AKT, mTOR, Erk1,2, p38, CDK1/2, and NFkB, to ascertain if BCL-2 blockade also dampens other hyperactivated signaling pathways in lupus.

Treatment Studies

[The same two genetically diverse strains, NZB/NZW F1 and MRL/lpr would be subjected to treatment studies from the age of 5 mo (once they are positive for anti-nuclear autoantibodies and become proteinuric), to the age of 7 months, i.e., for a 2 month period. 20 mice of each strain will receive apogossypol, whereas another 20 age/gender matched females will receive the vehicle ("placebo group"). Mice will be given from between about 0.2 μmol/kg to about 1.0 μmol/kg per day. The route of administration may be oral. However, intravenous administration can also be used. All mice will be tested to ensure they are positive for anti-nuclear autoantibodies at the beginning of the study. In one example, 10 mice will be sacrificed immediately after the treatment period, to examine for splenic leukocyte numbers/activation, whereas the remaining 10 mice in each group will be followed up till death (in order to ascertain the impact of apogossypol on mortality).

The mice will be monitored at fortnightly intervals for serum autoantibody levels and 24-hour urine protein levels, and at monthly intervals for full blood counts, numbers and activation status of blood leukocytes (using flow cytometry). At the end of the study, all mice will also be examined for creatinine/BUN levels, spleen leukocyte counts and activation status, as well as histological severity of glomerular and interstitial lesions in their kidneys. Statistical analyses will be carried out to determine if the apogossypol treated mice have significantly reduced autoantibodies, mortality and leukocyte numbers/activation primary outcome measures), or renal disease (secondary outcome measure). Finally, flow-sorted leukocyte populations from both study groups will be examined for the phosphorylation status of BCL-2, BCL-$x_L$, AKT, mTOR, Erk1,2, p38, CDK1/2, and NFkB, to ascertain if BCL-2 blockade also dampens other hyperactivated signaling pathways in lupus.

Follow up studies will include: assessing the impact of BCL-2 blockade on selected lupus checkpoints, assessing whether the combined use of apogossypol and other conventional drugs might yield better therapeutic efficacy with reduced side-effects, assessing the level of generalized immunosuppression due to apogossypol, and assessing the level of BCL-2 family member activation in human lupus.

Example 16

Prevention of Experimental Autoimmune Encephalomyelitis (EAE) in the Murine Model of Multiple Sclerosis This example illustrates a proposed study to examine the effect of apogossypol treatment on development of both active and passive EAE in the murine model of multiple sclerosis.

Experimental allergic encephalomyelitis (EAE) is a T cell mediated autoimmune disease of the central nervous system (CNS). Disease can be induced in susceptible strains of mice by immunization with CNS myelin antigens or alternatively, disease can be passively transferred to susceptible mice, such as SJL/J mice, using antigen stimulated CD4+ T cells (Pettinelli, J. *Immunol.* 127, 1981, p. 1420). EAE is widely recognized as an acceptable animal model for multiple sclerosis in primates (Alvord et al. (eds.) 1984. Experimental allergic encephalomyelitis—A useful model for multiple sclerosis. Alan R. Liss, New York).

Prevention Studies

Female SJL/J mice would be subjected to preventative studies from the age of 7 to 10 weeks, i.e., for a 2 month period. In one example, 10 mice will receive apogossypol, whereas another 10 age/gender matched females will receive the vehicle ("placebo group"). Although 10 mice will be tested initially, these numbers could easily be ramped up following the power analysis conducted using the initial set of data obtained. Mice will be given from between about 0.2 µmol/kg to about 1.0 µmol/kg per day. The route of administration will be oral. However, intravenous administration can also be used.

a) Active EAE.

Active EAM would be induced by immunization of female SJL/J mice with, for example, about 800 µg of mouse spinal cord homogenate ("MSCH") in complete Freund's adjuvant ("CFA") on days zero and seven; following the procedure described in Racke et al., *J. Neuroimmunol.*, Vol 46:175-184, (1993).

b) Passive EAE.

Passive EAE would be induced by adoptive transfer of myelin basic protein ("MBP")-sensitized T lymphocytes as follows: female SJL/J mice (four- to six-weeks-old) were immunized on days zero and seven with 400 µg of MBP in CFA. On day 14 the regional draining lymph node cells and spleen are harvested and cultured. The cells are cultured at about $4 \times 10^6$ cells/well in, for example, RPMI 1640 (Gibco, Gaithersburg, Md.) containing 10% fetal bovine serum (Hyclone Labs, Logan, Utah), 2 mM L-glutamine (Gibco, Gaithersburg, Md.), $5 \times 10^{-5}$ M 2-mercaptoethanol (Gibco, Gaithersburg, Md.), 1% penicillin/streptomycin (Gibco, Gaithersburg, Md.), and 100 µg/ml of MBP. After four days, viable T cell blasts are harvested, washed, and injected intraperitoneally into recipient mice ($1 \times 10^7$ to $1.5 \times 10^7$ cells in 500 µl of PBS).

The mice will be monitored at daily intervals for clinical signs of EAE and scored on a scale of 0 to 3 as follows: 0.5—Distal limp tail; 1.0—Complete limp tail; 1.5—Limp tail and hind limb weakness (unsteady gait); 2.0—Partial hind limb paralysis; 3.0—Complete bilateral hind limb paralysis. At the end of the study, all mice will also be examined for lymphocyte infiltration and demyelination of the spinal cord. Statistical analyses will be carried out to determine if the apogossypol treated mice have significantly reduced disease severity, inflammation and/or demyelination.

Example 17

Prevention and Treatment of Diabetes in the NOD/SCID Mouse Model

This example illustrates generally the proposed use of the NOD/SCID mouse model to test the ability of apogossypol to prevent or treat diabetes.

The non-obese diabetic (NOD) mouse is a model for autoimmune disease, in this case insulin-dependent diabetes mellitus (IDDM), which main clinical feature is elevated blood glucose levels (hyperglycemia). The elevated blood glucose levels are caused by the immune-mediated destruction of insulin-producing β cells in the islets of Langerhans of the pancreas. This destruction is accompanied by a massive cellular infiltration surrounding and penetrating of the islets (insulitis) by a heterogeneous mixture composed of a CD4+ and CD8+ T lymphocytes, B lymphocytes, macrophages and dendritic cells.

The NOD mouse model for inflammation was generally described previously. Female NOD mice spontaneously develop an IDDM-like disease with destruction of the β cells in the pancreas and spilling of glucose into the urine beginning around 12-14 weeks of age. A typical longitudinal histological examination of the NOD pancreas demonstrates infiltrating cells surrounding the blood vessels at 3-4 weeks of age, but the islets are typically still clear at 6-7 weeks. Infiltrating cells than reach the islets, either surrounding them or accumulating at one pole. Between 10 and 12 weeks, the infiltrating cells penetrate into the islets and the islets become swollen with lymphocytes. The easiest and most reliable way to detect the onset of diabetes in these mice is to test for glucose levels in the blood.

Diabetes can be assessed by measurement of venous blood using, for example, an Abbott Medisense Precision Q.I.D. glucometer and also monitored for glucosuria (Gluketur Test; Boehringer Mannheim, Mannheim, Germany). Animals will be considered diabetic after two consecutive glucose measurements of higher than about 13.75 mmol/l (250 mg/dl). Onset of diabetes will be dated from the first consecutive reading. In instances of sustained hyperglycemia of >33 mmol/l animals will be sacrificed to avoid prolonged discomfort.

Prevention Studies

NOD/LtJ mice (Jackson Laboratories) would be subjected to preventative studies from the age of about 8-10 weeks, for a 2 month period. Mice will be checked to ensure they are negative for IDDM-like disease symptoms at the beginning of the study. In one example, 10 will receive apogossypol, whereas another 10 age/gender matched females will receive the vehicle ("placebo group"). Although 10 mice will be tested initially, these numbers could easily be ramped up following the power analysis conducted using the initial set of data obtained. Mice will be given from between about 0.2 µmol/kg to about 1.0 µmol/kg per day. The route of administration may be oral; intravenous administration can also be used.

The mice will be monitored at daily intervals for blood glucose levels and 24-hour urine protein and glucose levels, and at monthly intervals for full blood counts, numbers and activation status of blood leukocytes (using flow cytometry). At the end of the study, all mice will also be examined for insulin levels, presence of CD4+ and CD8+ T lymphocytes, B lymphocytes, macrophages and dendritic cells in the pancreas, as well as general morphology of the pancreas. Statistical analyses will be carried out to determine if the apogossypol treated mice have significantly delayed onset of diabetes.

Treatment Studies

NOD/LtJ mice would be subjected to treatment studies beginning at about 10-12 weeks of age. 20 mice will receive apogossypol, whereas another 20 age/gender matched females will receive the vehicle ("placebo group"). Mice will be given from between about 0.2 µmol/kg to about 1.0 µmol/kg per day. The route of administration will be oral; intravenous administration can also be used. All mice will be tested to ensure they are positive for IDDM-like disease (i.e., two consecutive glucose measurements of higher than about 13.75 mmol/l (250 mg/dl)) at the beginning of the study. In one example, 10 mice will be sacrificed immediately after the treatment period, to examine for pancreas morphology and presence of lymphocytes in the pancreas, whereas the remaining 10 mice in each group will be followed up till death (in order to ascertain the impact of apogossypol on mortality).

The mice will be monitored at daily intervals for blood glucose levels and 24-hour urine protein and glucose levels, and at monthly intervals for full blood counts, numbers and activation status of blood leukocytes (using flow cytometry).

At the end of the study, all mice will also be examined for insulin levels, presence of CD4+ and CD8+ T lymphocytes, B lymphocytes, macrophages and dendritic cells in the pancreas, as well as general morphology of the pancreas. Statistical analyses will be carried out to determine if the apogossypol treated mice have significantly reduced blood glucose levels, urine glucose levels, and mortality and leukocyte numbers/activation.

Follow up studies will include: assessing the impact of BCL2 blockade on selected IDDM-like disease checkpoints, assessing whether the combined use of apogossypol and other conventional drugs might yield better therapeutic efficacy with reduced side-effects, assessing the level of generalized immunosuppression due to apogossypol, and assessing the level of BCL2 family member activation in human diabetes.

Example 18

Studies of Apogossypol Activity and Toxicity in BCL-2 Transgenic Mice

The toxicity and efficacy studies were conducted in mice to compare gossypol and apogossypol. At daily dose of 0.12 mmol/kg p.o., % mortality in gossypol-treated Balb/c mice was 100% by the end of week 3. Gossypol-treated mice developed the following toxicities: GI toxicity partial paralytic ileus), hematological toxicity (lymphopenia), hepatotoxicity (elevation of serum levels of ALT and AST, weight loss and cardiac toxicity, and cause of death was cardiac failure in gossypol-treated mice.

Figure 5A:
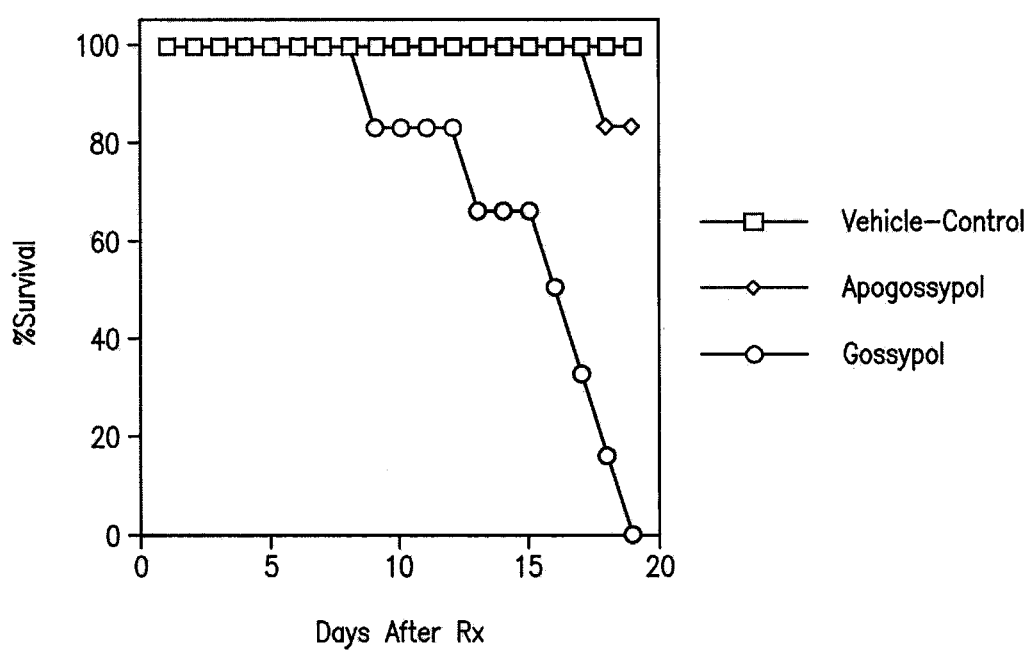
FIGS. 5A and 5B depict toxicity profiles of gossypol vs. apogossypol.
Figure 5B:
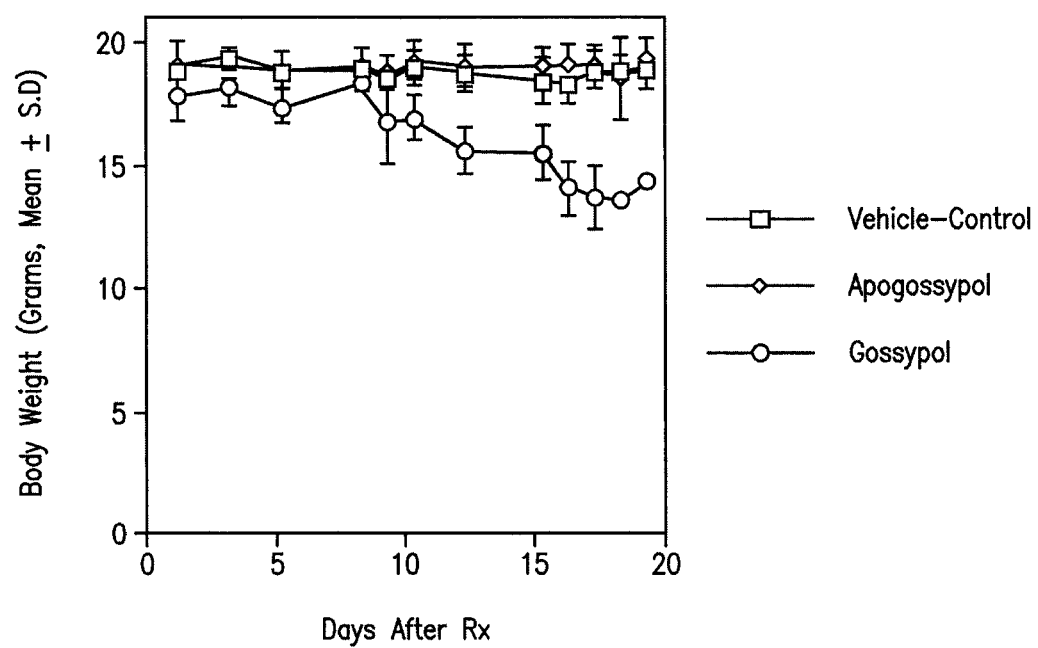

FIGS. 5A and 5B further illustrate toxicity profiles of gossypol vs. apogossypol. FIG. 5A shows % survival in young, healthy Balb/c mice (7-weeks-old females, 6 mice per group). Mice were orally administered with apogossypol, gossypol or vehicle-control at a daily dose of 0.12 mmol/kg, QDx5 for three weeks. % survival dropped to 0 by the end of 3 weeks of treatment with gossypol, whereas % survival remained high among groups treated with apogossypol or vehicle-control.

FIG. 5B illustrates changes in body weight, which were monitored throughout the entire period of treatments with apogossypol, gossypol or vehicle-control at a daily dose of 0.12 mmol/kg, QDx5 for three weeks. Data expressed in grams (Mean±Standard Deviation).

As can be seen from the data provided by FIGS. 5A and 5 B, apogossypol was less toxic than gossypol in all these categories and apogossypol did not induce any abnormal changes in E.C.G. pattern throughout the entire period of treatment. Gossypol-treated mice became lethagic with scruffy hair, whereas apogossypol or vehicle-control-treated mice remained active and apparently healthy without weight loss throughout the treatment period. Apogossypol-treated mice as well as vehicle-control mice (0.12 mmol/kg ascorbic acid in sesame oil) revealed normal E.C.G.-pattern, using 2-electrodes, by the use of MP150 Biopac system (the third electrode=ground). In addition, apogossypol-treated mice as well as vehicle-control mice exhibited normal bowel movement in ultrasound imaging-Cinema (300 frames), while no weight loss was noted during the entire course of treatment. One of 6 apogossypol-treated mice was found dead on day 18 of treatment. This mouse was apparently healthy until the day before death, and cause of death is unknown at this moment.

Apogossypol was well-tolerated in nude mice grafted with SCLC H146 cell line at daily dose of 0.24 mmol/kg, p.o. (no fatality and no weight loss), and anti-tumor effect of apogossypol was demonstrated. Ascorbic acid-stabilized apogossypol was stable for 2.5 weeks when stored at 4° C. or at room temperature under nitrogen gas or air, with or without light.

Toxicity

It was determined that apogossypol is less toxic than gossypol. The toxicities of gossypol and apogossypol were compared in normal female Balb/c mice. Preliminary maximum tolerated dose (MTD) studies suggested that apogossypol was less toxic than gossypol whether delivered orally or by intraperitoneal injection. Previous NCI-sponsored studies determined that racemic gossypol and (–)gossypol are non-lethal and show anti-tumor activity when dosed orally at 0.06 mmol/kg daily for up to 21 days. Thus, orally administered gossypol and apogossypol were compared at twice this dose; animals were dosed with 0.12 mmol/kg. Ascorbic acid was employed as a control, because apogossypol is formulated at 1:1 molar ratio with this weak acid, which renders the compound stable upon storage. Compounds or vehicle control were dosed 15 times over 3 weeks, giving compounds daily for 5 consecutive days (Monday-Friday), resting on weekends.

BCL-2 Transgenic Mice

Transgenic mice expressing BCL-2 have been described as the B6 line. The BCL-2 transgene represents a mini-gene version of a t(14;18) translocation in which the human BCL-2 gene is fused with the immunoglobulin heavy-chain (IgH) locus and associated IgH enhancer. The transgene was propagated on the Balb/c background.

Patient Specimens

Peripheral blood mononuclear cells (PBMC) from patients with CLL were obtained from the CLL Research Consortium (CRC) tissue bank (San Diego, Calif.). The blood samples were collected after obtaining informed consent. PBMC were isolated by density gradient centrifugation using Histopaque 1077 (Sigma, St. Louis, Mo. 63178). All patients met the NCI IWCLL criteria for diagnosis of CLL. The samples used contained ≥95% CD19 and CD5 positive cells, as assessed by flow cytometry. CLL samples were cultured in RPMI media containing 10% fetal bovine serum (FBS) (HyClone, Logan, Utah 84321 or Mediatech Inc., Herndon, Va. 20171) at 37° C. in 5% CO2:95% air.

Gossypol and Apogossypol Preparation and Formulation

Apogossypol (NSC736630) was co-crystallized with ascorbic acid at 1:1 molar ratio. Gossypol NSC19048) was lyophilized in acetic acid form. Both compounds were provided by NCI-DTP (RAID-program). Compounds were dissolved in 100% sesame oil just before oral administration. Vehicle-control consisted of corresponding concentration of ascorbic acid suspended in 100% sesame oil.

Mouse Experiments

Gossypol and apogossypol were administered orally to mice daily at doses of 0.06 mmol/kg or 0.12 mmol/kg, using a straight-type oral gavage needle (18G-3" Straight 2.25 mm ball, Braintree Scientific, Inc.). The volume of administration was 10 ml/kg; i.e., typically 0.2 mL per 20 gm mouse. Normal Balb/c mice of 7 to 8 weeks of age at the initiation of the study were employed for toxicity studies, while BCL-2 transgenic mice on Balb/c background of >6 months age were employed for efficacy studies. Age-matched, sex-matched mice were typically dosed 5 times weekly, using a regiment of daily dosing 5 consecutive days (Monday through Friday), followed by resting for 2 days, before resuming dosing. For BCL-2 transgenic mice, spleen-size was longitudinally monitored either by Ultrasound Imaging (Visualsonics) weekly and by physical examination using a digital caliper. At conclusion of treatments, mice were sacrificed via intra-peritoneal (i.p.) injection of 0.7 ml of Avertin and whole blood was collected into Yellow-Top Serum Separator tubes (Becton Dickinson Vacutainer Systems Becton Dickinson and Company, Franklin Lakes, N.J. 07417-1885). Spleens were removed and weighed.

Hematology Studies

Whole blood (250 μl) was collected in EDTA-coated glass tubes (purple top; MICROTAINER Brand Tube with EDTA, Catalogue #365973, Becton, Dickinson and Company, New Jersey 07417-1885) via either cardiac puncture or severing the brachial artery of anesthetized mice. After thorough mixing, specimens were analyzed using a VetScan HM2 (Abaxis Inc., Union City, Calif. 94587) hematology analyzer, measuring white blood cell count (WBC), red blood cell count (RBC), platelet (PLT) count, leukocyte differential (including % lymphocyte, % monocyte and % granulocyte), hematocrit (Ht), and hemoglobin (Hb).

Figure 6A:
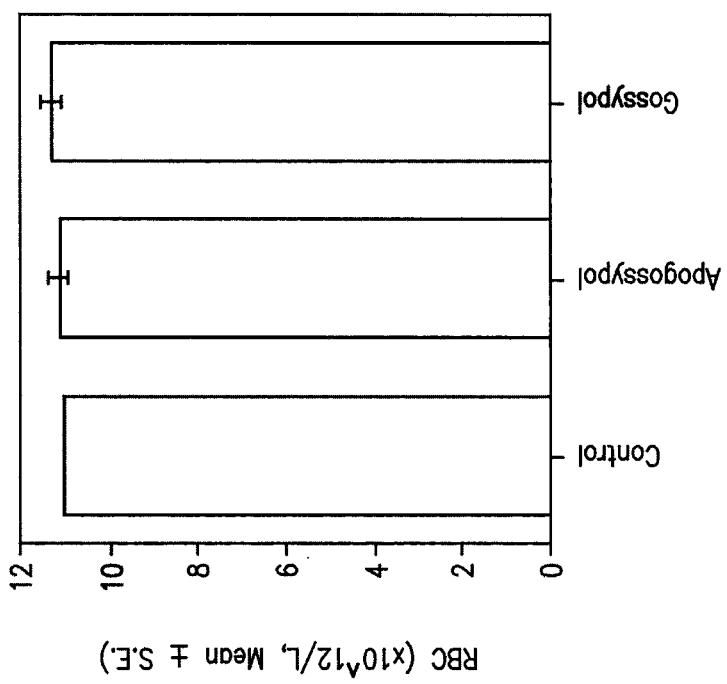
FIGS. 6A-6C depict hematological profiles of mice treated with apogossypol or gossypol.
Figure 6A:
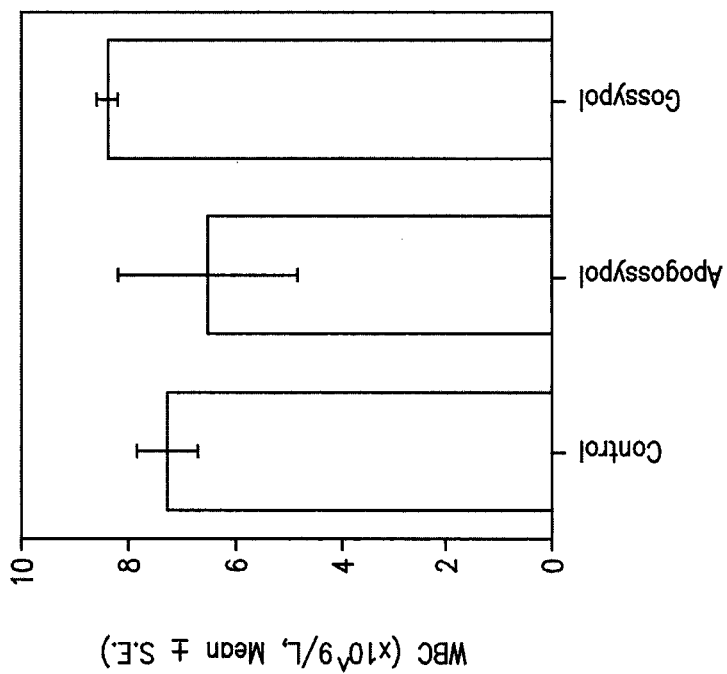
Figure 6B:
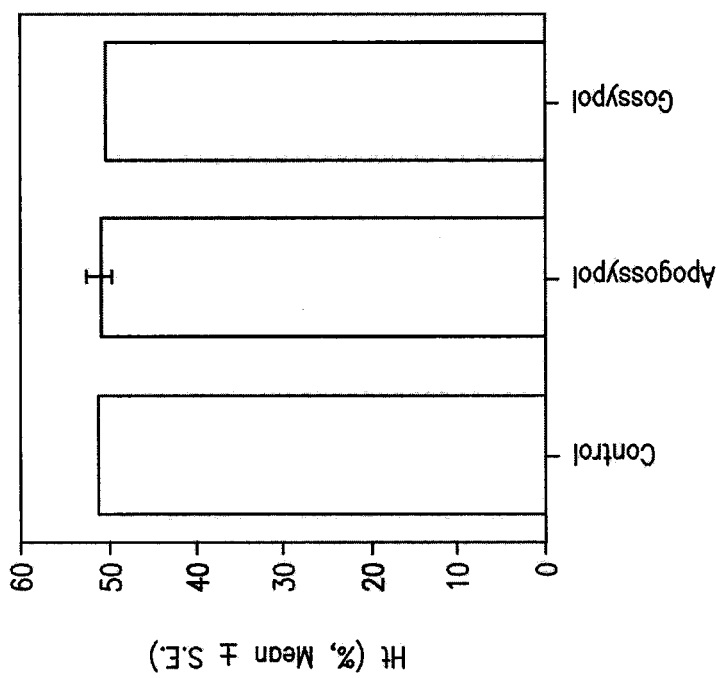
Figure 6B:
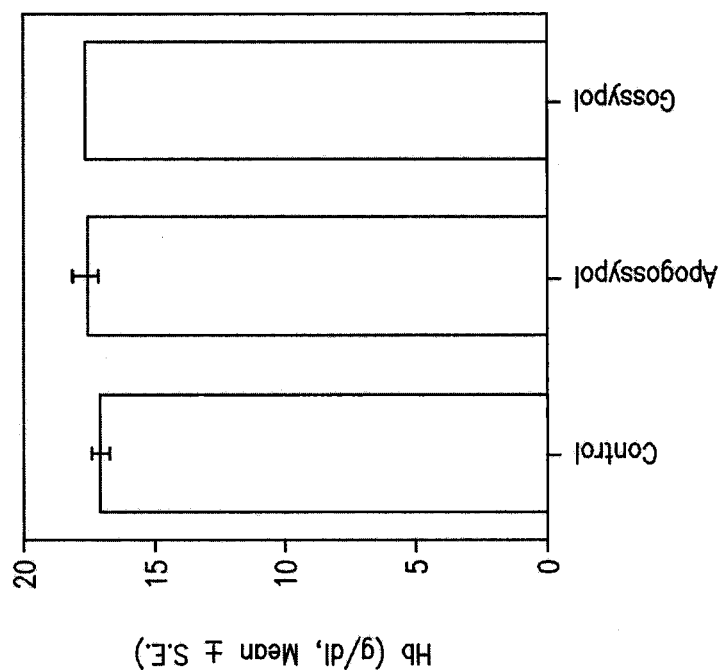
Figure 6C:
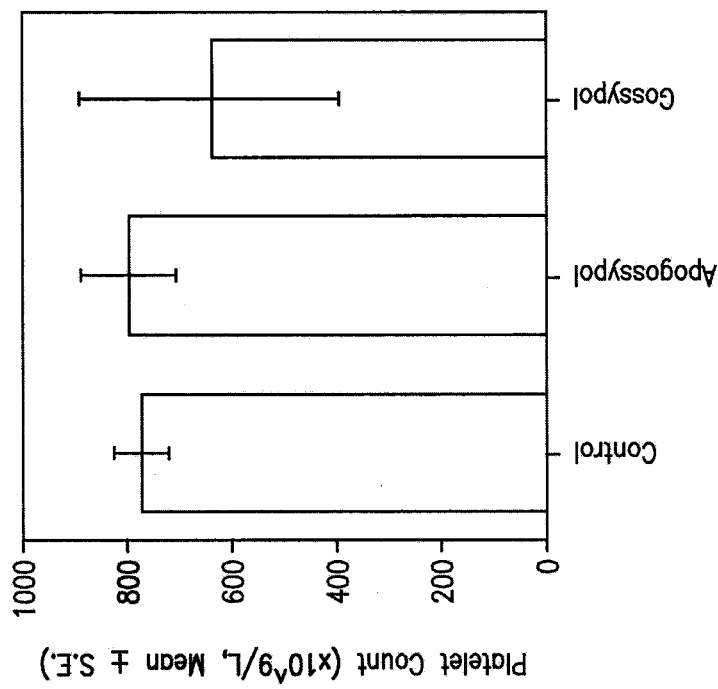
Figure 6C:
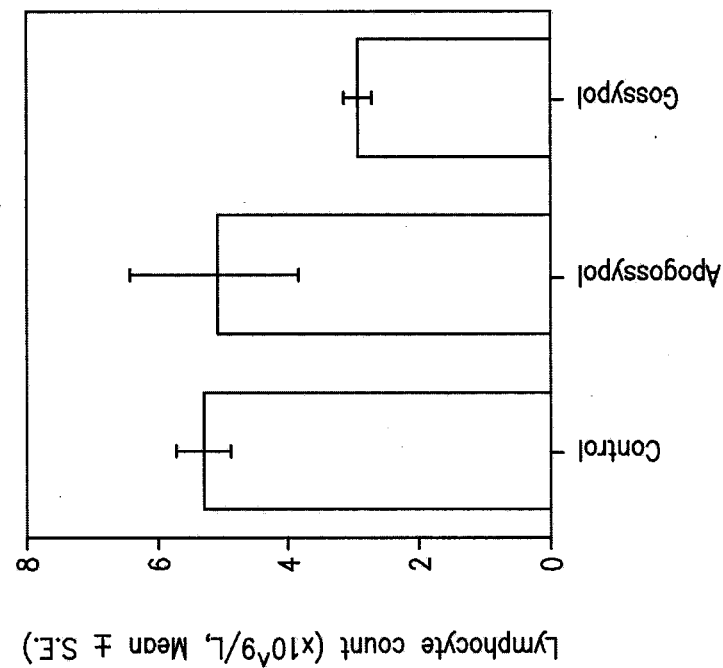

FIGS. 6A-6C illustrate hematological profiles of mice treated with apogossypol or gossypol. Mice were orally administered with apogossypol, gossypol or vehicle-control at a daily dose of 0.12 mmol/kg, QDx5 for three weeks (6 mice per group). Hematological profiles were analyzed by the use of an automated HM2 hematology analyzer (Abaxis Inc., Union City, Calif. 94587) at conclusion of therapy with vehicle-control or apogossypol or at the time of death in mice treated with gossypol.

FIG. 6A shows WBC (left Panel) and RBC (right panel). As can be seen, both WBC and RBC were unaffected by treatments with gossypol and apogossypol. FIG. 6B shows data for hemoglobin (Hb) (left panel) and for hematocrit (Ht) (right panel). As can be seen, both Hb and Ht were unaffected by treatments with gossypol and apogossypol. Finally, FIG. 2C provides data for lymphocyte count (left panel) and for platelet count: (right panel). As can be seen, gossypol induced lymphopenia, whereas apogossypol did not induce lymphopenia in Balb/c mice.

Serum Chemistry

Approximately 500 μl of whole blood was collected in glass tubes (yellow-top; MICROTAINER Brand, Serum Separator Tube, Catalogue #365956, Becton Dickinson and Company, Franklin Lakes, N.J. 07417-1885) and kept on ice for 30 minutes, then centrifuged at 12,000 r.p.m. (Eppendorf Centrifuge 5415C) for 2 minutes to separate serum from cells and fibrin clot. The resulting serum specimens were analyzed using an automated blood chemistry analyzer ("COBAS MIRA Classic"; Roche, Indianapolis, Ind. 46250-0414) to measure alanine aminotransferase (ALT) and aspartate aminotransferase AST), blood urea nitrogen (BUN), and Creatine.

Figure 7:
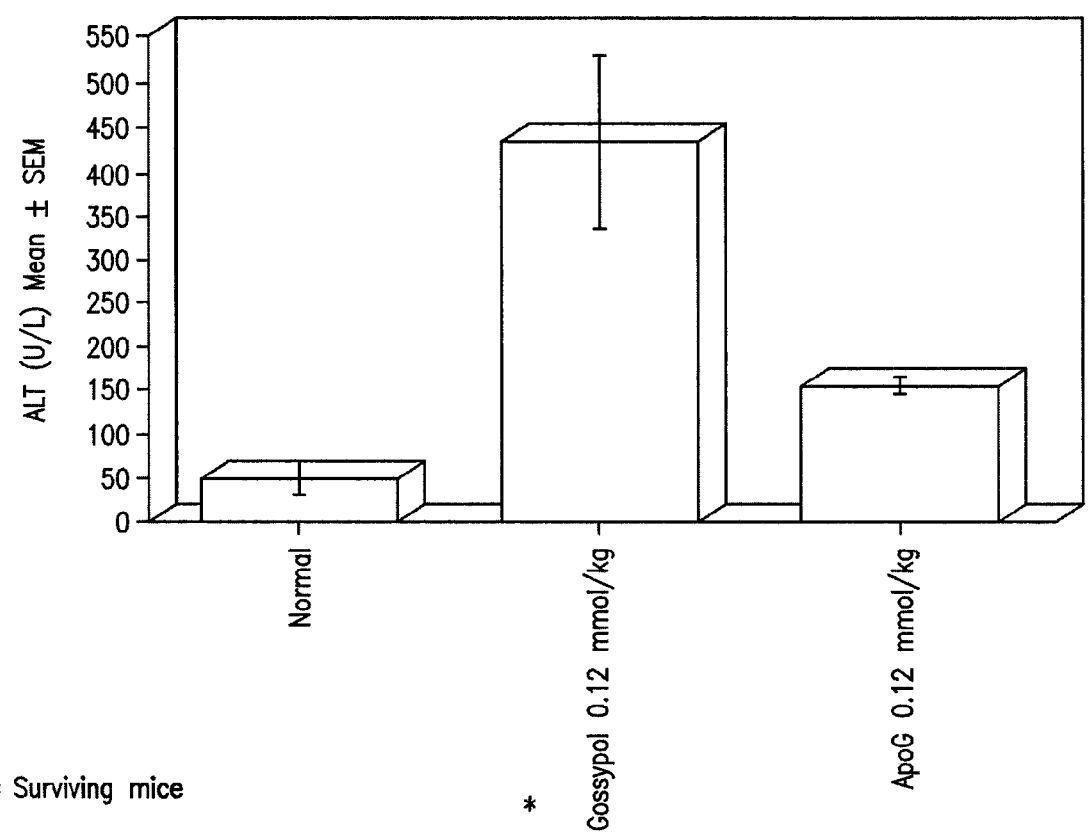
FIG. 7 depicts representative blood chemistry profiles of mice treated with apogossypol or gossypol.

FIG. 7 provides the experimental data illustrating representative blood chemistry profiles of mice treated with apogossypol or gossypol. Mice were orally administered with apogossypol, gossypol or vehicle-control at a daily dose of 0.12 mmol/kg, QDx5 for three weeks (6 mice per group). As can be seen, gossypol induced elevation of serum levels of ALT and apogossypol was less hepato-toxic than gossypol.

Ultrasound Imaging

Stomach and intestines were examined also imaged by ultrasound for evidence of dilation, an indication of GI toxicity. Briefly, mice were anesthetized using a mixture of isofluorane (5%) and oxygen gas (95%), restrained on a heated table using Aquagel Lubrication Gel (Parker Laboratories, Inc., Fairfield, N.J. 07004), and abdominal hair was removed with a chemical depilation agent (Nair™ Hair Removal, Church & Dwight Co., Inc., Princeton, N.J. 08543). Aquasonic 100 Ultrasound Transmission Gel (Parker Laboratories, Inc., Fairfield, N.J. 07004) was applied to the abdomen prior to imaging using a high-frequency probe to assess gas and intestinal distention.

Cardiac Toxicity

Immediately after ultrasound imaging, electrocardiogram (ECG) analysis of anesthetized mice was performed using a MP150 Biopack System.

Histology

Vital organs, including liver, kidneys, spleen, heart, stomach, small intestines, large intestines and lungs, were fixed in z-FIX solution (COMPANY?) for 3 days, rinsed 3 times with phosphate-buffered saline (PBS) [pH 7.4], and then embedded in paraffin-blocks. Thin sections were cut (0.5 um), stained with hematoxylin-eosin (H&E), and evaluated by light microscopy for histological abnormalities. In addition, unstained sections were analyzed by the terminal deoxynucleotidyl transferase end-labeling (TUNEL) method to stain cells with DNA fragmentation indicative of apoptosis.

Splenocyte Isolation

Spleens were excised from sacrificed mice and cell suspensions treated with a mouse erythrocyte lysing kit (R & D Systems). Total splenocyte count was determined by typan blue dye exclusion assays using hemocytometers. The percentage of B-lymphocytes was determined by fluorescence activated cell sorter (FACS) analysis SACS-CANTO, Bectin-Dickinson Inc., Mountain View, Calif.) following staining cells with Phyco-Erytrin (PE)-conjugated anti-CD19 or -B220 antibodies (Becton Dickinson, San Jose, Calif. 95131).

Cell Culture and Cytotoxicity Studies

Splenocytes were suspended at $1 \times 10^6$ cells/mL in RPMI 1640 medium (Mediatech Inc., Herndon, Va. 20171) containing 10% fetal bovine serum (Mediatech Inc., Herndon, Va. 20171) and Penicillin/Streptomycin (Mediatech Inc., Herndon, Va. 20171). Human B-CLL cells and 3 B-NHL cell lines, including RS11846, DOHH2 and 380 cells, were cultured in RPMI 1640 medium (Mediatech Inc., Herndon, Va. 20171) containing 10% fetal bovine serum (Mediatech Inc., Herndon, Va. 20171) and Penicillin/Streptomycin (Mediatech Inc., Herndon, Va. 20171). Cells were cultured with various concentrations of Gossypol, ApoGossypol, or ascorbic acid for 1-2 days. The percentage of viable cells was determined by Annexin V- and propidium iodide (PI)-labeling, using an Apoptosis Detection kit (BioVision Inc.), analyzing stained cells by flow cytometry (FACSort; Bectin-Dickinson, Inc.;

Mountain View, Calif.). Cells that were annexin-V-negative and PI-negative were considered viable.

Figure 8:
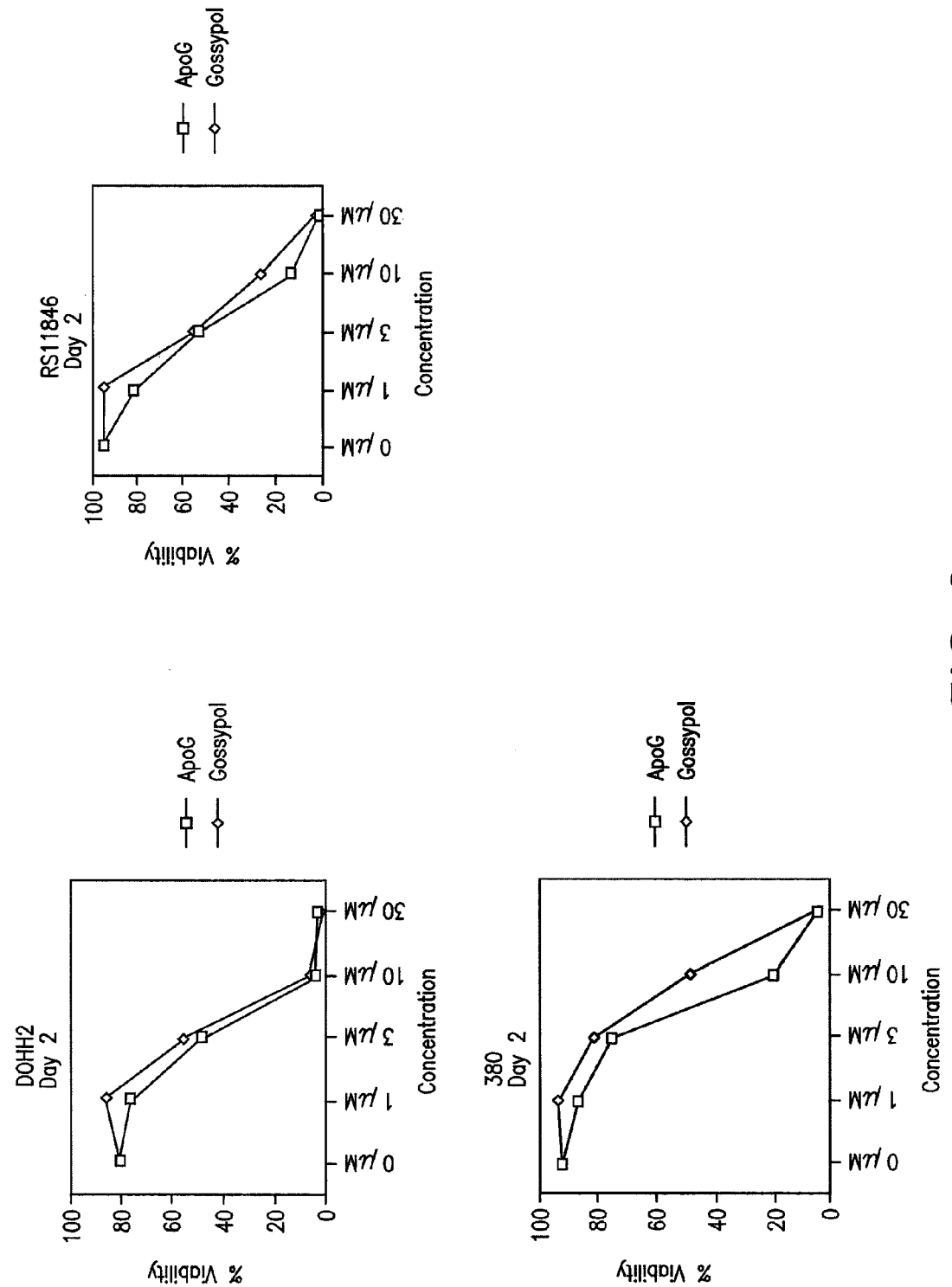
FIG. 8 depicts a comparison of apoptosis induction of NHL B-cell lines, including DOHH2, RS11846 and 380, by apogossypol and gossypol.

FIG. 8 provides the experimental data illustrating a comparison of apoptosis induction of NHL B-cell lines, including DOHH2, RS11846 and 380, by apogossypol and gossypol. NHL B-cell lines, including DOHH2, RS11846 and 380, were cultured in RPMI medium containing 10% fetal bovine serum (FBS) for 48 hours, in the absence and presence of various concentrations of gossypol and apogossypol as indicated in the figures.

After 48 hours of incubation, % viability was determined by FACSort after staining cells by the use of an Annexin V-FITC/PI Apoptosis Detection kit (BioVision Inc.). Viable cells were defined by Annexin V-negative, PI-negative cells. DOHH2 and RS11846 cell lines were slightly more sensitive to gossypol and apogossypol in vitro with IC50 of approximately 3 µM, whereas 380 cell line was slightly more resistant to gossypol and apogossypol. In all three NHL B-lymphoma cell lines, apogossypol was slightly more potent than gossypol, but their potencies were roughly comparable.

Figure 9:
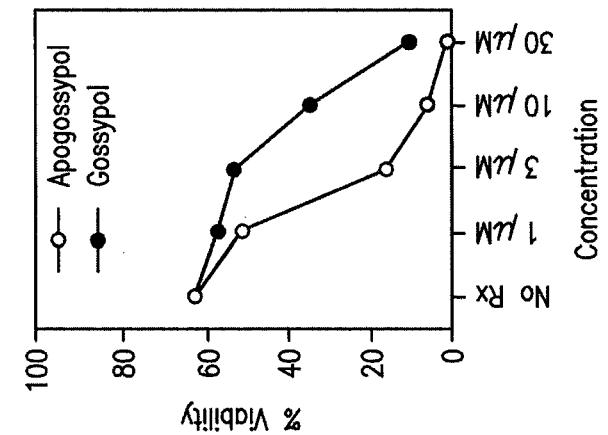
FIG. 9 depicts a comparison of activity of gossypol and apogossypol against cultured murine B-cells from transgenic mice: BCL-2 vs. BCL-2/TRAF2DN.
Figure 9:
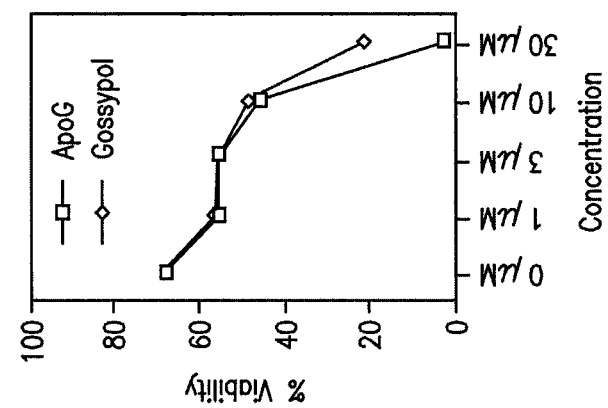
Figure 9:
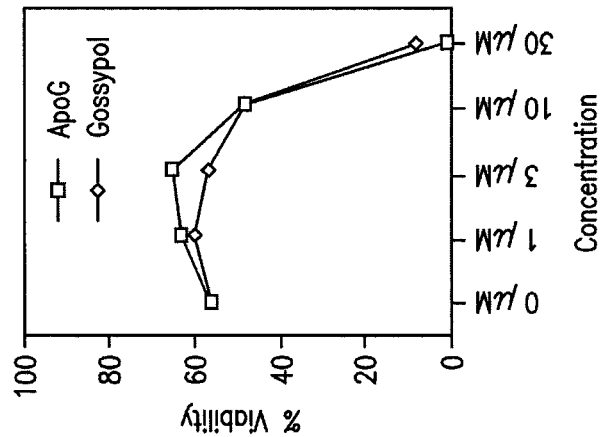

FIG. 9 provides the experimental data illustrating a comparison of activity of gossypol and apogossypol against cultured murine B-cells from transgenic mice: BCL-2 vs. BCL-2/TRAF2DN. Spleen tissues were removed from BCL-2 transgenic mice and BCL-2/TRAF2DN mice, and splenocytes were isolated by the use of a mouse erythrocyte lysing kit (R & D Systems) according to the manufacturer's manual.

Splenocytes were cultured in RPMI medium containing 10% fetal bovine serum (FBS) for 18 hours, in the absence and presence of various concentrations of gossypol and apogossypol as indicated in the figures. After 18 hours of incubation, % viability of splenocytes was determined by FACSort after staining cells by the use of an Annexin V-FITC/PI Apoptosis Detection kit (BioVision Inc.). Viable cells were defined by Annexin V-negative, PI-negative cells. In BCL-2 transgenic mouse, apogossypol was several-fold more potent than gossypol in induction of apoptosis against cultured B-cells with IC50 of roughly 1-2 µM for apogossypol vs. 10 µM for gossypol. In contrast, murine B-cells from Bcl-2/TRAF2DN mice were roughly 10-fold more resistant to both apogossypol and gossypol than Bcl-2 transgenic mice.

Figure 10:
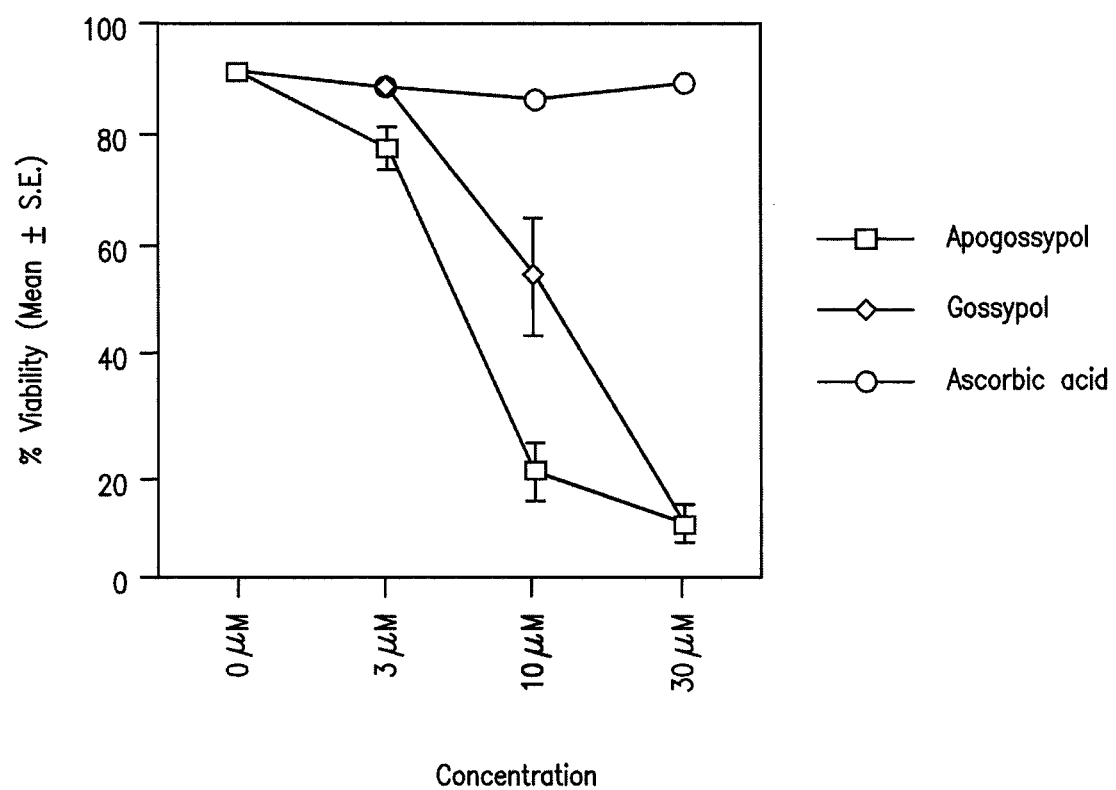
FIG. 10 depicts a comparison of apogossypol and gossypol induction of apoptosis of cultured CLL B-cells.

FIG. 10 provides the experimental data illustrating a comparison of apogossypol and gossypol induction of apoptosis of cultured CLL B-cells. CLL samples were incubated in RPMI media containing 10% fetal bovine serum (FBS) at 37° C. with 5% CO2 for 48 hours, in the absence or presence of various concentrations of gossypol and apogossypol as indicated in the figures.

After 48 hours of culture, % viability was determined by FACSort after staining cells by the use of an Annexin V-FITC/PI Apoptosis Detection kit (BioVision Inc.). Viable cells were defined by Annexin V-negative, PI-negative cells. Apogossypol was approximately 3-fold more potent than gossypol against cultured CLL B-cells in vitro. There was significant difference in apoptosis induction between apogossypol group and gossypol group p<0.025) by two-way ANOVA analysis.

Figure 11A:
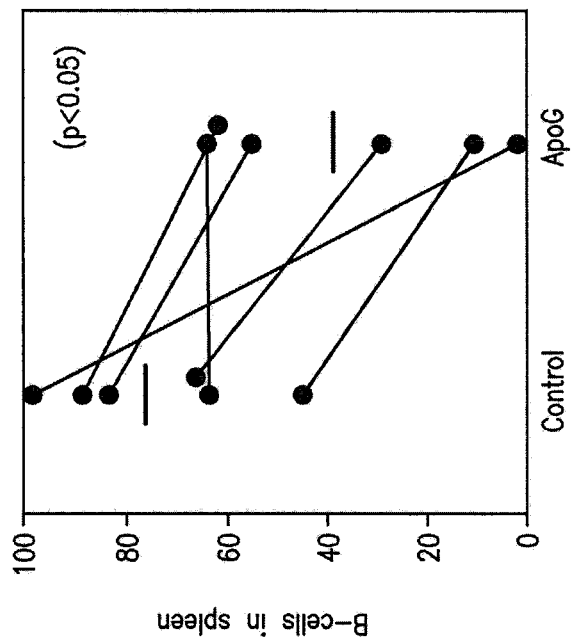
FIGS. 11A and 11B depict apogossypol activity in BCL-2 transgenic mice.
Figure 11A:
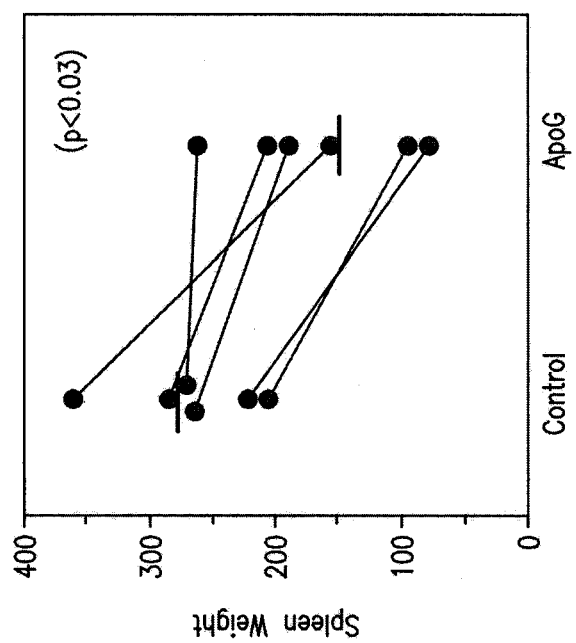
Figure 11B:
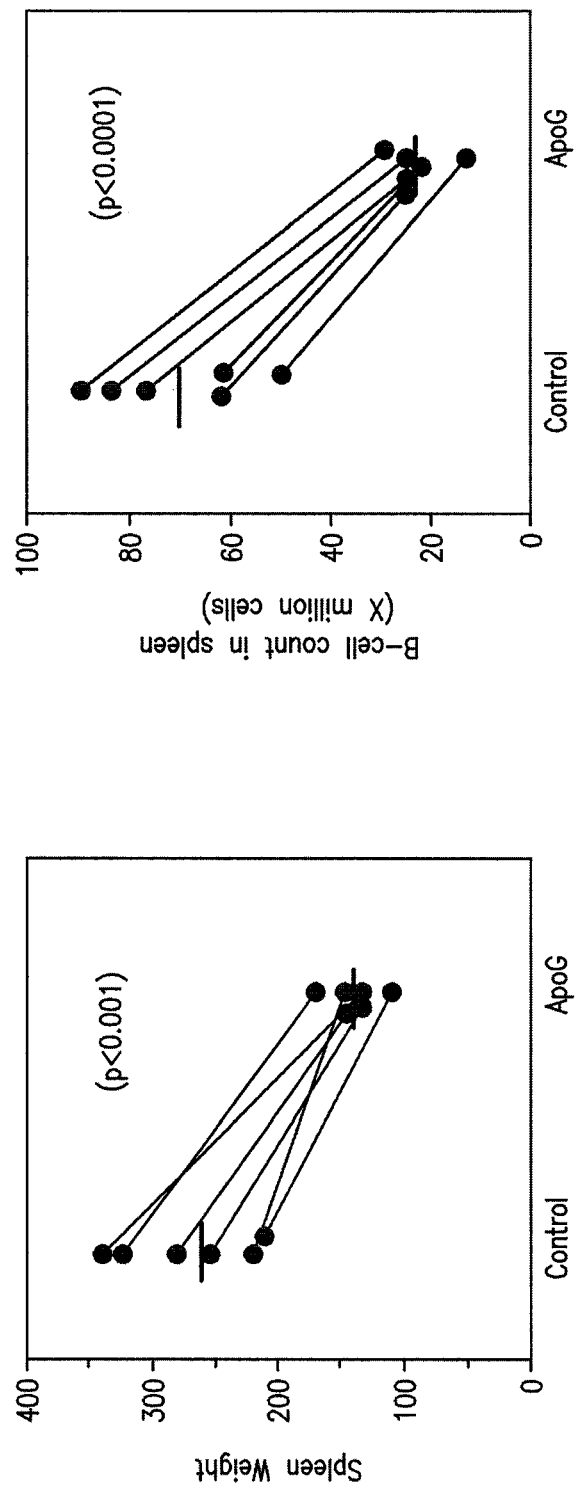

FIGS. 11A and 11B provide the experimental data illustrating apogossypol activity in Bcl-2 transgenic mice. FIG. 11A shows the results of a low dose study (at 0.06 mmol/kg) and FIG. 11B—a high dose study (at 0.12 mmol/kg). Age-matched and sex-matched BCL-2 transgenic mice were used for efficacy studies. BCL-2 transgenic mice spontaneously developed low grade B-cell lymphoma as characterized by splenomegaly, as a function of time. In BCL-2 transgenic mice, the disease progression can be divided into two stages; at the first stage, the disease is characterized by splenomegaly as a result of expansion of B-cells in spleen due to over-expressed BCL-2 in B6 mice, and at the second stage, another genetic hit(s) may strike, resulting in disseminated lymphoma as characterized by bulky lymphadenopathy as well as splenomegaly.

In this study, BCL-2 transgenic mice at the first stage were used for this efficacy study. In a separate study with untreated BCL-2 transgenic mice, wet weight of spleen ranged from 195-mg to 335-mg, and wet weight of spleen was found to be nearly comparable in age-matched, sex-matched BCL-2 transgenic mice. Apogossypol stabilized with ascorbic acid at 1:1 molar ratio, gossypol stabilized with acetic acid at 1:1 molar ratio and vehicle-control (ascorbic acid in 100% sesame oil) were orally administered to BCL-2 transgenic mice once daily (QDX5) for 3 weeks, consecutively. At conclusion of treatment, BCL-2 transgenic mice were sacrificed via intraperitoneal injection of 0.7 ml of avertin (anesthetic solution) and spleen was removed and weighed. Splenocytes were isolated by the use of mouse erythrocyte lysing kit (RD Systems). Total splenocyte count was determined by trypane blue exclusion assays. % B-cell count was determined by FACS analysis after staining cells with CD-5, a B-cell marker. Representative data are shown by FIGS. 11A and 11B.

As can be seen from FIG. 11A, at a low dose of 0.06 mmol/kg, both gossypol and apogossypol were well tolerated and induced shrinkage of splenomegaly, as evidenced by reductions in wet weight of spleen as well as B-cell count in spleen. Apogossypol induced shrinkage of spleen to a significant extent p<0.03 for wet weight of spleen, P<0.05 for splenic B-cell counts), whereas gossypol induced shrinkage of spleen to a considerable extent but not significantly.

As can be seen from FIG. 1B, at a high dose of 0.12 mmol/kg, gossypol was not tolerated in BCL-2 transgenic mice, whereas apogossypol was well tolerated in Bcl-2 transgenic mice at a high dose of 0.12 mmol/kg. Apogossypol induced shrinkage of splenomegaly to a significant extent (p<0.001 for wet weight of spleen, P<0.0001 for splenic B-cell counts). Age-matched, sex-matched BCL-2 transgenic mice were evaluated for shrinkage of spleen after conclusion of apogossypol therapy and spleen size was reduced roughly by half at a daily dose of 0.12 mmol/kg.

Example 19

Evaluation of the Cytotoxic Activity of the Compounds on Human Tumors Cells

This example illustrates the efficacy of gossypol on human tumor cells. To evaluate the cytotoxic activity of the compounds on human tumors cells, their biological activities were tested using XTT dye reduction assays using two breast cancer cell lines: MCF7 (high expressor of BCL-2/BCL-$X_L$) and ZR75-1 (low expresser of BCL-2/BCL-$x_L$). Gossypol is a cytotoxic agent for MCF7 and ZR75-1 cells, reducing cell viability in a dose-dependent manner, with $IC_{50}$ values of 13.2 µM and 8.4 µM, respectively. Purpurogallin, however, did not show appreciable activity in these assays, potentially due to its hydrophilic character (ClogP-0.7).

Consistent with this observation, a purpurogallin derivative 5D1 that is predicted to have better cell-membrane permeability properties (based on its ClogP of ~2.5) reduced cell viability in a dose-dependent manner, with $IC_{50}$ value of ~50 µM the ZR75-1 cell line (not shown). Therefore, the cellular activities of the compounds were evaluated in HeLa cells, which are known to be less selective for compounds uptake. The inhibition data obtained with HeLa cells viability assays parallel the in vitro binding data with BCL-$X_L$, with a correlation coefficient of r=0.9 (p=0.001).

Docking studies with FlexX software (Kramer et al., *Proteins*, 37:228 (1999)) implemented in Sybyl (TRIPOS) using the BCL-$X_L$ conformation found in the complex with Bak-peptide showed an optimal location for gossypol in the deep hydrophobic cleft normally occupied by the Bak helical BH3 peptide in the complex. Both the (+) and the (−) stereoisomers of gossypol were docked, as these exhibited different activity in previous cell-based assays which showed that (−) gossypol is ten times more effective than (+) gossypol as a cytotoxic agent. The goodness of the fit as measured by a scoring function, and the intermolecular energy after minimization with the DOCK routine of Sybyl, was considerably better for (−) gossypol (−32.7 Kcal/mol) versus (+) gossypol (−25 Kcal/mol), in agreement with these observations. The overall positioning of both stereoisomers of Gossypol is very similar.

Fluorescence Polarization Assays (FP A)

FP A assays were conducted with a fluorescein-labeled Bad peptide (NL W AAQRYGRELRRMSD-K(FITC)-FVD) (Synpep Corporation, Dublin, Calif.) using a LJL Analyst HT Molecular Devices Co., Sunnyvale, Calif.). Dilution buffer for all stocks and samples was 50 µM Tris-Bis pH 7.4, 0.01% bovine gamma globulin. A series of two-fold dilutions of Gossypol were prepared, i.e., 100 µM, 50 µM, down to 0.1 µM in dilution buffer. To each tube was added a solution containing 30 nM of BCL-$X_L$ and 4 nM fluoresceinated peptide. The tubes were incubated for 5 minutes at room temperature and 20 µl each of reaction mixture was transferred to 96-well black PS, HE Microplate (LJL Biosystems Co). All assays were performed in quadruplicate, with blank wells receiving no Gossypol. Then, the plate was read for total intensity and polarization (in mP units) was measured. Controls included dose-responses measurements in absence of the proteins, to assess any interactions between the compounds and the FITC-BH3 peptide. Eventual effects were taken into account by subtraction.

NMR Spectroscopy

2D [$^{15}$N, $^{1}$H]-TROSY spectra for BCL-$X_L$ were measured with 0.5 mM samples of $^{15}$N-labeled BCL-$X_L$. $^{15}$N-labeled and unlabeled BCL-$X_L$ were prepared and purified according to known methods. For chemical-shift mapping and docking studies the three-dimensional structure of BCL-$X_L$ in complex with Bak peptide (PDB code 1BXL) was used. In addition to chemical-shift mapping with labeled proteins, $T_{1\rho}$ measurements and saturation transfer experiments such as WaterLOGSY experiments were also performed to Her validate the binding of the studied compounds to BCL-$X_L$.

All experiments were performed with a 500 MHz Varian Unity+spectrometer or a 600 MHz Bruker Avance600 spectrometer, both equipped with four rf channels and z-axis pulse-field gradients. Selective water saturation was performed with a train of selective IBURP2 pulses of 7 ms durations spaced by a 10 ms delay. Total saturation time used was 2.5 s $T_{1\rho}$ series were measured with a spin-lock pulse of variable length. Measurements were then performed with 1 ms, 10 ms, 50 ms, 150 ms, 200 ms, 250 ms and 300 ms spin-lock time with 100 µM compounds in the absence and presence of 10 µM protein. In all experiments, de-phasing of residual water signals was obtained with a WATERGATE sequence.

Molecular Modeling

Molecular modeling studies were conducted on several R12000SGI Octane workstations with the software package Sybyl version 6.9 (TRIPOS). The docked structure of Gossypol was initially obtained by FlexX as implemented in Sybyl. Two calculations were performed. In the first, all binding-site torsion angles were kept fixed, while in the second side-chain torsion angles were free to change. The average scoring function for the 30 best solutions was only slightly lower when the side-chains were free to rotate. The position of the side-chains in the model did not change substantially from the initial values. The scoring function for (+) gossypol was inferior to (−) gossypol, but the overall positioning of both stereoisomers was very similar.

The resulting best scoring structures were subsequently energy minimized by using the routine DOCK of SYBYL keeping the site rigid. The energy of the ligands after the DOCK minimization was within 5 Kcal/mol from their global minimum of energy. Superposition of compounds was obtained by the routine MULTIFIT of SYBYL. Color figures showing three-dimensional structures were prepped with the programs SYBYL and MOLMOL.

Inhibitory Effect of Compounds on Cancer Cell Survival

The effects of the compounds on viability of tumor cells in culture were monitored by using XTT assays with MCF7 and ZR75-1 cell lines. MCF7 cells were grown in DMEM containing 10% fetal bovine serum, penicillin/streptomycin, supplemented with $10^{-10}$ M insulin, 1 mM sodium pyruvate and glutamine. ZR75-1 cells were grown in RPMI containing 10% fetal bovine serum, penicillin/streptomycin, supplemented with HEPES buffer, 1 mM sodium pyruvate and glutamine. Cells were regularly tested for mycoplasma contamination. Cells were seeded triplicates at an initial cell density of 1,000 cells per well. Blank wells received no cells.

Gossypol, purpurogallin and 5D1 were added at final concentrations of 0, 1, 10 and 100 µM and incubated for three days. Relative numbers of viable cells was determined by XTT assay. Briefly, in a 96-well plate, we added 50 µl of a mixture of 1 mg/ml of XTT (2,3-bis(2-methoxy-4-nitro-5-sulfophenyl)-5-[(phenylamino)carbonyl]-2H-tetrazolium hydroxide) (Polysciences, Washington, Pa.) containing 0.025 mM PMS (phenazine methosulfate) to each well. The 96-well plates were reincubated for an additional 4 hours to allow for XTT formazan production. Then, the contents of each plate were mixed and optical densities were determined at a wavelength of 450 nm ($OD_{450}$). Net $OD_{450}$ was determined after subtracting $OD_{450}$ of blank wells. Low-passage HeLa cells (between passage number 10 and 20) were transfected with pcDNA3-BCL-$X_L$ or control pcDNA3 plasmids using Lipofectamine Plus reagent (Invitrogen) and selected in medium containing 800 µg/ml of G418. Immunoblot analysis of BCL-$X_L$ was accomplished as previously described. HeLa-transfectants were treated with various doses of gossypol, purpurogallin, and its derivatives (0, 1, 3, 10 and 1001.

Chemicals

Pure polyphenols were obtained from SIGMA (gossypol and purpurogallin) and/or from Microsource Discovery Systems (Purpurogallin derivatives). Reference compounds were obtained from Chembridge Corp. (San Diego). Gossypol was tested as a racemic mixture of (+) and (−) isomers. Compounds were dissolved in DMSO at 100 mM concentration and stored at −20 DC. NMR analysis was periodically performed on the compounds as a quality control, prior to further dilution for binding and displacement assays. Reactivity of Gossypol was tested with a 15N-labeled test protein (BIR3 domain of XIAP). A solution containing 1 mM gossypol and 200 μM N-labeled BIR3 was incubated for two hours and the [$^{15}$N,$^{1}$H]-correlation spectrum was recorded and compared with the spectrum of the apo-Bir3. No appreciable differences in the spectra were observed. Results are summarized in Table 5.

TABLE 5

Structure Activity Relationships (SAR) of Purpurogallin Derivatives

| CMPD | $R_1$ | $R_2$ | $R_3$ | $R_4$ | $R_5$ | IC$_{50}$ (μM) (BCL-X$_L$) | IC$_{50}$ (μM) (HeLa) |
|---|---|---|---|---|---|---|---|
| Purpurogallin | —OH | —OH | —OH | —OH | —H | 2.2 | 6.5 |
| 5D1 | —H | —OH | —OH | —OH | —COOC$_2$H$_5$ | 73 | 51.5 |
| 1163 | —H | —OH | —OH | —OH | —COOCH$_3$ | 2.6 | ~30 |
| 1142 | —H | —OH | —OH | —OH | —COOH | 7.4 | 22.9 |
| 6A1 | —OCH$_3$ | —OCH$_3$ | —OCH$_3$ | —OCH$_3$ | —H | >100 | >100 |
| 6A7 | —OCH$_3$ | —OCH$_3$ | —OCH$_3$ | —OCH$_3$ | —H | >100 | >100 |

Although the invention has been described with reference to the above examples, it will be understood that modifications and variations are encompassed within the spirit and scope of the invention. Accordingly, the invention is limited only by the following claims.

What is claimed is:

1. A compound having the structure B:

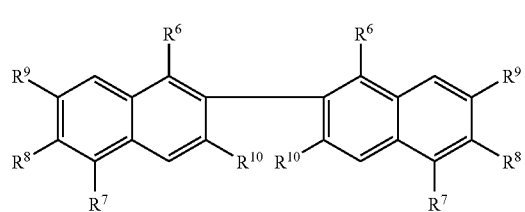

wherein
each of $R^6$, $R^8$, $R^9$ and $R^{10}$ is independently selected from the group consisting of hydrogen, hydroxyl, —(C$_1$-C$_6$)alkyl, —O(C$_1$-C$_6$)alkyl, —(C$_1$-C$_6$)alkylhalo, —OC(O)(C$_1$-C$_6$)alkyl, and halo; and
each $R^7$ is independently selected from the group consisting of (C$_3$-C$_8$)cycloalkyl, —(C$_6$-C$_{10}$)aryl, and —(C$_1$-C$_6$)alkyl(C$_6$-C$_{10}$)aryl, C(O)X, NH(CO)X, SO$_2$NHX, and NHSO$_2$X, wherein X is selected from the group consisting of an alkyl, a substituted alkyl, an aryl, a substituted aryl, an alkylaryl, a substituted alkylaryl and a heterocycle, or a pharmaceutically acceptable salt, hydrate, N-oxide, or solvate thereof.

2. The compound of claim 1, wherein each of $R^6$ and $R^{10}$ is independently selected from the group consisting of —(C$_1$-C$_6$)alkyl, and —O(C$_1$-C$_6$)alkyl.

3. The compound of claim 1, wherein each of $R^8$ and $R^9$ is independently selected from the group consisting of hydrogen, and hydroxyl.

4. The compound of claim 1, wherein $R^8$ and $R^9$ are hydroxyl.

5. The compound of claim 1, wherein the compound is selected from the group consisting of compounds I, III-XX, and XXII:

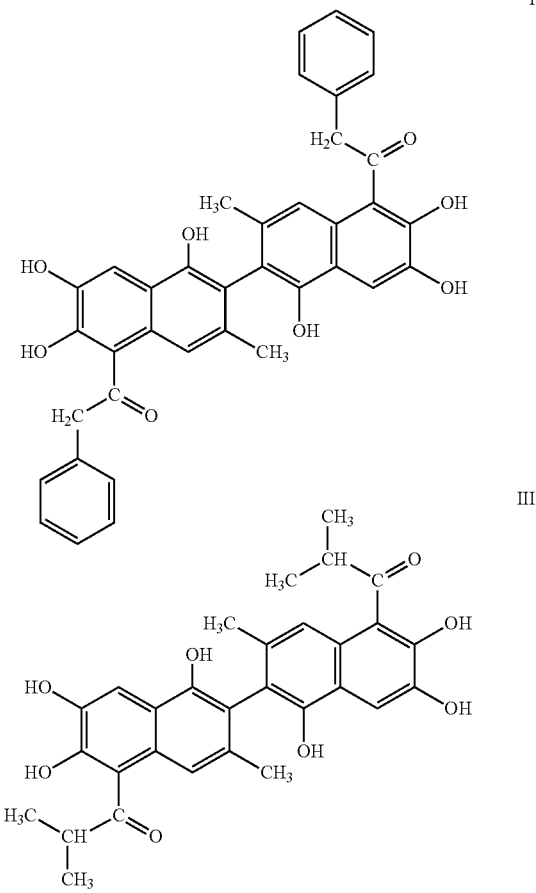

IV
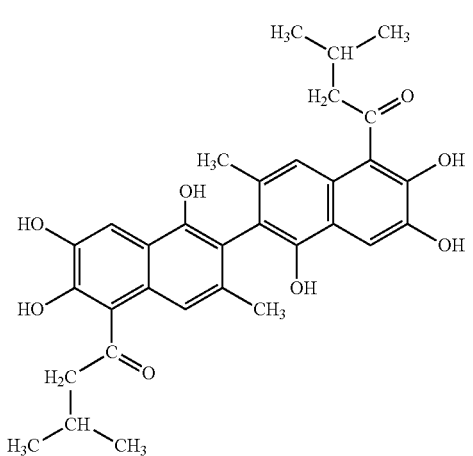
V
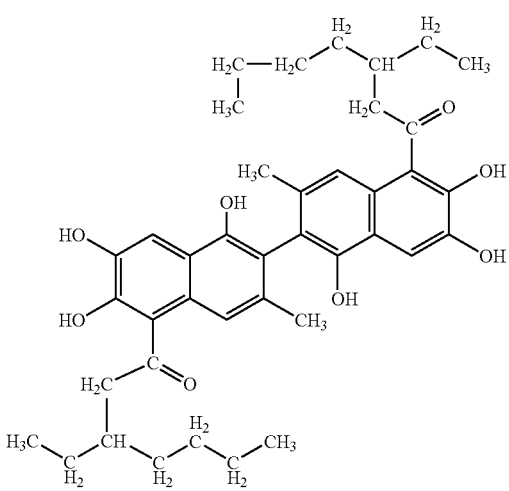
VI
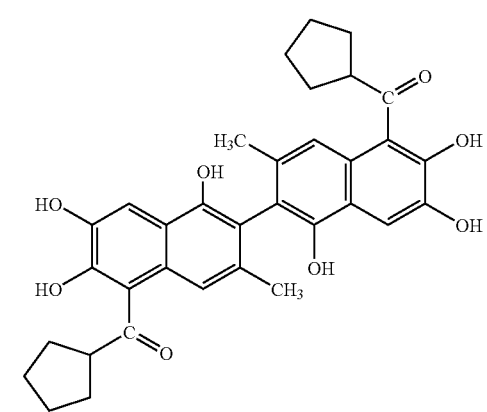
VII
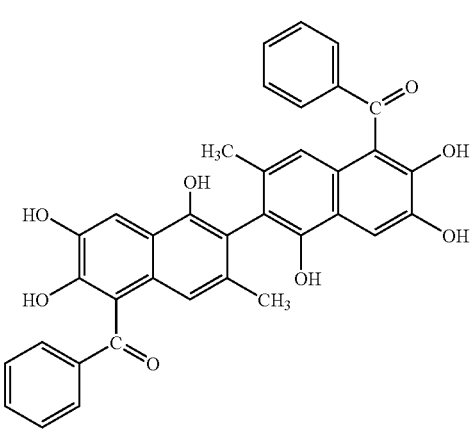
VIII
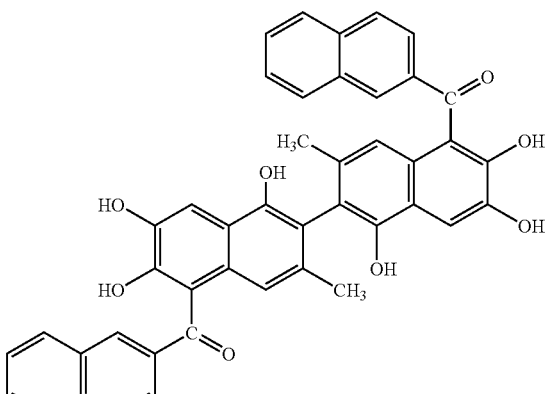
IX
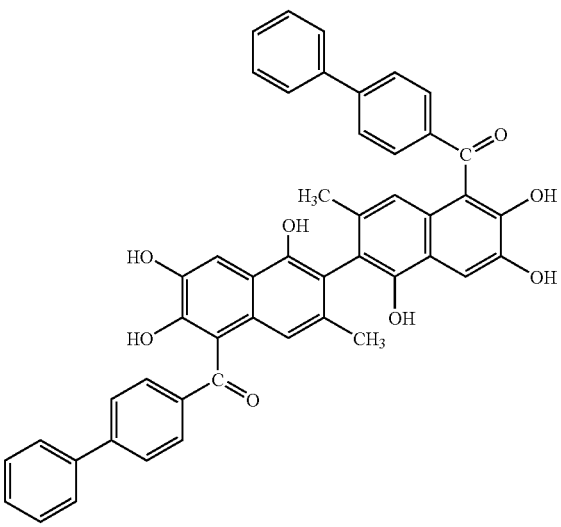

-continued
X
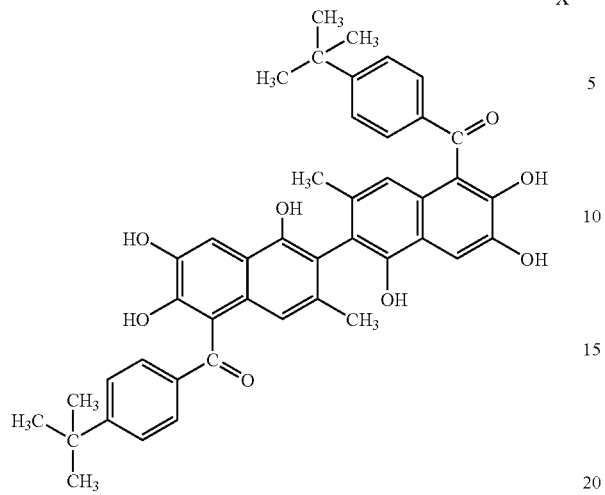
XI
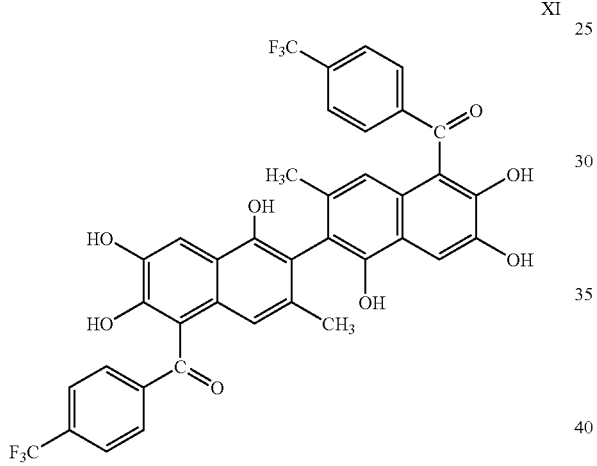
XII
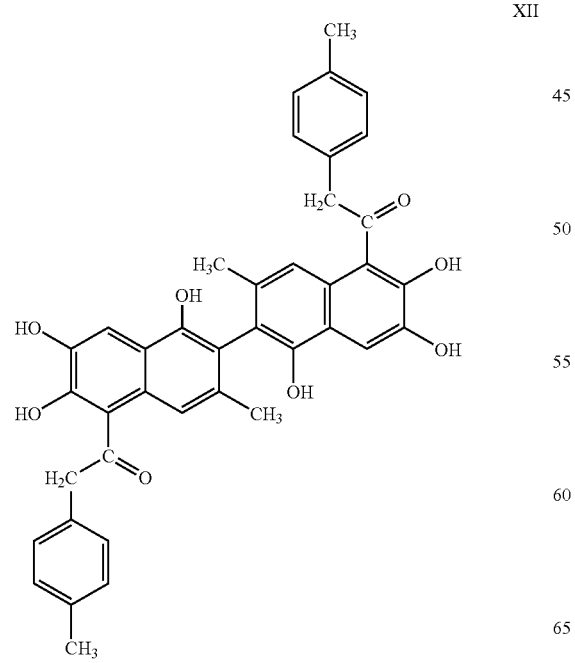
-continued
XIII
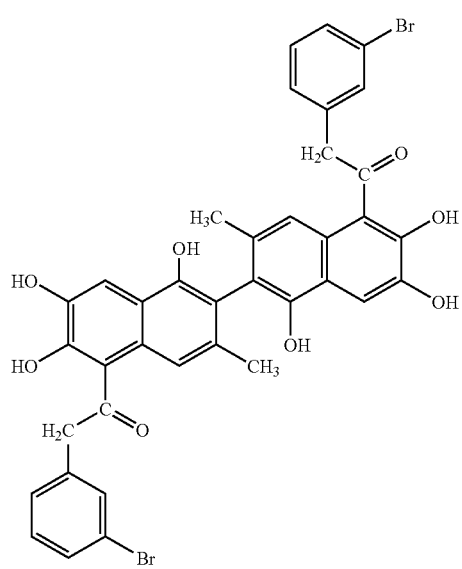
XIV
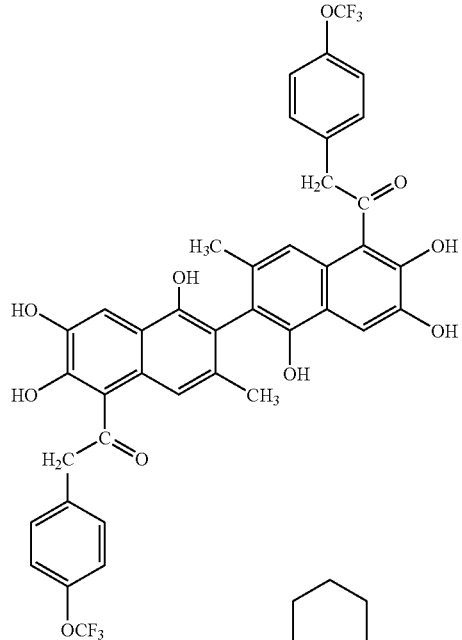
XV
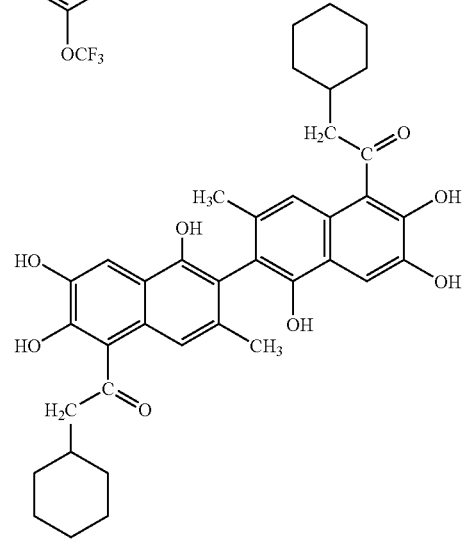

XVI
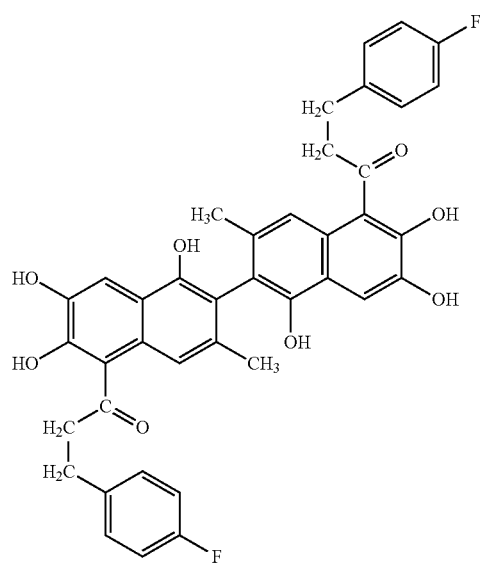
XVII
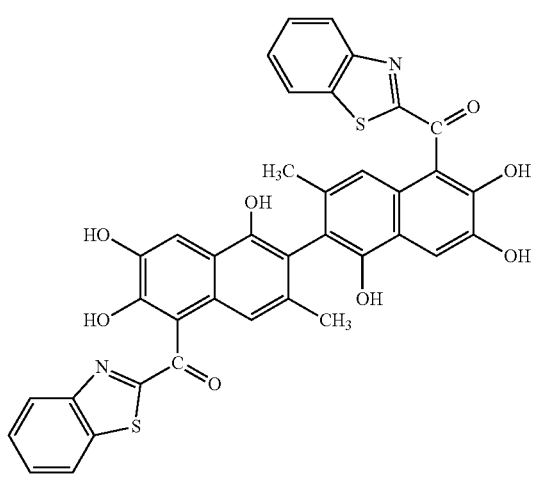
XVIII
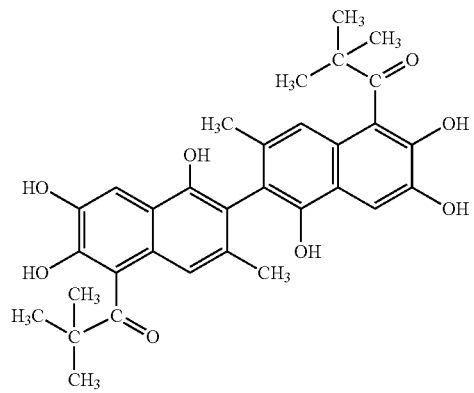
XIX
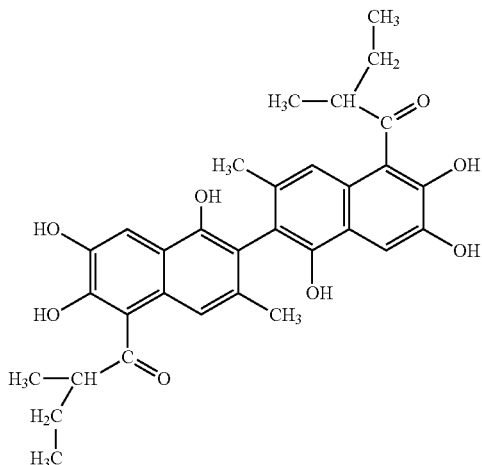
XX
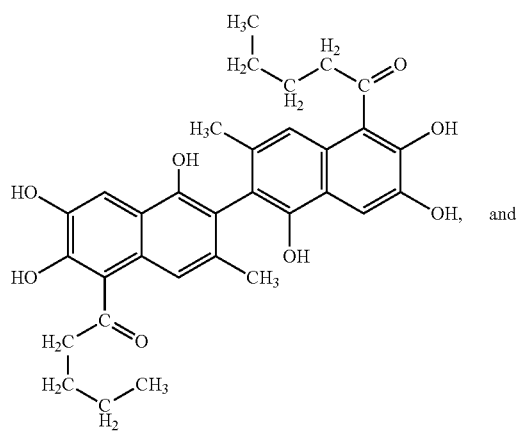
and
XXII
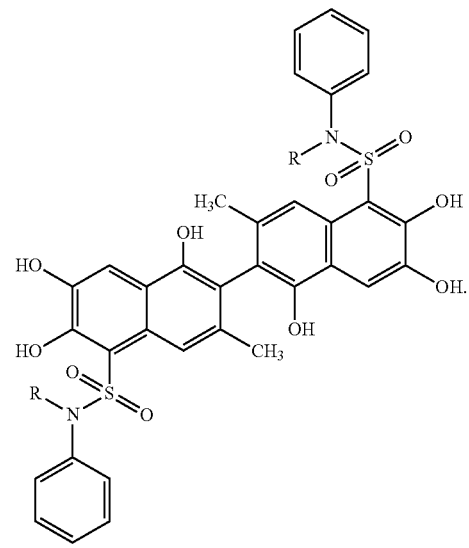
* * * * *